(12) United States Patent
Rabinovich et al.

(10) Patent No.: US 9,610,346 B2
(45) Date of Patent: Apr. 4, 2017

(54) RECOMBINANT VIRAL VECTORS

(71) Applicant: International AIDS Vaccine Initiative, New York, NY (US)

(72) Inventors: Svetlana Rabinovich, Staten Island, NY (US); Maoli Yuan, Brooklyn, NY (US); Aaron J. Wilson, Brooklyn, NY (US); Sanjay Phogat, Edison, NJ (US); Ross W. B. Lindsay, Brooklyn, NY (US); Maria J. Chiuchiolo, Brooklyn, NY (US); Christopher L. Parks, Boonton, NJ (US)

(73) Assignee: International AIDS Vaccine Initiative, New York, NY (US)

( * ) Notice: Subject to any disclaimer, the term of this patent is extended or adjusted under 35 U.S.C. 154(b) by 0 days.

(21) Appl. No.: 13/792,106

(22) Filed: Mar. 10, 2013

(65) Prior Publication Data

US 2013/0266611 A1    Oct. 10, 2013

Related U.S. Application Data

(60) Provisional application No. 61/614,584, filed on Mar. 23, 2012.

(51) Int. Cl.
| | | |
|---|---|---|
| *A61K 39/21* | (2006.01) | |
| *A61K 39/205* | (2006.01) | |
| *A61K 39/12* | (2006.01) | |
| *A61K 39/00* | (2006.01) | |

(52) U.S. Cl.
CPC ............... *A61K 39/21* (2013.01); *A61K 39/12* (2013.01); *A61K 2039/5256* (2013.01); *C12N 2740/16134* (2013.01); *C12N 2760/20243* (2013.01)

(58) Field of Classification Search
CPC ............ A61K 39/21; A61K 2039/5256; C12N 2740/16134; C12N 2760/20243
See application file for complete search history.

(56) References Cited

FOREIGN PATENT DOCUMENTS

| WO | WO 02/00868 | 1/2002 |
|---|---|---|
| WO | WO 2007/123961 | 11/2007 |
| WO | WO 2009/085172 | 7/2009 |
| WO | WO 2010/096678 | 8/2010 |

OTHER PUBLICATIONS

J. Publicover, et al., A Single-Cycle Vaccine Vector Based on Vesicular Stomatitis Virus Can Induce Immune Responses Comparable to Those Generated by a Replication-Competent Vector, Journal of Virology (2005) vol. 79, No. 21, p. 13231-13238.

*Primary Examiner* — Louise Humphrey
(74) *Attorney, Agent, or Firm* — Vedder Price P.C.; Deborah L. Lu

(57) ABSTRACT

The present relation relates to recombinant vesicular stomatitis virus for use as prophylactic and therapeutic vaccines for infectious diseases of AIDS. The present invention encompasses the preparation and purification of immunogenic compositions which are formulated into the vaccines of the present invention.

7 Claims, 41 Drawing Sheets
(36 of 41 Drawing Sheet(s) Filed in Color)

FIG. 4

HIV-1 JRFL    ...Q₆₅₅ELLELDKWASLWNWFDITNWLWYIK IFIM...
                        MPER              TM

VSV Indiana   ...E₄₄₇SLFFGDTGLSKNPIELVEGWFSSWK SSIA...
                        Stem              TM ...SGELLELDKWASLG...
                              ↓                    } Insertion
                    ...ESLFFGDTGLSKNPIELVE...         (with linker aa)
                              ↓
VSV G-2F5-Ins   ...ESLFFGDTGSGELLELDKWASLGLSKNPIELVE...

...ELLELDKWASLWNWFDITN...
                    ...SKNPIELVEGWFSSWK...
                              ↓
VSV G-2F5-Sub   ...SKNPIELLELDKWASLWNWFSSWK...

} Substitution
                    ...DITNWLWYIK...
                    ...ELVEGWFSSWKSSIA...
                              ↓
VSV G-4E10-Sub  ...VEGWDITNWLWYIKSSIA...

VSV G-2F5-4E10-Sub  ...SKNPIELLELDKWASLWNWDITNWLWYIKSSIA...

FIG. 6

|  | Leader | Ectodomain | Stem | TM | CT |
|---|---|---|---|---|---|

VSV-G wt

VSV-G-2F5-Ins

VSV-G-2F5-Sub

VSV-G-4E10-Sub

VSV-G-2F5-4E10-Sub

```
   1 tcaatattgg ccattagcca tattattcat tggttatata gcataaatca atattggcta
  61 ttggccattg catacgttgt atctatatca taatatgtac atttatattg gctcatgtcc
 121 aaatatgaccg ccatgttggc attgattatt gactagttat taatagtaat caattacggg
 181 gtcattagtt catagcccat atatggagtt ccgcgttaca taacttacgg taaatggccc
 241 gcctggctga ccgcccaacg accccgcc attgacgtca ataatgacgt atgttcccat
 301 agtaacgcca atagggactt tccattgacg tcaatgggtg gagtatttac ggtaaactgc
 361 ccacttggca gtacatcaag tgtatcatat gccaagtccg cccctattg acgtcaatga
 421 cggtaaatgg cccgcctggc attatgccca gtacatgacc ttacgggact ttcctacttg
 481 gcagtacatc tacgtattag tcatcgctat taccatggtg atgcggtttt ggcagtacac
 541 caatgggcgt ggatagcggt ttgactcacg gggatttcca agtctccacc ccattgacgt
 601 caatgggagt ttgttttggc accaaaatca acgggacttt ccaaaatgtc gtaacaactg
 661 cgatcgcccg cccgttgac gcaaatgggc ggtaggcgtg tacggtggga ggtctatata
 721 agcagagctc gtttagtgaa ccgtcagatc actagaagct ttattgcggt agtttatcac
 781 agttaaattg ctaacgcagt cagtgcttct gacacaacag tctcgaactt aagctgcagt
 841 gactctctta aggtagcctt gcagaagttg gtcgtgaggc actgggcagg taagtatcaa
 901 ggttacaaga caggtttaag gagaccaata gaaactgggc ttgtcgagac agaagact
 961 cttgcgtttc tgataggcac ctattggtct tactgacatc cactttgcct ttctctccac
1021 aggtgtccac tcccagttca attacagctc ttaaggcgag agtactcgta cgctagcctc
1081 gagaggagcc accatgaagt gctgctgta cctggcctc ctgttcatcg gcgtgaactg
1141 caagttcacc atcgtgttcc cccacaacca gaagggcaac tggaagaacg tgcccagcaa
1201 ctaccactac tgccccagca gcagcgacct gaactggcac aacgacctga tcggcacgc
1261 cctgcaagtc aagatgccca agagccacaa ggccatccag gccgacggct ggatgtgcca
1321 cgccagcaag tgggtgacca cctgcgactt ccggtggtac ggccccaagt acatcaccca
1381 cagcatccgc agcttcaccc caagcgtgga gcagtgcaag gagagcatcg agcagaccaa
1441 gcagggcacc tggctgaacc ccggcttccc tccacaaagc tgcggctacg ccacgtgac
1501 cgacgcgag gcgccatcg tgcaggtgac ccctcaccac gtgctggtgg acgagtacac
1561 cggcgagtgg gtggacagcc agttcatcaa cggcaagtgc agcaacgaca tctgccccac
1621 cgtgcacaac agcaccacct ggcacagcga ctacaaagtg aagggcctgt gcgacagcaa
1681 cctgatcagc accgacatca ccttcttctc cgaggacggc gagctgagca ggctgagact
1741 ggagggcacc ggcttccgca gcaactactt cgcctacgag accggcgaca aggcctgcaa
1801 gatgcagtac tgcaagcact ggggcgtgcg cctgcccagc ggcgtgtggt tcgagatggc
1861 cgacaaggac ctgttcgccg ccgccgctt ccccgagtgc cccgagggca gcagcatcag
1921 cgccccaagc cagaccagcg tggacgtgag cctgatccag gacgtggagc ctcctgga
1981 ctacagcctg tgccaggaga cctggagcaa gatccgcgcc ggcctgcca tcagccgt
2041 ggacctgagc tacctgcccc ctaagaaccc cggcaccggc cccgtgttca ccatcatcaa
2101 cggcaccctg aagtacttcg agacccgcta catccgcgtg gacatcgccg ccccaatcct
2161 gagccgcatg gtgggcatga tcagcggcac caccacccag cgcagctgt gggacgactg
2221 ggcccttac gaggacgtgg agatcggcc taacggcgtg ctgcgcacca gctgggcta
2281 caagtttccc ctgtacatga tcggccacgg catgctggac agcgacctgc acctgagcag
2341 caaggccag gtgttcgagc atccccacat ccaggacgcc gccagccagc tgcccgacga
2401 cgagaccctg ttcttcggcg acaccgggct gagcaagaac ccccatcgagt tcgtggaggg
2461 ctggttcagc agctggaaga gcagcatcgc cagcttcttc ttcatcatcg gcctgatcat
2521 cggcctgttc ctgtgctgc gcgtgggcat ctacctgtgc atcaagctga agcacaccaa
2581 gaagcgccag atctacaccg acatcgagat gaaccgcctg ggcaagtaaa gcggccgctt
2641 cccttagtg agggttaatg cttcgagcag acatgataag atacattgat gagtttggac
2701 aaaccacaac tagaatgcag tgaaaaaaat gctttatttg tgaaatttgt gatgctattg
2761 ctttatttgt aaccattata agctgcaata aacaagttaa caacaacaat tgcattcatt
2821 ttatgtttca ggttcagggg gagatgtggg aggttttta aagcaagtaa aacctctaca
2881 aatgtggtaa aatccgataa ggatcgatcc gggctggcgt aatagcgaag aggcccgcac
2941 cgatcgccct tcccaacagt tgcgcagcct gaatggcgaa tggacgcgcc ctgtagcggc
3001 gcattaagcg cggcgggtgt ggtggttacg cgcagcgtga ccgctacact tgccagcgc
3061 ctagcgcccg ctccttcgc tttcttccct tcctttctcg ccacgttcgc cggctttccc
3121 cgtcaagctc taaatcgggg gctcccttta gggttccgat ttagtgcttt acggcacctc
3181 gaccccaaaa aacttgatta gggtgatggt tcacgtagtg gccatcgcc ctgatagcg
3241 gttttttcgcc ctttgacgtt ggagtccacg ttctttaata gtggactctt gttccaaact
3301 ggaacaacac tcaaccctat ctcggtctat tcttttgatt tataagggat tttgccgatt
3361 tcggcctatt ggttaaaaaa tgagctgatt taacaaaaat ttaacgcgaa ttttaacaaa
3421 atattaacgc ttacaatttc ctgatgcggt attttctcct tacgcatctg tgcggtattt
3481 cacaccgcat acgcggatct gcgcagcacc atggcctgaa ataacctctg aaagaggaac
```

FIG. 27A

```
3541 ttggttaggt accttctgag gcggaaagaa ccagctgtgg aatgtgtgtc agttagggtg
3601 tggaaagtcc ccaggctccc cagcaggcag aagtatgcaa agcatgcatc tcaattagtc
3661 agcaaccagg tgtggaaagt ccccaggctc cccagcaggc agaagtatgc aaagcatgca
3721 tctcaattag tcagcaacca tagtcccgcc cctaactccg cccatcccgc ccctaactcc
3781 gcccagttcc gcccattctc cgcccccatgg ctgactaatt ttttttattt atgcagaggc
3841 cgaggcgcc tcggcctctg agctattcca gaagtagtga ggaggctttt ttggaggcct
3901 aggcttttgc aaaaagcttg attcttctga cacaacagtc tcgaacttaa ggctagagcc
3961 accatgattg aacaagatgg attgcacgca ggttctccgg ccgcttgggt ggagaggcta
4021 ttcggctatg actgggcaca acagacaatc ggctgtctg atgccgccgt gttccggctg
4081 tcagcgcagg ggcgcccggt tctttttgtc aagaccgacc tgtccggtgc cctgaatgaa
4141 ctgcaggacg aggcagcgcg gctatcgtgg ctggccacga cgggcgttcc ttgcgcagct
4201 gtgctcgacg ttgtcactga agcgggaagg gactggctg tattgggcga agtgccgggg
4261 caggatctcc tgtcatctca ccttgctcct gccgagaaag tatccatcat ggctgatgca
4321 atgcggcggc tgcatacgct tgatccggct acctgcccat tcgaccacca agcgaaacat
4381 cgcatcgagc gagcacgtac tcggatggaa gccggtcttg tcgatcagga tgatctggac
4441 gaagagcatc aggggctcgc gccagccgaa ctgttcgcca ggctcaaggc gcgcatgccc
4501 gacggcgagg atctcgtcgt gacccatggc gatgcctgct tgccgaatat catggtggaa
4561 aatggccgct tttctggatt catcgactgt ggccggctgg gtgtggcgga ccgctatcag
4621 gacatagcgt tggctacccg tgatattgct gaagagcttg gcggcgaatg ggctgaccgc
4681 ttcctcgtgc tttacggtat cgccgctccc gattcgcagc gcatcgcctt ctatcgcctt
4741 cttgacgagt tcttctgagc gggactctgg ggttcgaaat gaccgaccaa gcgacgccca
4801 acctgccatc acgatggccg caataaaata tctttatttt cattacatct gtgtgttggt
4861 tttttgtgtg aatcgatagc gataaggatc gcgtatggt gcactctcag tacaatctgc
4921 tctgatgccg catagttaag ccagccccga cacccgccaa caccgctga cgcgccctga
4981 cgggcttgtc tgctcccggc atccgcttac agacaagctg tgaccgtctc cgggagctgc
5041 atgtgtcaga ggttttcacc gtcatcaccg aaacgcgcga gacgaaaggc cctcgtgata
5101 cgcctatttt tataggttaa tgtcatgata ataatggttt cttagacgtc aggtggcact
5161 tttcggggaa atgtgcgcgg aacccctatt tgtttatttt tctaaataca ttcaaatatg
5221 tatccgctca tgagacaata accctgataa atgcttcaat aatattgaaa aaggaagagt
5281 atgagtattc aacatttccg tgtcgccctt attcccttt ttgcggcatt ttgccttcct
5341 gttttgctc acccagaaac gctggtgaaa gtaaaagatg ctgaagatca gttgggtgca
5401 cgagtgggtt acatcgaact ggatctcaac agcggtaaga tccttgagag ttttcgcccc
5461 gaagaacgtt ttccaatgat gagcactttt aaagttctgc tatgtggcgc ggtattatcc
5521 cgtattgacg ccgggcaaga gcaactcggt cgccgcatac actattctca gaatgacttg
5581 gttgagtact caccagtcac agaaaagcat cttacggatg gcatgacagt aagagaatta
5641 tgcagtgctg ccataaccat gagtgataac actgcggcca acttacttct gacaacgatc
5701 ggaggaccga aggagctaac cgcttttttg cacaacatgg gggatcatgt aactcgcctt
5761 gatcgttggg aaccggagct gaatgaagcc ataccaaacg acgagcgtga caccacgatg
5821 cctgtagcaa tggcaacaac gttgcgcaaa ctattaactg gcgaactact tactctagct
5881 tcccggcaac aattaataga ctggatggag gcggataaag ttgcaggacc acttctgcgc
5941 tcggcccttc cggctggctg gtttattgct gataaatctg gagccggtga gcgtgggtct
6001 gcggtatca ttgcagcact ggggccagat ggtaagccct cccgtatcgt agttatctac
6061 acgacgggga gtcaggcaac tatgatgaa cgaaatagac agatcgctga gataggtgcc
6121 tcactgatta gcattggta actgtcagac caagttact catatatact ttagattgat
6181 ttaaaacttc atttttaatt taaaaggatc taggtgaaga tcctttttga taatctcatg
6241 accaaaatcc cttaacgtga gttttcgttc cactgagcgt cagaccccgt agaaaagatc
6301 aaaggatctt cttgagatcc ttttttctg cgcgtaatct gctgcttgca aacaaaaaaa
6361 ccaccgctac cagcggtggt ttgtttgccg gatcaagagc taccaactct ttttccgaag
6421 gtaactggct tcagcagagc gcagatacca aatactgttc ttctagtgta gccgtagtta
6481 ggccaccact tcaagaactc tgtagcaccg cctacatacc tcgctctgct aatcctgtta
6541 ccagtggctg ctgccagtgg cgataagtcg tgtcttaccg ggttggactc aagacgatag
6601 ttaccggata aggcgcagcg gtcgggctga acggggggtt cgtgcacaca gcccagcttg
6661 gagcgaacga cctacaccga actgagatac ctacagcgtg agctatgaga aagcgccacg
6721 cttcccgaag ggagaaaggc ggacaggtat ccggtaagcg gcagggtcgg aacaggagag
6781 cgcacgaggg agcttccagg gggaaacgcc tggtatcttt atagtcctgt cgggtttcgc
6841 cacctctgac ttgagcgtcg atttttgtga tgctcgtcag ggggcggag cctatggaaa
6901 aacgccagca acgcggcctt tttacggttc ctggccttt gctggccttt tgctcacatg
6961 gctcgacaga tct
```

FIG. 27B

A  G gene 1561 bp

B

```
ctcgagaggagccaccATGAAGTGCCTGCTGTACCTGGCCTTCCTGTTCA
TCGGCGTGAACTGCAAGTTCACCATCGTGTTCCCCCACAACCAGAAGGGC
AACTGGAAGAACGTGCCCAGCAACTACCACTACTGCCCCAGCAGCAGCGA
CCTGAACTGGCACAACGACCTGATCGGCACCGCCCTGCAaGTCAAGATGC
CCAAGAGCCACAAGGCCATCCAGGCCGACGGCTGGATGTGCCACGCCAGC
AAGTGGGTGACCACCTGCGACTTCCGgTGGTACGGCCCCAAGTACATCAC
CCACAGCATCCGCAGCTTCACCCCaAGCGTGGAGCAGTGCAAGGAGAGCA
TCGAGCAGACCAAGCAGGGCACCTGGCTGAACCCCGGCTTCCCtCCaCAa
AGCTGCGGCTACGCCACCGTGACCGACGCCGAGGCCGCCATCGTGCAGGT
GACCCCtCACCACGTGCTGGTGGACGAGTACACCGGCGAGTGGGTGGACA
GCCAGTTCATCAACGGCAAGTGCAGCAACGACATCTGCCCCACCGTGCAC
AACAGCACCACCTGGCACAGCGACTACAAaGTGAAGGGCCTGTGCGACAG
CAACCTGATCAGCACCGACATCACCTTCTTCtccGAGGACGGCGAGCTGA
GCAGCCTGGGCAAGGAGGGCACCGGCTTCCGCAGCAACTACTTCGCCTAC
GAGACCGGCGACAAGGCCTGCAAGATGCAGTACTGCAAGCACTGGGGCGT
GCGCCTGCCCAGCGGCGTGTGGTTCGAGATGGCCGACAAGGACCTGTTCG
CCGCCGCCCGCTTCCCCGAGTGCCCCGAGGGCAGCAGCATCAGCGCCCCa
AGCCAGACCAGCGTGGACGTGAGCCTGATCCAGGACGTGGAGCGCATCCT
GGACTACAGCCTGTGCCAGGAGACCTGGAGCAAGATCCGCGCCGGCCTGC
CCATCAGCCCCGTGGACCTGAGCTACCTGGCCCCtAAGAACCCCGGCACC
GGCCCCGTGTTCACCATCATCAACGGCACCCTGAAGTACTTCGAGACCCG
CTACATCCGCGTGGACATCGCCGCCCCaATCCTGAGCCGCATGGTGGGCA
TGATCAGCGGCACCACCACCGAGCGCGAGCTGTGGGACGACTGGGCCCCt
TACGAGGACGTGGAGATCGGCCCtAACGGCGTGCTGCGCACCAGCCTGGG
CTACAAGTTtCCCCTGTACATGATCGGCCACGGCATGCTGGACAGCGACC
TGCACCTGAGCAGCAAGGCCCAGGTGTTCGAGCAtCCCCACATCCAGGAC
GCCGCCAGCCAGCTGCCCGACGACGAGACCCTGTTCTTCGGCGACACCGG
CCTGAGCAAGAACCCCATCGAGTTCGTGGAGGGCTGGTTCAGCAGCTGGA
AGAGCAGCATCGCCAGCTTCTTCTTCATCATCGGCCTGATCATCGGCCTG
TTCCTGGTGCTGCGCGTGGGCATCTACCTGTGCATCAAGCTGAAGCACAC
CAAGAAGCGCCAGATCTACACCGACATCGAGATGAACCGCCTGGGCAAGT
AAgcggccgc
```

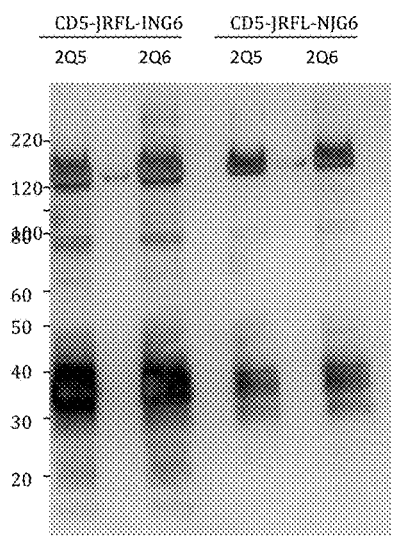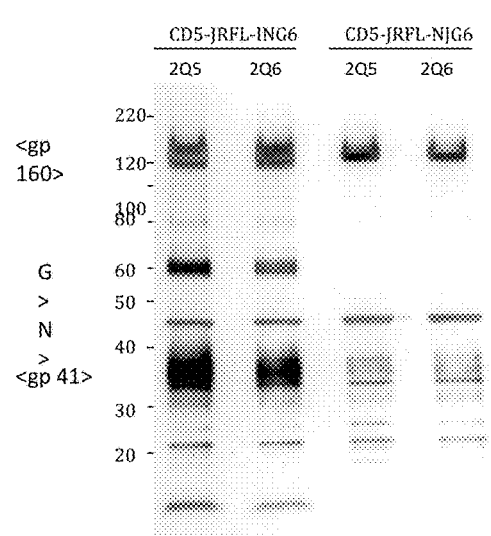
FIGS. 30A-B

FIG. 31

FIG. 32 rVSV wild type
rVSV-GS68MPER-G$_{in6}$ no ab | 2F5 | 4E10 | Vi-10

| GS68MPER | N | P | M | L | G |

FIG. 36

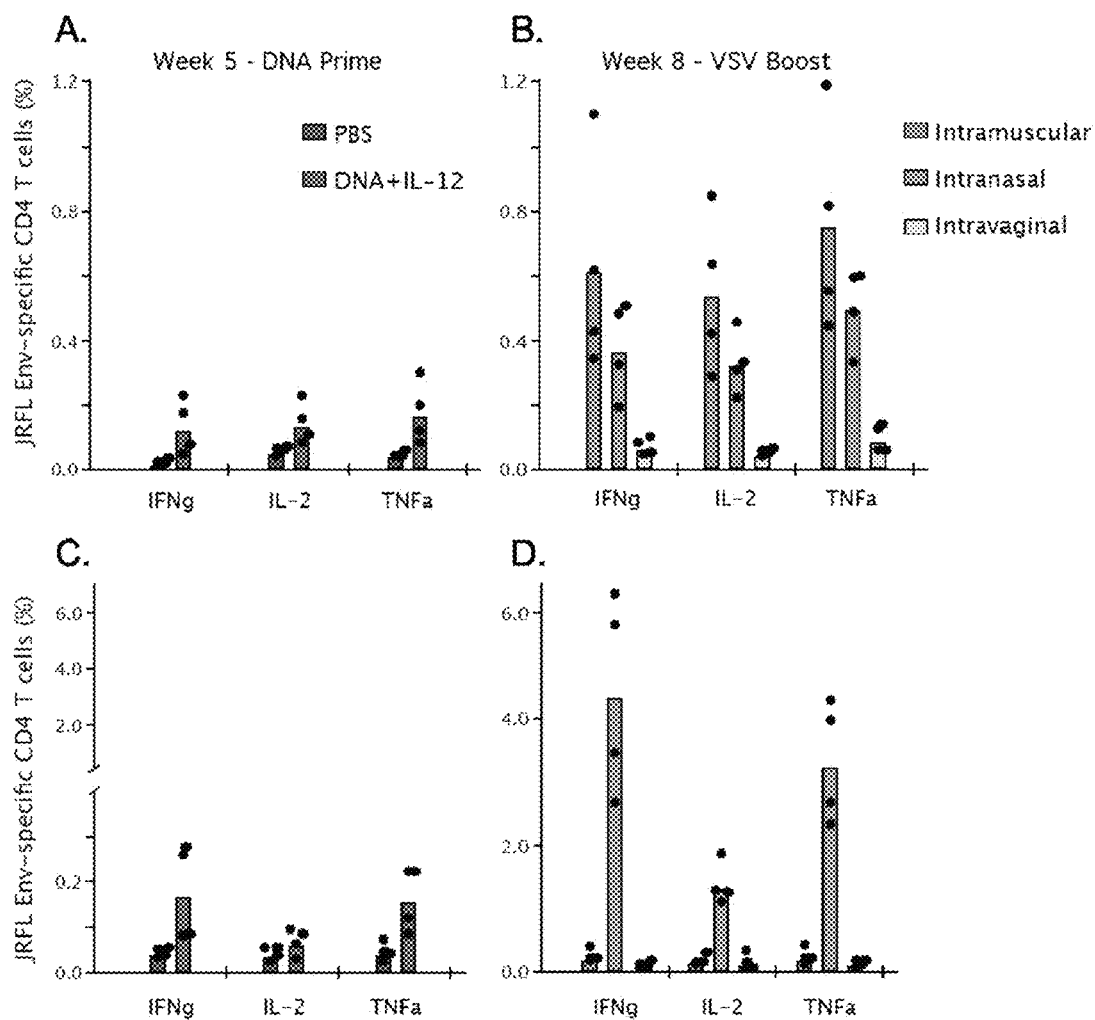
FIGS. 40A-D

US 9,610,346 B2

RECOMBINANT VIRAL VECTORS

INCORPORATION BY REFERENCE

This application claims priority to U.S. provisional patent application Ser. No. 61/614,584 filed Mar. 23, 2012. Reference is made to U.S. patent application Ser. No. 12/708,940 filed Feb. 19, 2010, U.S. provisional patent application Ser. Nos. 61/537,497 filed Sep. 21, 2011; 61/552,240 filed Oct. 27, 2011 and 61/617,368 filed Mar. 29, 2012.

The foregoing applications, and all documents cited therein or during their prosecution ("appln cited documents") and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FEDERAL FUNDING LEGEND

This invention was supported, in part, by CAVD Grant ID: 38606, CAVD Grant ID: OPP1033117 and NIAID R01: 1R01AI084840-01. The federal government may have certain rights to this invention.

FIELD OF THE INVENTION

The present invention relates to recombinant vesicular stomatitis virus for use as prophylactic and therapeutic vaccines for infectious diseases of AIDS.

SEQUENCE LISTING

The instant application contains a Sequence Listing which has been submitted in ASCII format via EFS-Web and is hereby incorporated by reference in its entirety. Said ASCII copy, created on Mar. 21, 2013, is named 43094.01.2022_SL.txt and is 71,024 bytes in size.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as $CD4^+$ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of $CD4^+$ T-lymphocytes, which are critical to immune defense, is a major cause of the progressive immune dysfunction that is the hallmark of AIDS disease progression. The loss of $CD4^+$ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 19; 280(5371):1884-8). For fusion with its target cells, HIV-1 uses a trimeric Env complex containing gp120 and gp41 subunits (Burton et al., Nat. Immunol. 2004 March; 5(3): 233-6). The fusion potential of the Env complex is triggered by engagement of the CD4 receptor and a coreceptor, usually CCRS or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001;

77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

There remains a need to express immunogens that elicit broadly neutralizing antibodies. Strategies include producing molecules that mimic the mature trimer on the virion surface, producing Env molecules engineered to better present neutralizing antibody epitopes than wild-type molecules, generating stable intermediates of the entry process to expose conserved epitopes to which antibodies could gain access during entry and producing epitope mimics of the broadly neutralizing monoclonal antibodies determined from structural studies of the antibody-antigen complexes (Burton et al., Nat. Immunol. 2004 March; 5(3):233-6). However, none of these approaches have yet efficiently elicited neutralizing antibodies with broad specificity.

Citation or identification of any document in this application is not an admission that such document is available as prior art to the present application.

SUMMARY OF THE INVENTION

The current invention is based, in part, on Applicant's discovery that HIV gp41 epitopes known to elicit broadly neutralizing antibodies inserted into a viral glycoprotein are recognized by such broadly neutralizing antibodies in cells infected with the recombinant virus expressing the viral glycoprotein.

Recombinant viruses are viruses generated by introducing foreign genetic material into the genome of the virus. The genome of a virus can comprise either DNA or RNA. The genome of an RNA virus can be further characterized to be either positive-sense (plus-strand) or negative-sense (minus-strand). A plus-strand (5' to 3') viral RNA indicates that a particular viral RNA sequence can be directly translated into the desired viral proteins whereas a minus-strand (3' to 5') viral RNA must be first converted to a positive-sense by an RNA polymerase prior to translation.

In a first embodiment, the invention relates to a recombinant vesicular stomatitis virus (VSV) vector wherein the gene encoding the VSV surface glycoprotein G (VSV G) may be functionally replaced by HIV Env. The HIV Env may be recognized by antibodies PG9, PG16, 2G12, b12, 2F5, 4E10 or Z13 or other antibodies, including potent broadly neutralizing trimer-specific antibodies. VSV is a minus-strand RNA virus that can infect insects and mammals.

In a second embodiment, the invention relates to a recombinant vesicular stomatitis virus (VSV) vector encoding a modified form of VSV G, wherein the modified form of VSV G may harbor epitopes from the HIV Env membrane proximal external region (MPER). The MPER sequence may be inserted into the membrane proximal region or other domains of VSV G. The G-MPER protein may bind with high avidity to 2F5, 4E10 or other monoclonal antibodies.

In a third embodiment, the invention relates to a recombinant vesicular stomatitis virus (VSV) vector encoding a N-terminally truncated form of VSV G (G/Stem), wherein the G/Stem may display Env epitope sequences on the surface of VSV particles. The G/Stem may contain a cytoplasmic tail (CT) and trans-membrane (TM) spanning domains of G, a 16- to 68-amino acid membrane proximal extracellular polypeptide (the Stem), wherein HIV Env epitopes are appended to or inserted into the Stem. The HIV Env epitopes may be derived from the gp41 MPER or other regions of Env. The G/Stem-HIV Env epitope molecules may bind to 2F5, 4E10 or other monoclonal antibodies with high affinity.

In a fourth embodiment, the invention relates to a method of generating novel chimeric HIV Env-VSV G (EnvG) molecules expressed and incorporated into VSV which may comprise:
  (a) serially passaging replication-competent chimeric VSV-HIV viruses that lack the capacity to encode wild-type G and are dependent on Env or chimeric EnvG molecules for infection and propagation on cells to promote emergence of viruses with greater replicative fitness and
  (b) identifying novel mutations that enhance Env or EnvG function in VSV-HIV viruses.

The cells may be CD4/CCR5$^+$ cells. The novel mutations may escalate trimer abundance on the virus particle and/or increase the stability of the functional trimeric form of Env or EnvG. The method may further comprise determining whether the Env or EnvG immunogens elicit broadly neutralizing anti-Env antibodies.

In a fifth embodiment, the invention relates to method of applying selective pressure to generate novel Env, EnvG, or G/Stem-antigen chimeras molecules expressed and incorporated into VSV, wherein the selective pressure may be binding to an antibody of interest, thereby enriching for molecules that may be more immunogenic. The antibody may be 2F5, 4E10, or other Env-specific antibodies.

The present invention also encompasses methods of producing or eliciting an immune response which may comprise administering to a mammal any one of the herein disclosed recombinant VSV vectors.

The present invention also encompasses other plus and minus strand viruses which can be used as recombinant viral vectors in the method of the invention. Such viruses include but are not limited to: Measles virus, Canine distemper virus, Parainfluenza viruses, Sendai virus, Newcastle disease virus, Venezuelan equine encephalitis virus, Sindbis virus, Semliki Forrest virus etc.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in □ U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings, in which:

Figure 4:
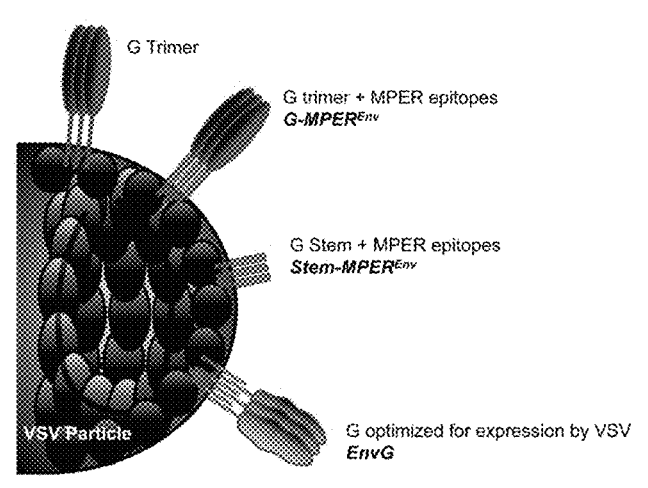

FIG. 4 depicts HIV Env Immunogens presented on the VSV vector platform. The different chimeric envelope proteins are illustrated from top to bottom: i) the native VSV G trimer, ii) a G trimer with the gp41 MPER inserted into the stem region of G; iii) the G/Stem displaying MPER epitopes; and iv) the Env ectodomain including the MPER, which is incorporated into the VSV particle via the transmembrane segment and cytoplasmic tail of G.

FIG. 6 depicts HIV-1 Env MPER and VSV G stem sequence alignment and insertion/substitution strategies. Top, The MPER of HIV-1 gp41 (JRFL strain) and the Stem region of VSV G (Indiana strain) share sequence similarities, which guided the selection of insertion or substitution points in the Stem region for the 2F5 and 4E10 epitopes. The transmembrane domains and the first two residues of the cytoplasmic tails are depicted on the right. Hydrophobic residues are shown in blue. Middle, Generation of the VSV G-2F5-Ins construct by insertion of the 2F5 epitope into the G stem region. Flanking linker residues are shown in green. Bottom, Substitution of residues in the G stem region with the 2F5 and/or 4E10 epitopes, resulting in the VSV G-2F5-Sub, VSV G-4E10-Sub, and VSV G-2F5-4E10-Sub constructs. Sequences similarities between HIV gp41 and VSV G are shown in red. FIG. 6 discloses SEQ ID NO: 41-52, respectively, in order of appearance.

FIG. 7 depicts insertion points for the 2F5 and 4E10 epitopes in the context of full-length VSV G. The leader peptide, ectodomain, Stem, TM and CT of VSV G are illustrated. The arrow denotes insertion of the 2F5 epitope, while the orange and blue boxes indicate substitution of the 2F5 and 4E10 epitopes, respectively.

FIG. 11 depicts cell-cell fusion mediated by VSV G. 293T cells transfected with VSV G constructs were exposed briefly to a medium with pH 5.2. After 6-8 hours, formation of syncitia was monitored using a light microscope. The inset in the panel for VSV G-2F5-4E10 at the bottom right shows a small syncitium, which occurs rarely for this construct.

FIG. 13 depicts infectivity of lentiviral particles pseudotyped with VSV G constructs. GFP reporter lentiviruses pseudotyped with VSV G variants were generated in 293T cells and used subsequently to infect naive 293T cells. GFP expression was monitored 72 hours post-infection.

FIG. 14 depicts quantification of infectivity of lentiviral particles pseudotyped with VSV G constructs. Naïve 293T cells were infected with luciferase reporter lentiviruses pseudotyped with VSV G variants, followed by quantification of luciferase expression 48 hours post-infection.

FIG. 15 depicts neutralization of lentiviral particles pseudotyped with VSV G constructs with the 2F5 or 4E10 antibodies. Luciferase reporter lentiviruses pseudotyped with VSV G, VSV G-2F5-Sub or VSV G-4E10-Sub were incubated with various concentrations of 2F5 (left panel) or 4E10 antibody (right panel) prior to infection of naïve cells. Luciferase expression was quantified 48 hours post-infection.

FIG. 17 depicts neutralization of recombinant VSV with 2F5 and 4E10 antibodies. Recombinant VSV containing wild-type G, G-2F5-Sub, G-4E10-Sub or G-2F5-4E10-Sub was incubated with various concentrations of the broadly neutralizing monoclonal antibodies VI-10 (which reacts with the ectodomain of G), 2F5 or 4E10 before addition to naive Vero cells. A standard plaque assay was used to determine the extent of neutralization for each antibody and concentration.

FIGS. 19A-19C depict a schematic illustrating the membrane topology of G and G-Stem proteins. A. Topology of the full-length G protein with the extracellular region, the stem, the transmembrane segment, and the cytoplasmic tail. Four different G-Stem constructs were generated: no stem, short stem, middle stem, and long stem. B. The gp41 MPER was fused to the four G-Stem constructs (GS-MPER fusions). C. Amino acid sequence of the G-Stem (SEQ ID NO: 53). The starting position for each GS variant (no, short, medium, long) is shown. The N-terminal signal sequence is shown in purple, whereas the transmembrane segment is colored red.

Figure 25:
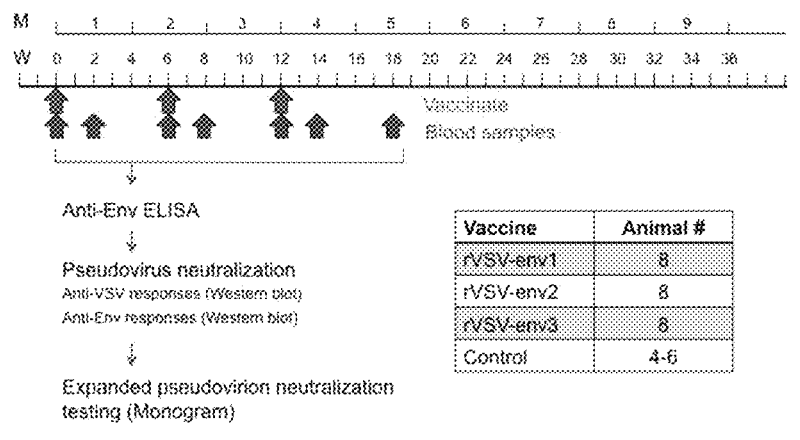

FIG. 25 depicts rabbit immunogenicity testing. Vaccination and blood collection schedules are listed along a timeline (M, months; W, weeks) at the top. Analysis of antibody reactivity is illustrated in the flow diagram at the left side. The chart on the right side outlines a typical rabbit study.

FIGS. 27A-27B depict the plasmid sequence of pCINeo-VSV-G that encodes the G protein from the vesicular stomatitis Indiana virus (SEQ ID NO: 54). Applicants have optimized the gene sequence.

FIGS. 28A-28B depict the unique XhoI and NotI sites (highlighted) added to the 5' and 3' termini respectively of the VSV G coding sequence (SEQ ID NO: 55) as per the Optimization Strategy detailed in Example 5.

FIGS. 29A-E depict VSV genome and viral particles structure. A. scheme of the new viral vector design. Both glycoproteins VSV G (in red) and Env (blue) get incorporated into the VSV particle. B. Gradient of mRNA synthesis from the VSV genome. Genes located at the 3' terminus (position 1) are transcribed more efficiently than the downstream genes. B. Position of the VSV genes in the genome. D. and E. New vectors designed to downregulate expression of G by moving to position 6, and expressing Env inserts from positions 4 (D) and 1 (E).

FIGS. 30A-B depict expression of Env (Clade B) JR-FL protein on infected cells and incorporation of G and Env proteins into viral particles. Western blot analysis of Env JR-FL protein expression in total cell lysates. Total cell lysates were prepared from infected Vero cells with two different clones of VSV-Env JRFL-G6$_{IN}$ (lanes 1 and 2) and two other clones of VSV-Env JRFL G6$_{NJ}$ (lanes 3 and 4).

Clones were originated after two rounds of virus plaque purification. A. EnvG protein detected using monoclonal antibody 2F5. B. Detection of Env JRFL and $G_{IN}$ using an anti-VSV $G_{IN}$ (C-tail) antibody and anti-VSV N polyclonal rabbit antiserum antibody. Note that the $G_{IN}$ C-tail antibody does not recognize G protein for the NJ serotype (lanes 3 and 4)

Figure 31:
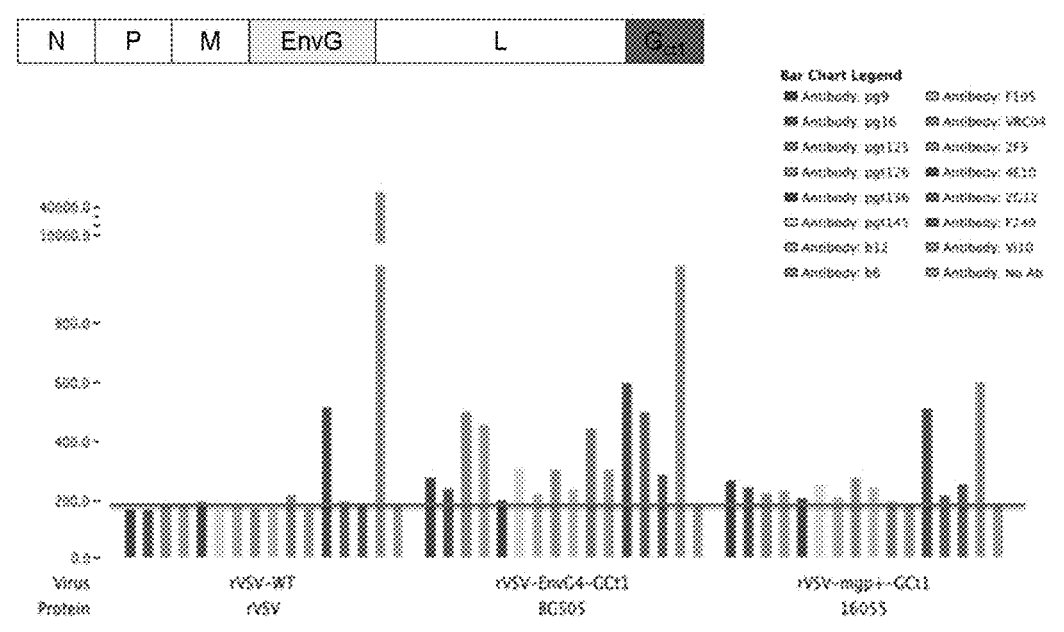

FIG. 31 depicts expression of VSV $G_{CT1}$ and Env (Clade A) BG505 or Env (Clade C) 16055 on the surface of infected cells. Flow cytometry analysis of Vero cells infected with VSV Env (clades A and C)-$G_{CT1}$ using a panel of broadly neutralizing antibodies against Env and an anti-VSV $G_{IN}$ antibody (VI10). The vector VSV-MGP-$G_{CT1}$ expresses an Env trimer that has been modified by introduction of Cys residues intended to form disulphide linkages between gp41 and gp120 subunits.

Figure 32:
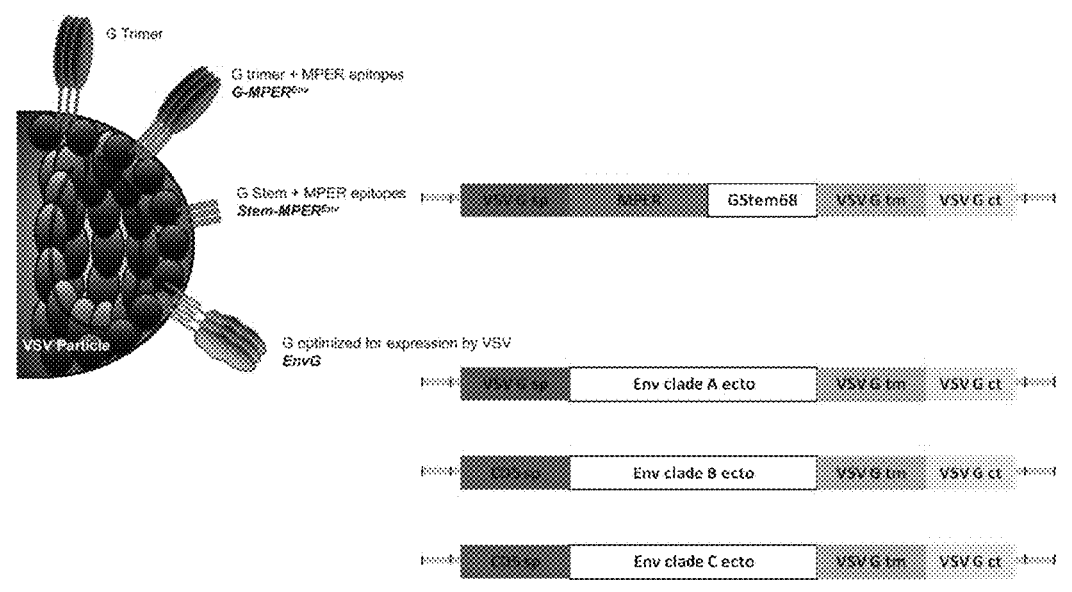

FIG. 32 depicts a design of the Env immunogens for display in the VSV particle. The inserts include the VSV (purple) or CD5 (red) secretion signals, Env ectodomain (clades A, B or C), or Env MPER region (green) plus Transmembrane (light blue) and C tail domains (yellow) of VSV G.

Figure 33:
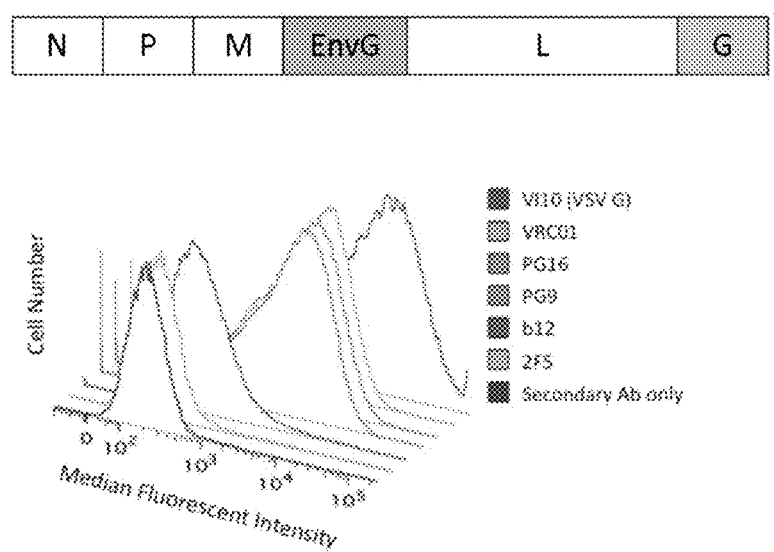

FIG. 33 depicts Env (clade C) 16055 and VSV G proteins are expressed on the cell surface of VSV-Env-G6 infected cells. This VSV-EnvG-G6 construct carries a fusion of the CD5 leader peptide to the Env Clade C protein ectodomain and VSV G transmembrane and C-tail domains. Vero cells infected with VSV-Env (clade C)-G6 vector were stained with human anti-HIV Env monoclonal antibodies VRC01, PG9, PG16, b12, 2F5, and an antibody against VSV $G_{IN}$ (VI10). Fluorescence was acquired on a modified BD LSR II flow cytometer.

Figure 34:
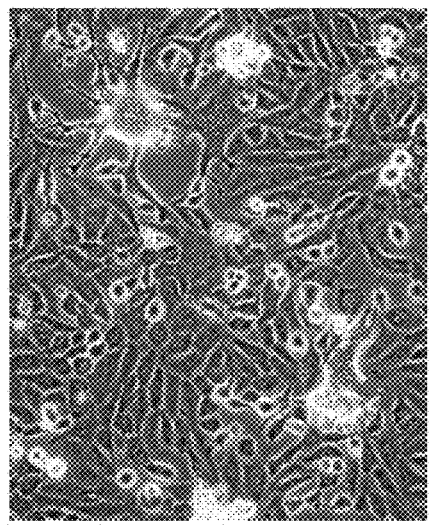

FIG. 34 depicts rVSV-EnvG (cladeC) 16055-G6 expresses both functional EnvG and VSV G proteins. This vector could use either EnvG or G to infect susceptible cell substrate. Functional VSV G was confirmed by successful viral propagation in Vero cells. For virus infection through EnvG protein, a GHOST cell line that expresses CCR5 and CD4 receptors was used as substrate. GHOST cells can be infected with these vectors via VSV G and/or EnvG proteins. To corroborate the EnvG was functional, the virus was incubated prior to infection with anti-VSV G serum, for 30 minutes at 37° C., to block VSV G binding to cell receptor. Vector plus antibody was then used for infection of CD4/CCR5+ GHOST cells. Syncytia formation, characteristic of Env mediated fusion, showed up 24 hours after infection. The figure shows a monolayer of GHOST cells 24 hours after infection with VSV EnvG 16055-G6 blocked with anti-VSV G serum. Red arrows point to syncitia.

Figure 35:
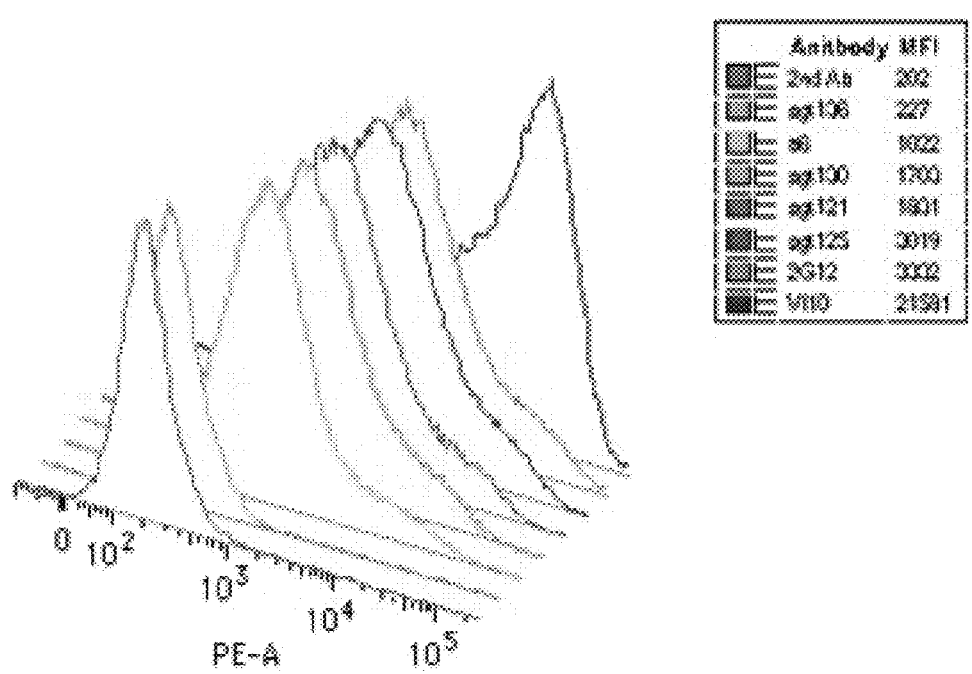

FIG. 35 depicts EnvG (clade A) BG505 and VSV G proteins are expressed on the cell surface of VSV-EnvG-G6 infected cells. This VSV-EnvG-G6 construct carries a fusion of the VSV leader peptide, Env Clade A protein ectodomain and VSV G transmembrane and C-tail domains. Vero cells infected with VSV-EnvG (clade A)-G6 vector were stained with human anti-HIV Env monoclonal antibodies PGT121, PGT125, PGT130, PGT136, B6 and 2G5, and an antibody against VSV $G_{IN}$ (VI10). Fluorescence was acquired on a modified BD LSR II flow cytometer.

FIG. 36 depicts flow cytometry study of cell surface expression of MPER and VSV-G. Vero cells were infected with rVSV-GS68MPER-G6 vector and stained with monoclonal antibodies. MPER epitope is recognized by human monoclonal antibodies 2F5 and 4E10. VSV G is recognized by mouse monoclonal antibody Vi10.

Figure 37:
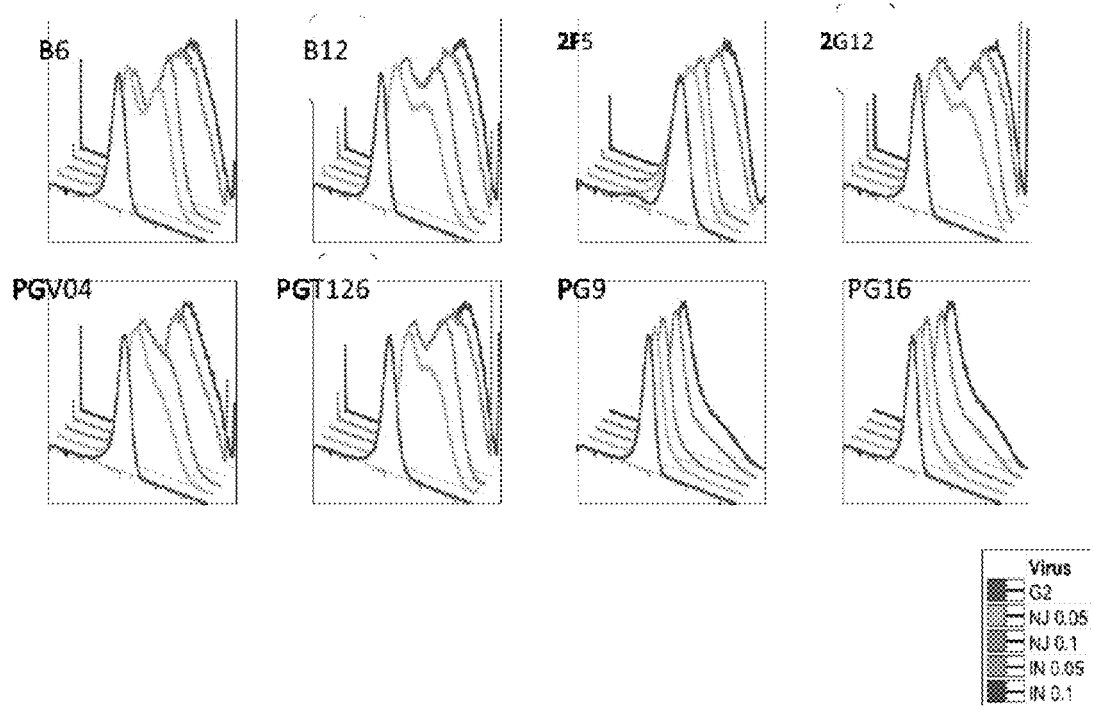

FIG. 37 depicts an Env (clade B) JRF-L protein is expressed on the surface of infected cells. Flow cytometry analysis of Vero cells infected with JRFL-$G_{IN}$ and JRFL-$G_{NJ}$ using a panel of broadly neutralizing antibodies. Vero cells were infected with either VSV-EnvG-$G_{NJ}$ or $G_{IN}$ at different multiplicity of infection (0.1 and 0.05). After 16 hrs, cells were collected, stained with a panel of broadly neutralizing antibodies specific for HIV Env. G2, VSV control virus. NJ, VSV-EnvG-$G_{NJ}$. IN, VSV-EnvG_$G_{IN}$.

Figure 38:
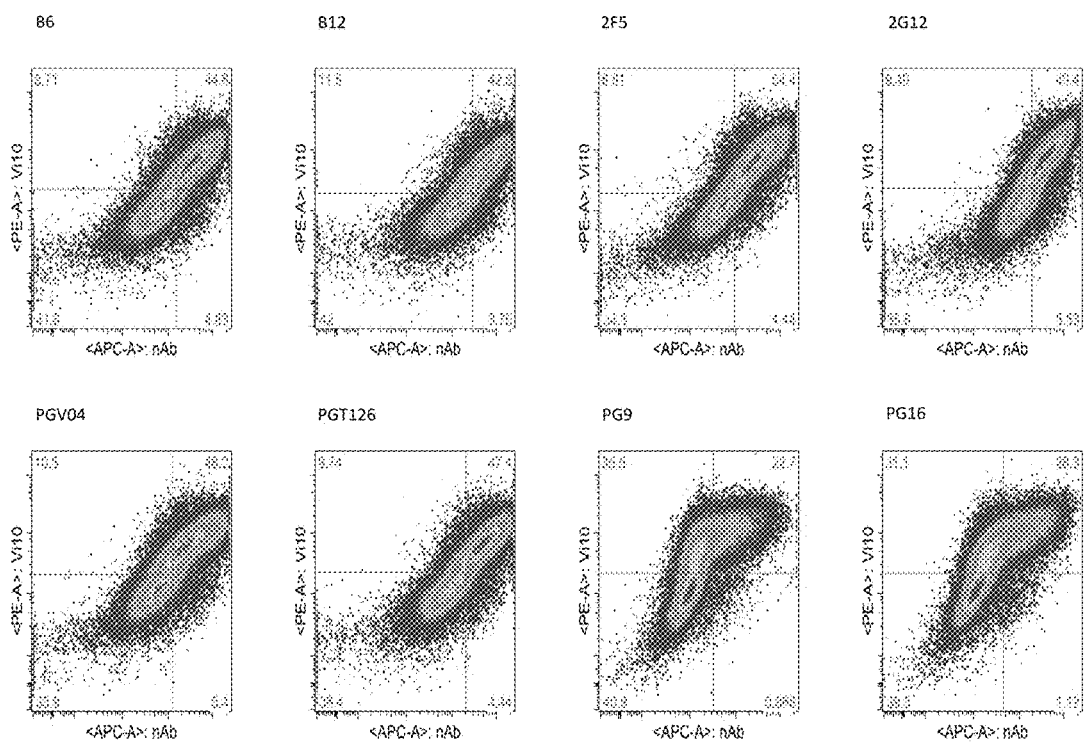

FIG. 38 depicts co-expression of G and EnvG on the surface of infected cells. Flow cytometry analysis of Vero cells infected with VSV EnvG (clade B) JRFL-$G_{IN}$ using a panel of broadly neutralizing antibodies against Env and an anti-VSV $G_{IN}$ antibody (VI10). The data shows that 60% of the infected cells can be recognized by the VSV-G antibody, and at least 40% can be also recognized by the anti-Env monoclonal antibodies.

Figure 39:
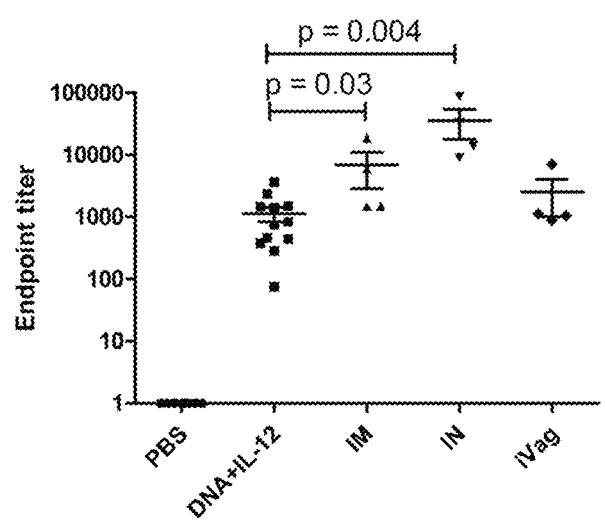

FIG. 39 depicts immune responses elicited in mice by plasmid DNA prime and VSV-EnvG JRFL-$G_6$ vector boost. VSV-EnvG JRFL-G6 vector boosts antibody responses in serum of mice immunized with pDNA-EnvG-JRFL+plasmid IL12 by electroporation (EP). Balb/c mice received the JRFL pDNA+pIL-12 by EP at weeks 0 and 3, and a boost with VSV-EnvG G6 vectors at week 6. Anti-Env serum antibody titers were determined one week after boost. A statistically significant increase in antibodies was observed after VSV boost by intramuscular (1M, p=0.03) and intranasal (IN, p=0.004) routes.

FIGS. 40A-D depict Env specific CD4+ T cell responses in spleens and lungs in mice after VSV-EnvG JRFL-G6 vector boost. Balb/c mice received the pDNA JRFL+ IL-12 EP at weeks 0 and 3, and a boost with VSV-EnvG JRFL G6 vector at week 6. Anti-Env cellular responses were analyzed two weeks after DNA prime and 2 weeks after VSV boost. Cells were stained with LIVE/DEAD Fixable Violet Dead Cell Stain (Molecular Probes), CD3, CD4, IFN-g, IL-2, TNF (BD Biosciences), and CD8 (BioLegend). Stained cells were resuspended in 0.5% paraformaldehyde before being acquired on a modified BD LSR II flow cytometer. A marked increase in immune responses can be observed two weeks after immunization by intramuscular and intranasal routes. A. and B. cells isolated from spleens. C. and D. cells isolated from lungs.

DETAILED DESCRIPTION

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab')$_2$, Fv and scFv which are capable of binding the epitope determinant. These antibody fragments retain some ability to selectively bind with its antigen or receptor and include, for example:

(i) Fab, the fragment which contains a monovalent antigen-binding fragment of an antibody molecule can be produced by digestion of whole antibody with the enzyme papain to yield an intact light chain and a portion of one heavy chain;

(ii) Fab', the fragment of an antibody molecule can be obtained by treating whole antibody with pepsin, followed by reduction, to yield an intact light chain and a portion of the 20 heavy chain; two Fab' fragments are obtained per antibody molecule;

(iii) F(ab')$_2$, the fragment of the antibody that can be obtained by treating whole antibody with the enzyme pepsin without subsequent reduction; F(ab')$_2$ is a dimer of two Fab' fragments held together by two disulfide bonds;

(iv) scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87:

2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vesicular stomatitis virus (VSV) vector expressing a foreign epitope. Advantageously, the epitope is an HIV epitope. Any HIV epitope may be expressed in a VSV vector. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220,554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179;

6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707 5,698,178; 5,688,914; 5,686,078; 5,681,831; 5,679,784; 5,674,984; 5,672,472; 5,667,964; 5,667,783; 5,665,536; 5,665,355;
5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852, 5,268,265; 5,264,356; 5,264,342; 5,260,308; 5,256,767; 5,256,561; 5,252,556; 5,230,998; 5,230,887; 5,227,159; 5,225,347; 5,221,610, 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

Advantageously, the HIV epitope may be an Env precursor or gp160 epitope. The Env precursor or gp160 epitope may be recognized by antibodies PG9, PG16, 2G12, b12, 2F5, 4E10, Z13, or other broad potent neutralizing antibodies.

In another embodiment, HIV, or immunogenic fragments thereof, may be utilized as the HIV epitope. For example, the HIV nucleotides of U.S. Pat. Nos. 7,393,949, 7,374,877 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The present invention relates to recombinant vesicular stomatitis (VSV) vectors, however, other vectors may be contemplated in other embodiments of the invention such as, but not limited to, prime boost administration which may comprise administration of a recombinant VSV vector in combination with another recombinant vector expressing one or more HIV epitopes.

VSV is a very practical, safe, and immunogenic vector for conducting animal studies, and an attractive candidate for developing vaccines for use in humans. VSV is a member of the Rhabdoviridae family of enveloped viruses containing a nonsegmented, negative-sense RNA genome. The genome is composed of 5 genes arranged sequentially 3'-N-P-M-G-L-5', each encoding a polypeptide found in mature virions. Notably, the surface glycoprotein G is a transmembrane polypeptide that is present in the viral envelope as a homotrimer, and like Env, it mediates cell attachment and infection.

Figure 22:
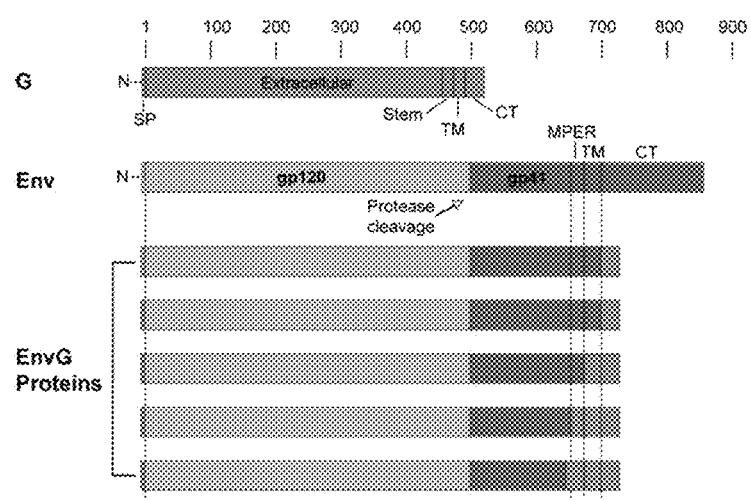
FIG. 22 depicts various VSV G-HIV Env chimeras. The VSV glycoprotein G is shown at the top with features labeled including the signal peptide (SP), the soluble extracellular domain, the Stem, transmembrane (TM) segment and cytoplasmic tail (CT). The HIV-1 Envelope (Env) protein, illustrated below G, is proteolytically processed into the extracellular gp120 and the gp41 domains, the latter containing the MPER, TM segment and CT domains. Various chimeric EnvG proteins are shown at the bottom. Transition points between HIV gp41 and VSV G are located i) before the CT, ii) before the TM domain, iii) before the MPER, or iv) N-terminal to the complete VSV G-Stem. Translocation of the protein into the lumen of the endoplasmic reticulum can be driven by either the Env or the G signal peptide, although the efficiency and destination vary with the two signals. The ruler at the top denotes the number of amino acid residues.
Figure 23:
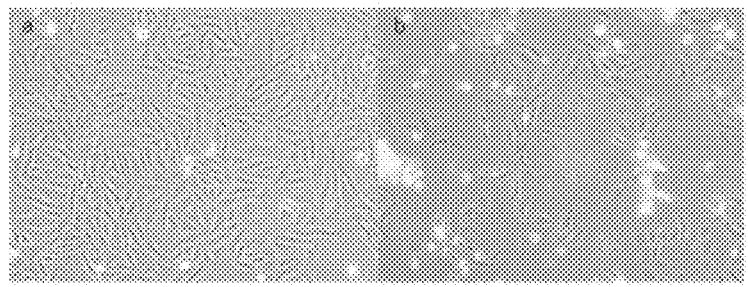
FIG. 23 depicts infectivity of rVSV-EnvG. a, Uninfected GHOST cells (expressing the HIV co-receptors CD4 and CCR5; Cecilia D., et al J. Virol. 1998 September; 7:6988-96) near full confluency. b, GHOST cells infected with rVSV-EnvG virus at 48 hours post-infection. The cytopathic effect (CPE) is clearly visible.

In a first advantageous embodiment, the VSV G is replaced by HIV Env or fragments thereof. The latter will generate chimeric EnvG proteins (see, e.g. FIG. 22).

Figure 5:
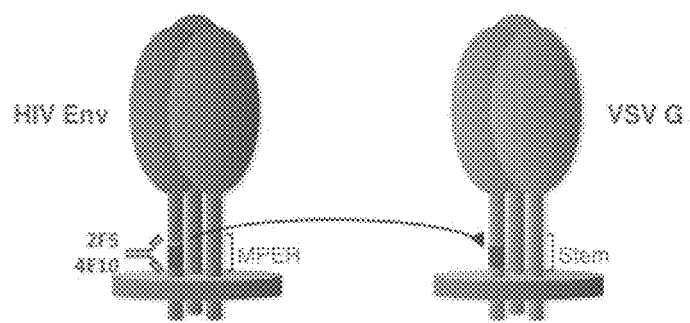
FIG. 5 depicts insertion of the HIV gp41-derived 2F5 and/or 4E10 epitope into the 'stem' region of VSV G, which shares sequence similarities with the gp41 MPER.

In a second advantageous embodiment, VSV G is a carrier or scaffold advantageously for Env MPER epitopes, however, VSV G as a carrier or scaffold may be extended to any foreign epitope (see, e.g., FIGS. 5-7).

Figures 18A, 18B:
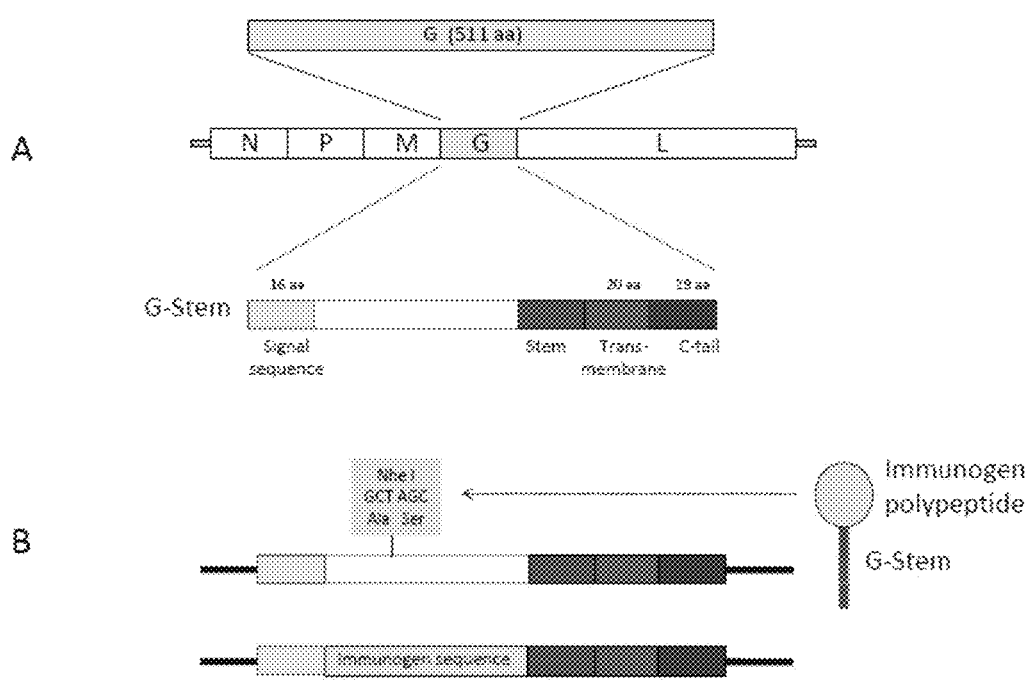
FIGS. 18A and 18B depict a VSV G-Stem platform for expression of fusion proteins. A. Schematic illustration of the VSV genome, the G gene, and the primary structures of the G and G-Stem proteins. B. Foreign gene sequences are fused to the G-Stem via a NheI restriction site, which facilitates incorporation of immunogen coding sequences.

In a third advantageous embodiment, Env MPER epitopes are fused to the VSV G-Stem molecule, however, any foreign epitope may be fused to the VSV G-Stem molecule (see, e.g., FIGS. 18-19).

In a fourth embodiment, the invention pertains to the evolutionary potential of RNA viruses. Such viruses include but are not limited to: VSV, Measles virus, Canine distemper virus, Parainfluenza viruses, Sendai virus, Newcastle disease virus, Venezuelan equine encephalitis virus, Sindbis virus, Semliki Forrest virus etc. Pertaining to the evolutionary potential of VSV, in the first step of EnvG construction, a small panel of genes encoding different forms of EnvG molecules will be produced to determine which motifs from G will optimize expression. Replication-competent 'chimeric' VSV-HIV viruses that lack the capacity to encode wild-type G and are dependent on EnvG for infection and propagation, which are then utilized to direct the evolution of new EnvG molecules that are expressed and incorporated into the virus with greater efficiency.

Figure 24:
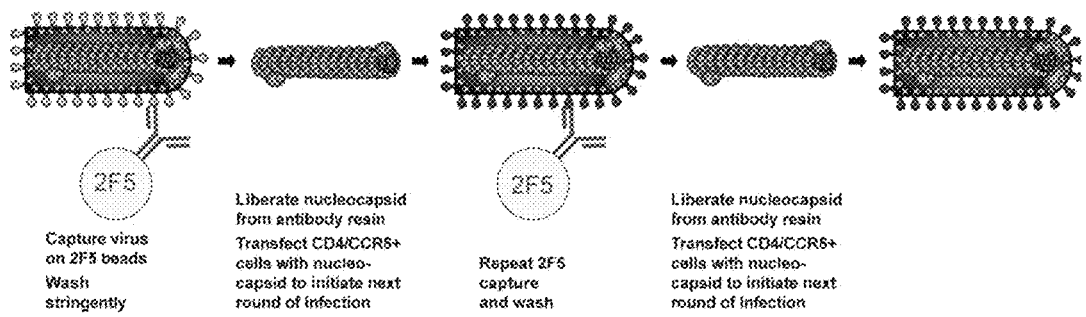
FIG. 24 depicts evolution of Env or EnvG proteins expressed by recombinant VSV. Recombinant VSV encoding a chimeric EnvG molecule are subjected to serial passage and selective pressure. Virus particles that bind with high avidity to 2F5 antibody, for example, are isolated after stringent washing of the antibody beads. Infectious nucleocapsid is liberated from the antibody beads and transfected into CD4/CCR5-positive cells, which initiates a new round of infection. The new generation of recombinant virus undergoes further rounds of selection with increased stringency, which enrich new variants of recombinant viruses that may have improved immunogenic properties.
Figure 26:
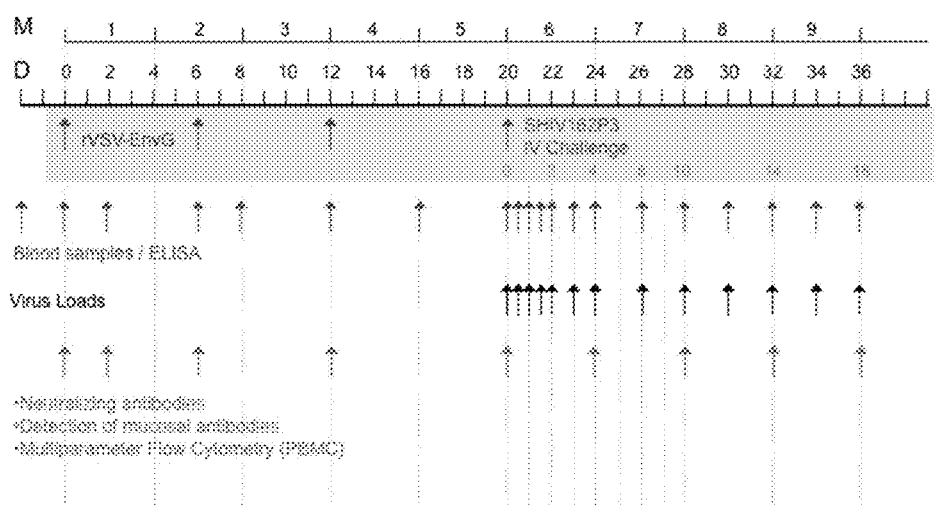
FIG. 26 depicts a plan for vaccination, sampling, and SHIV Challenge. rVSV vaccine candidates are administered 3 times at 6-week intervals after which IV SHIV 162P3 challenge is conducted using a challenge stock obtained from the NIH AIDS Research & Reference Reagent Program.

In a fifth embodiment, the invention pertains to application of selective pressure to enrich for molecules that are more immunogenic. The evolution process will occur primarily through nucleotide substitution, followed by selection using a broadly neutralizing antibody against HIV Env, e.g. 2F5 or 4E10, or a broad potent antibody specific for trimeric Env. Due to the nature of negative-strand virus replication, base changes are far more frequent than deletions or insertions, consequently the immunogen will evolve with amino acid substitutions. (see, e.g. FIG. 24)

The VSVs of U.S. Pat. Nos. 7,468,274; 7,419,829; 7,419, 674; 7,344,838; 7,332,316; 7,329,807; 7,323,337; 7,259, 015; 7,244,818; 7,226,786; 7,211,247; 7,202,079; 7,198, 793; 7,198,784; 7,153,510; 7,070,994; 6,969,598; 6,958, 226; RE38,824; PP15,957; 6,890,735; 6,887,377; 6,867, 326; 6,867,036; 6,858,205; 6,835,568; 6,830,892; 6,818, 209; 6,790,641; 6,787,520; 6,743,620; 6,740,764; 6,740, 635; 6,740,320; 6,682,907; 6,673,784; 6,673,572; 6,669, 936; 6,653,103; 6,607,912; 6,558,923; 6,555,107; 6,533, 855; 6,531,123; 6,506,604; 6,500,623; 6,497,873; 6,489, 142; 6,410,316; 6,410,313; 6,365,713; 6,348,312; 6,326, 487; 6,312,682; 6,303,331; 6,277,633; 6,207,455; 6,200, 811; 6,190,650; 6,171,862; 6,143,290; 6,133,027; 6,121, 434; 6,103,462; 6,069,134; 6,054,127; 6,034,073; 5,969, 211; 5,935,822; 5,888,727; 5,883,081; 5,876,727; 5,858, 740; 5,843,723; 5,834,256; 5,817,491; 5,792,604; 5,789, 229; 5,773,003; 5,763,406; 5,760,184; 5,750,396; 5,739, 018; 5,698,446; 5,686,279; 5,670,354; 5,540,923; 5,512, 421; 5,090,194; 4,939,176; 4,738,846; 4,622,292; 4,556,556 and 4,396,628 may be contemplated by the present invention.

The nucleotide sequences and vectors of the invention can be delivered to cells, for example if aim is to express and the HIV-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition which may comprise the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum*, *Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTAT-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD4OL (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin is combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulations can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

The prime-boost regimen can also include VSV vectors that derive their G protein or G/Stem protein from different serotype vesicular stomatitis viruses (Rose N F, Roberts A, Buonocore L, Rose J K. Glycoprotein exchange vectors based on vesicular stomatitis virus allow effective boosting and generation of neutralizing antibodies to a primary isolate of human immunodeficiency virus type 1. J. Virol. 2000 December; 74(23):10903-10). The VSV vectors used in these examples contain a G or G/Stem protein derived from the Indiana serotype of VSV. Vectors can also be constructed to express epiotpes in the context of G or G/Stem molecules derived from other VSV serotypes (i.e. vesicular stomatitis New Jersey virus or vesicular stomatitis Alagoas virus) or other vesiculoviruses (i.e. Chandipura virus, Cocal virus, Isfahan virus). Thus an epitope like the HIV MPER can be delivered in a prime in the context of an G or G/Stem molecule that is from the Indiana serotype and the immune system can be boosted with a vector that expresses epitopes in the context of second serotype like New Jersey. This circumvents anti-G immunity elicited by the prime, and helps focus the boost response against the foreign epitope.

A specific embodiment of the invention provides methods of inducing an immune response against HIV in a subject by administering an immunogenic composition of the invention, preferably which may comprise an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA-.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject may comprise administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

It is to be understood and expected that variations in the principles of invention as described above may be made by one skilled in the art and it is intended that such modifica-

EXAMPLES

Example 1: Insertion of the HIV-1 gp41 Epitopes 2F5 and 4E10 into the Membrane-Proximal Region of the Vesicular Stomatitis Virus Glycoprotein The membrane-proximal external region (MPER) of HIV-1 gp41, which is recognized by the broadly neutralizing monoclonal antibodies 2F5 and 4E10, is an important target for an HIV vaccine. However, efforts to mimic the 2F5 and 4E10 epitopes outside the context 30 of the gp41 MPER have had minimal success so far. In this study, Applicants used the envelope glycoprotein G of Vesicular Stomatitis Virus (VSV) as a scaffold. VSV G, which forms homotrimeric spikes on the viral surface, is responsible for binding of the virus to cells and promotes fusion of the viral and cellular membranes. The "stem" region of VSV G, which lies immediately N-terminal of its single transmembrane segment, shares sequence similarities with the gp41 MPER. Applicants inserted the gp41 sequences corresponding to the 2F5 and 4E10 neutralizing epitopes into the stem region of VSV G and evaluated the function and antibody reactivity of the chimeric polypeptides. VSV-G-2F5 and VSV-G-4E10 formed trimers and were transported to the cell surface, where they were detected by the 2F5 and 4E10 monoclonal antibodies, respectively. Reporter lentiviruses pseudotyped with VSV G-2F5 or VSV-G-4E10 were infectious, and they were efficiently neutralized by the 2F5 or 4E10 monoclonal antibodies. Recombinant VSV containing G-2F5, G-4E10 or G-2F5-4E10 on the viral surface was infectious, replication-competent, and sensitive to neutralization by the 2F5 or 4E10 monoclonal antibodies. Applicants are currently determining if the recombinant VSVs encoding MPER epitopes elicit neutralizing antibodies specific for the HIV gp41 epitopes in a small animal model. Taken together, Applicants' approach represents a novel strategy to develop a vaccine that induces a humoral immune response against HIV.

Example 2: Using VSV Vectors to Display and Evolve Novel HIV Envelope Immunogens The goal of this Example is to design and develop novel HIV-1 envelope protein (Env) immunogens capable of eliciting broadly protective neutralizing antibody responses for use as vaccine candidates. Applicants take advantage of the unique biological properties of vesicular stomatitis virus (VSV) as vaccine delivery vehicle to present and effectively deliver HIV Env immunogens. In addition, Applicants use the high evolutionary potential of VSV to biologically derive unique mutant HIV Envs with enhanced immunogenicity. Novel candidates are used to vaccinate rabbits to determine their capacity to elicit antibodies with enhanced HIV neutralizing activity, and those VSV-vectored vaccines that evoke responses with increased breadth of neutralization are tested in macaques. Applicants achieve these goals by completing the Specific Aims below:

1. Vaccine Platform 1: Optimize HIV Env (derived from $SHIV_{SF162P3}$) for expression as functional stable trimers on the surface of VSV particles, and produce 'chimeric viruses', in which the gene encoding the VSV surface glycoprotein (G) are functionally replaced by HIV Env. Env modifications described below are investigated to identify the optimal form for expressing abundant functional trimers on VSV particles that specifically direct infection of cells expressing the CD4 and CCR5 coreceptors (CD4/CCR5$^+$ cells). Additionally, Applicants take advantage of the innate ability of VSV to rapidly accrue adaptive mutations to further optimize expression of functional Env trimers by subjecting replication-competent VSV-Env chimeric viruses to serial passage on CD4/CCR5$^+$ cell lines to biologically select for Env mutations that improve replicative fitness. Moreover, to develop additional novel Env immunogens, methods to apply selective pressure during serial passage are developed using the broadly neutralizing antibodies against Env (e.g. monoclonal antibodies 2F5, 4E10, 2G12, b12, PG9, PG16 and other antibodies, including broad potent neutralizing trimer-specific antibodies).

2. Vaccine Platform 2: Produce recombinant VSV (rVSV) vectors that encode modified forms of VSV G, which harbor epitopes from the HIV Env membrane proximal external region (MPER). This takes advantage of several G protein properties including: i) it is a glycosylated transmembrane protein abundantly expressed on the VSV particle; ii) it is a potent immunogen; iii) it contains a hydrophobic membrane-proximal region that resembles the Env MPER, and iv) G trimerizes and provides a platform for multimeric configurations of MPER epitopes. Although several domains in G are tested as sites for insertion of MPER sequences, Applicants focus on the membrane proximal region of G, which provides a similar membrane-associated environment for the most authentic presentation of MPER epitopes. Env MPER insertions that do not abolish the function of VSV G are delivered using VSV vectors and advanced into rabbit immunogenicity studies. Additionally, VSV encoding G-MPER hybrids are subjected to serial passage to determine whether virus expressing a fitness advantage emerges with unique mutations that affect the MPER epitope configuration. Moreover, serial passage also are conducted using conditions that select virus expressing G-MPER proteins that bind with high avidity to the 2F5 and 4E10 mAbs to derive unique immunogens.

3. Vaccine Platform 3: An N-terminally truncated form of VSV G (called G/Stem) are used to present Env epitope sequences on the surface of VSV particles. The G/Stem molecule contains the cytoplasmic tail (CT) and transmembrane (TM) spanning domains of G as well as a short 16- to 68-amino acid membrane proximal extracellular polypeptide (the Stem) to which HIV Env epitopes are appended. Several forms of G/Stem, which vary in length and amino acid sequence, are investigated to determine the optimal form for display of MPER epitopes on the surface of VSV particles and the plasma membrane of infected cells. VSV encoding G/Stem fusion proteins can be propagated using G trans-complementation or by generating recombinant virus that contains a functional G gene in addition to the G/Stem coding sequence. Novel G/Stem-MPER molecules are evolved by serial passage under conditions that select for vectors encoding mutant molecules that bind to the 2F5 and 4E10 mAbs with high affinity.

4. In Vivo Studies: After validating their in vitro properties, promising vaccine candidates developed in Aims 1-3 are evaluated by vaccinating rabbits. Enzyme-linked immunosorbent assays (ELISAs) are conducted first to screen for serum antibodies that react with HIV Env, and those immune sera that contain significant titers are evaluated in HIV neutralization assays using virus-like particles pseudotyped with Env from various HIV strains. The top rVSV-Env vaccine candidates that evoke production of broadly neutralizing antibodies in vaccinated rabbits are advanced into nonhuman primate studies. Rhesus macaques are vaccinated to determine whether immunization protects macaques from subsequent intravenous challenge with the SIV-HIV chimeric virus SHIV$_{SF162P3}$, which expresses an HIV envelope protein.

Example 3: Optimization of Immunogen Presentation by G-Stem Vectors

To develop a platform that can be used to display immunogens on the surface of virus particles or infected cells, Applicants have engineered vesicular stomatitis virus (VSV) vectors to encode a truncated form of the viral transmembrane glycoprotein protein (G) that can be modified to express foreign epitopes anchored to virus envelop or cell membrane. The truncated form of G, called G-Stem (FIG. 18A), retains amino acid sequences that are essential for directing insertion of the molecule into the membrane (the signal peptide), anchoring the protein in the viral envelop or cellular lipid bilayer (the transmembrane domain; TM), and promoting incorporation into the budding viral particle (C-terminal domain). Additionally, a small membrane proximal region of the external domain of G (the Stem) is retained in most constructs because it provides a short stalk on which to append epitopes (FIG. 18B), and importantly, sequences in the Stem are known to promote efficient assembly of VSV particles [Robison & Whitt, J Virol 2000; 74:2239-2246].

Figures 19A, 19B, 19C:
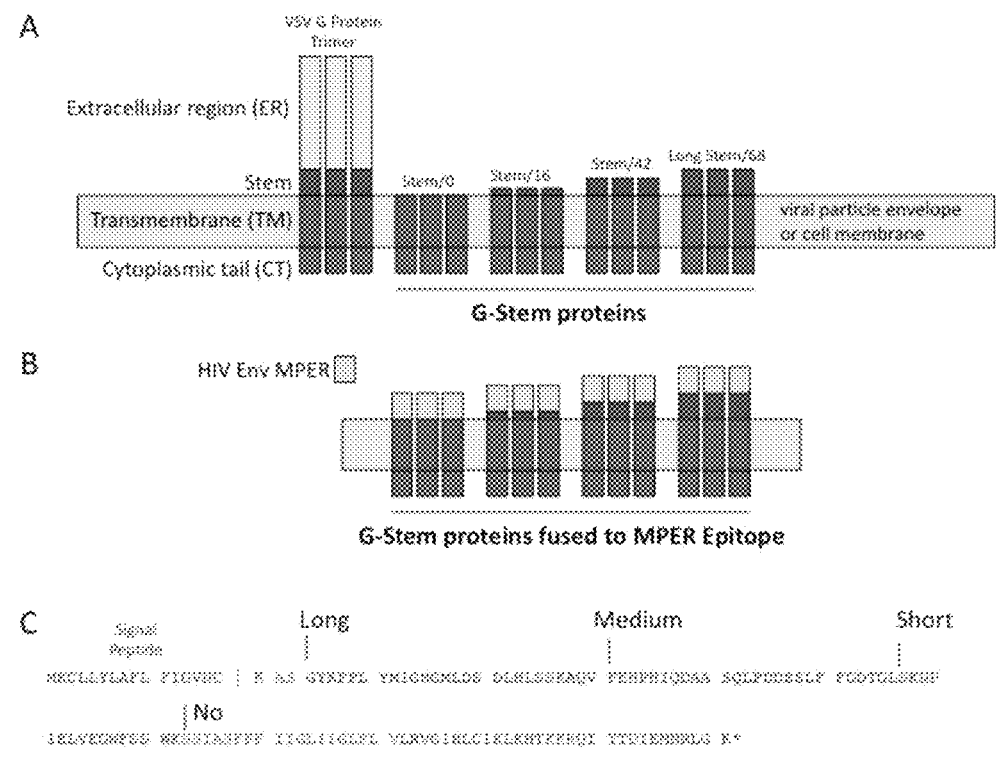

Because the Stem domain plays at least two significant roles in Applicants' epitope display vectors—it serves as the platform on which epitopes are attached and displayed, and it plays a role in VSV maturation—Applicants anticipated that it might be necessary to empirically determine the optimal Stem sequence needed for expression and membrane incorporation of G-Stem-Epitope fusion proteins. Applicants tested this assumption by constructing 4 different G-Stem fusion proteins that contained the HIV Env membrane proximal external region (MPER) [Montero et al., Microbiol Mol Biol Rev 2008; 72:54-84] fused to Stem domains that were 68, 42, 16 or 0 amino acids in length, referred to as long stem (LS), medium stem (MS), short stem (SS), and no stem (NS), respectively (FIGS. 19A-C).

Figure 20:
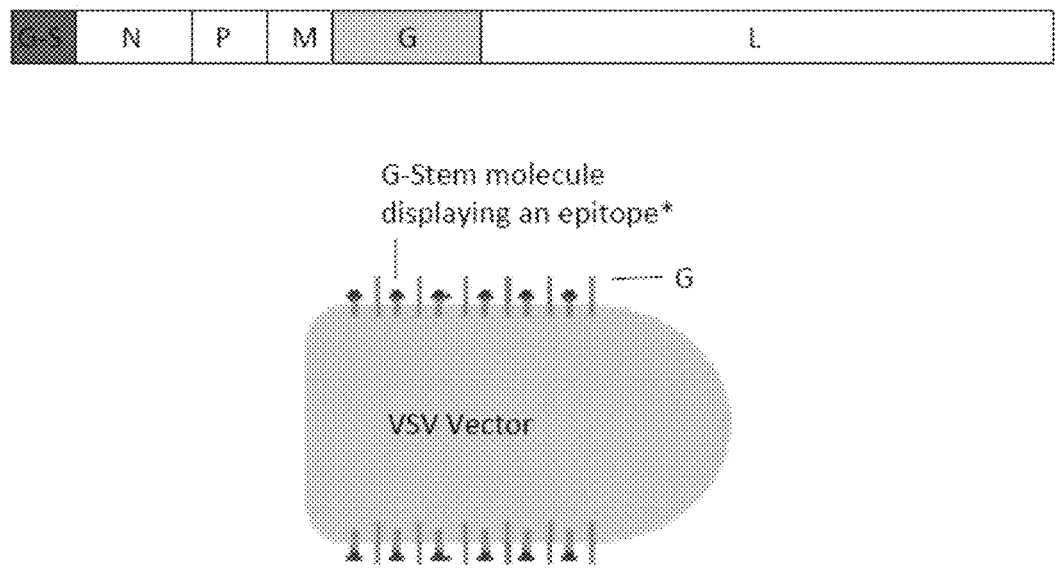
FIG. 20 depicts VSV Vector Design. The gene encoding G-Stem variants was inserted into the VSV genome upstream of the N protein near the 3' end. In addition, the full-length G protein is present in the genome. Upon expression, both the G-Stem and full-length G will be incorporated into virus particles as illustrated below the vector genome map.

The 4 G-Stem-MPER (GS-MPER) molecules were expressed using a novel replication-competent VSV vector that retains a functional G protein and expresses the GS-MPER fusion proteins from an added transcription unit inserted in the highly-transcribed promoter proximal position in the viral genome (FIG. 20). Consequently, the MPER expression vectors express GS-MPER fusion proteins as well as wild-type G protein. Expression of native G protein confers a replication-competent phenotype of these recombinant viruses, and importantly, this also means that infected cells will produce wild-type G and GS-MPER proteins and that both proteins can be inserted into cell membrane and viral envelop (right side of FIG. 20B).

Figure 21:
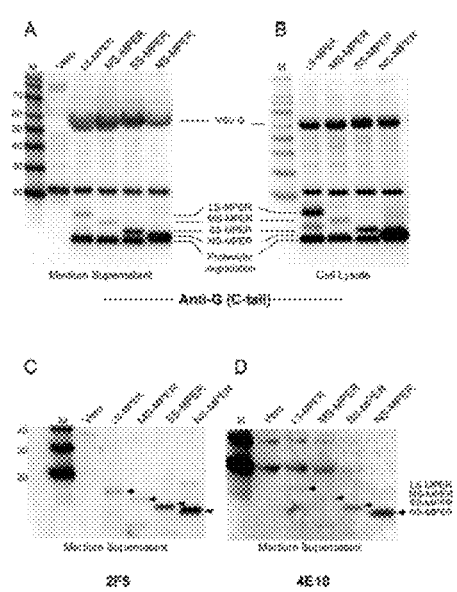
FIGS. 21A-21D depict analysis of G-Stem-MPER Expression. A. Western Blot analysis of rVSV containing the G-Stem-MPER variants (rVSV-GS-MPER) from the supernatant of infected cells using an anti-VSV-G antibody that reacts with the cytoplasmic tail. LS, long stem; MS, medium stem; SS, short stem; NS, no stem. B. Western Blot analysis of rVSV-GS-MPER from infected cells using an anti-VSV-G antibody. C. Western Blot analysis of rVSV-GS-MPER with the 2F5 antibody. D. Western Blot analysis of rVSV-GS-MPER with the 4E10 antibody.

After the recombinant VSV-G-Stem-MPER vectors were constructed, they were used to infect Vero cells and assess expression of the GS-MPER fusion proteins and determine their relative abundance in virus particles (FIG. 21). FIG. 21 shows a Western blot that was used to analyze G and G-Stem-MPER proteins found in the medium supernatant of infected cells. The source of G and GS MPER fusion proteins in the supernatant primarily should be virus that has budded out of infected cells; therefore, the proteins visualized in Panel A provide an estimate of the relative G and GS-MPER abundance in progeny virus particles. The blot in Panel A was reacted with antibody that recognizes the C-terminus of VSV G, which is present on both the native G protein the G-Stem-MPER molecules. The results indicate that NS-MPER and SS-MPER are present at higher levels in the virus particle than MS-MPER or LS-MPER, and that none of the G-Stem-MPERs are as abundant as the native G protein. It is important to note that a proteolytic fragment of G comigrates with the NS-MPER at the top of the gel (Lane 6) making it difficult to estimate its abundance. The relative amount of the 4 MPER-containing molecules is more clearly shown in Panels C and D where the GS-MPER proteins are reacted with MPER-Specific monoclonal antibodies 2F5 and 4E10. In Panel C for example, the relative amounts of NS-MPER (Lane 6) and SS-MPER (Lane 5) are clearly greater than MS- and LS-MPER (Lanes 3 and 4) in virus particles found in the supernatant. It is worth noting that the LS-MPER molecule is expressed at relatively high levels in infected cells as shown in Panel B (Lane 2) suggesting that this form of G-Stem-MPER is expressed but not efficiently incorporated into virus particles. The MS-MPER protein is evident in the infected cells (Panel B, Lane 3) but at low levels indicating that it is expressed poorly or it is unstable compared to the other GS-MPERS. Finally, it is notable that the NS-MPER protein, which lacks the Stem completely, seems to be incorporated at the highest levels of all of the G-Stem-MPERs (FIGS. 21C and D, Lanes 5 and 6). This finding seems to be contrary to the known role of Stem in virus particle maturation [Robison & Whitt, J Virol 2000; 74:2239-2246], but it is consistent with Applicants' results that show that the MPER and smaller peptides from the MPER regions can functionally substitute for the Stem (see, e.g. FIG. 14).

Taken together, these results show that achieving significant expression of G-Stem fusion proteins in infected cells and on virus particles requires optimization of the Stem domain. Applicants' finding that the NS Stem domain is perhaps optimal for expression of HIV MPER probably reflects the fact that the MPER has Stem-like properties. Other antigens expressed as G-Stem-antigen fusions may require different lengths of Stem to be incorporated efficiently into cellular or viral membranes.

Figures 1A, 1B:
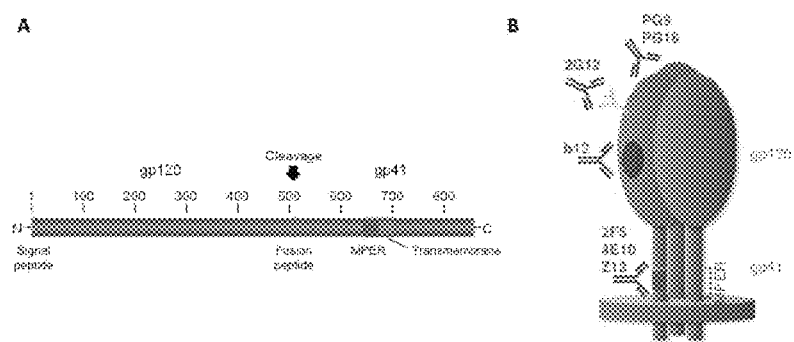
FIGS. 1A and 1B depict the HIV-1 envelope protein. A. Illustration of the gp160 precursor, which is post-translationally cleaved into the gp120 and gp41 subunits. The locations of the signal and fusion peptides, the Membrane-Proximal External Region (MPER) and the transmembrane (TM) segment are indicated. The ruler denotes amino acid numbering. B. Broadly neutralizing antibodies directed against Env: PG9 and PG16 interacts with conserved residues in the V2 and V3 loops and present an accessible target on gp120; 2G12 binds to oligosaccharides at the tip of gp120; b12 interacts with the CD4 binding site; 2F5 and 4E10 bind adjacent linear epitopes in the gp41 MPER.

Example 4: Insertion of the HIV-1 gp41 Epitopes 2F5 and 4E10 into the Membrane-Proximal Region of the Vesicular Stomatitis Virus Glycoprotein Broadly neutralizing antibodies against the HIV Env protein may bind epitopes on gp120 and gp41 (see, e.g., FIG. 1B). Such antibodies include, but are not limited to, PG9 and PG16 (which bind the base of V1/V☐☐2 loops and are trimer-specific), 2G12 (which binds carbohydrates), b12 (which binds the CD4-binding site) and 2F5, 4E10 and Z13 (which bind the membrane-proximal external region (MPER)).

Figure 2:
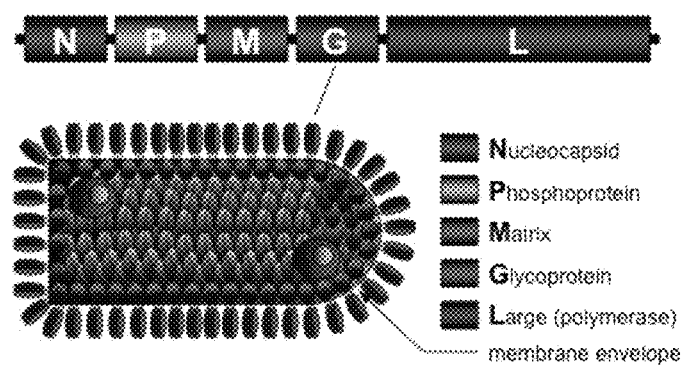
FIG. 2 depicts vesicular stomatitis virus. The negative-sense RNA genome (schematically depicted at the top) encodes five genes in the order 3'-N-P-M-G-L-5'. The surface of the virus particle (bottom) is decorated with approximately 1,200 copies of the glycoprotein (G), which is arranged as trimers. The matrix protein (M) lines the inner surface of the virus particle between the membrane and the nucleocapsid, probably making contact with G as well as the nucleocapsid (N) protein and giving the virus particles their characteristic rod- or bullet-shaped morphology. The polymerase (L) and phosphoprotein (P) are subunits of the RNA-dependent RNA polymerase complex.

A schematic of VSV is presented in FIG. 2. VSV is an enveloped, negative-strand RNA virus of the Rhabdoviridae family. VSV infects human cells, but is not pathogenic and propagates robustly in vitro and is a safe and immunogenic vector for conducting animal studies.

Figure 3:
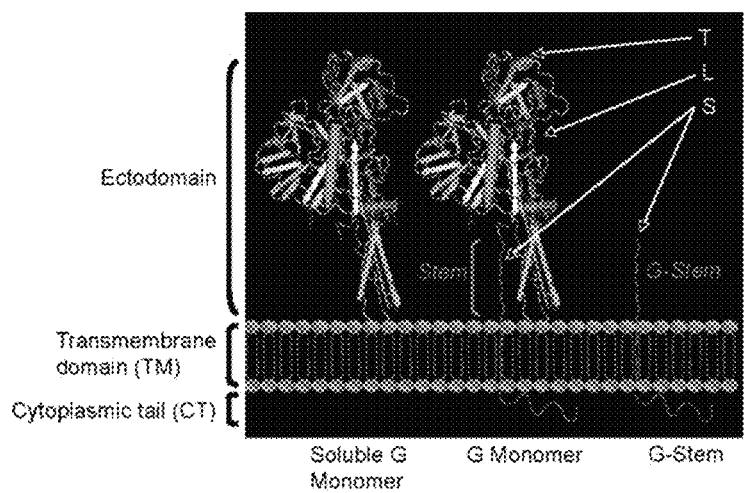
FIG. 3 depicts the VSV glycoprotein. The model on the left side is the soluble G ectodomain solved by Roche et al (Roche et al., Science 2007 315, 843-848), which is composed of a number of structural elements including an elongated β-sheet that contains the fusion peptide. In the middle portion of the Figure, a graphic approximation (in pink) of amino acid residues not included in the crystal structure was inserted, which includes the cytoplasmic tail (CT), the transmembrane (TM) domain, and the short membrane-proximal ectodomain (Stem). Three epitope insertion points were used for preliminary studies: an α-helix at the tip (T), a loop (L) on the side, and a region in the Stem (S). The Stem, together with the TM and CT domains, but without the remainder of the ectodomain, forms the G-Stem polypeptide, which is drawn at the right side of the Figure. The G-Stem protein can be incorporated into virions and can be used as a presentation platform for foreign epitopes.

A schematic of the VSV glycoprotein G is presented in FIG. 3. VSV glycoprotein G is a single envelope glycoprotein on the viral surface that forms trimers (ca. 1,200 molecules arranged as 400 trimers). VSV glycoprotein G mediates attachment, fusion, and entry of VSV into host cell, accepts insertion of short amino acid sequences at certain positions and has a membrane-proximal 'stem' region that shares similarities with the MPER of HIV-1 gp41.

Glycoprotein G is envisioned as an insertion site. In particular, epitope sequences, in particular HIV epitope sequences, more preferably HIV gp41 2F5 and 4E10 epitope sequences may be inserted into the stem region of VSV G. Replication-competent, recombinant VSV containing the modified G protein may be generated for use as an immunogen. FIG. 5 presents a schematic of insertion and substitution of HIV gp41 2F5 and 4E10 epitopes. FIG. 6 depicts insertion and substitution of the 2F5 and 4E10 epitopes. For an insertion, the 2F5 epitope and flanking residues was added to the VSV G stem region. For a substitution, residues in the VSV G stem region were replaced by the 2F5 and/or 4E10 epitopes. A summary of the VSV G constructs is presented in FIG. 7. The expression vector was pCI-Neo (deltaT7).

Figure 8:
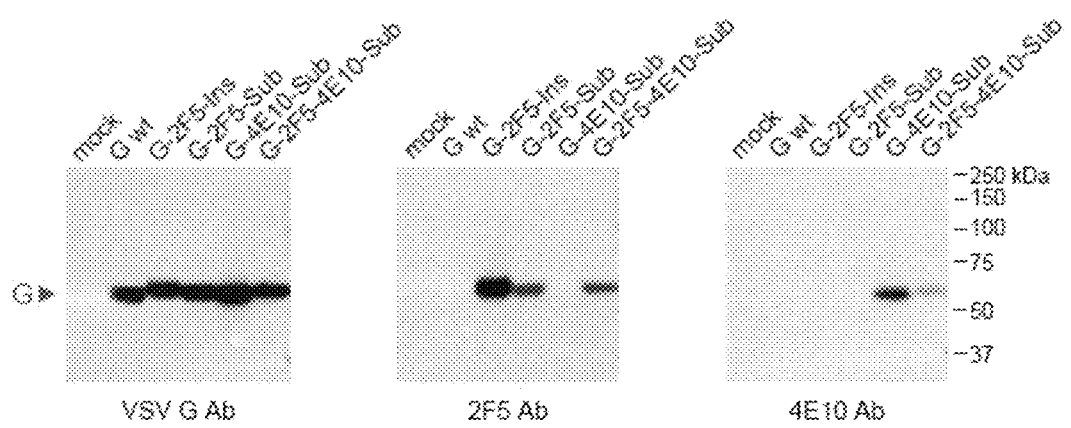
FIG. 8 depicts the expression and antibody detection of the VSV G constructs. Western blot using VSV-G, 2F5 and 4E10 antibodies to detect the G protein in lysates from 293T cells transfected with plasmids coding for unmodified VSV G, VSV G-2F5-Ins, VSV G-2F5-Sub, VSV G-4E10-Sub, or VSV G-2F5-4E10-Sub. Mock denotes a transfection with an "empty" plasmid vector. The antibody used for detection is shown under each panel. Molecular weight standards are indicated on the right of each gel.

A Western blot demonstrating the expression and antibody recognition of VSV G proteins expressed from plasmid DNA constructs is presented in FIG. 8. VSV constructs were expressed transiently in 293T cells and the Western blot was performed with lysates (2% CHAPS). The Western blot showed that the stem region of VSV G tolerated the insertion of the 2F5 and/or 4E10 epitope, and that modified VSV G constructs were detected by the 2F5 and 4E10 antibodies.

Figure 9:
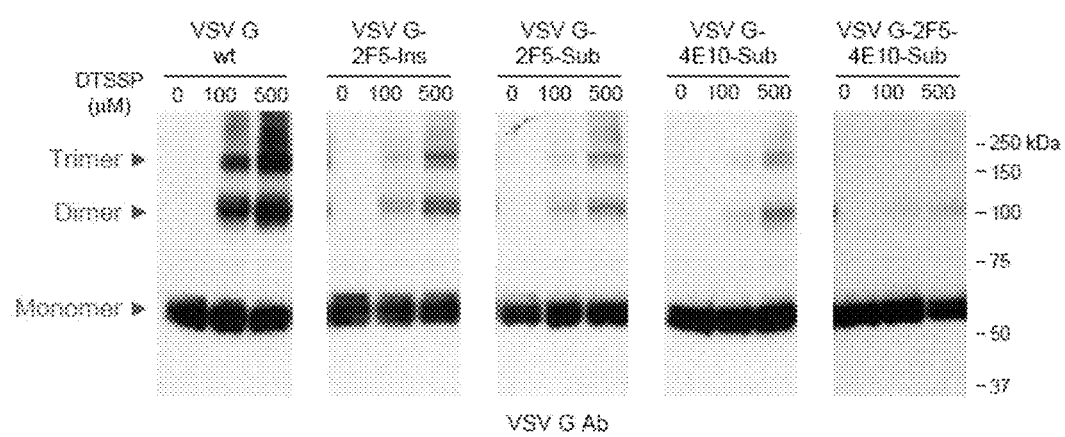
FIG. 9 depicts the trimerization of the VSV G constructs. Western blot using VSV-G antibody to detect oligomeric G protein on the surface of 293T cells transfected with VSV G constructs, followed by incubation with the chemical cross-linker 3,3'-Dithiobis-[sulfosuccinimidylpropionate] (DTSSP) at various concentrations as indicated above each lane. Monomeric, dimeric and trimeric VSV G forms are detected.

Trimerization of VSV G on the cell surface is presented in FIG. 9. The VSV G plasmid DNA constructs were expressed in 293T cells, chemical crosslinking was performed with DTSSP (3,3'-Dithiobis-[sulfosuccinimidyl-propionate]) on intact cells and western blot with cell lysates was performed. As shown in FIG. 9, all VSV G variants form trimers on the surface of 293T cells.

Figure 10:
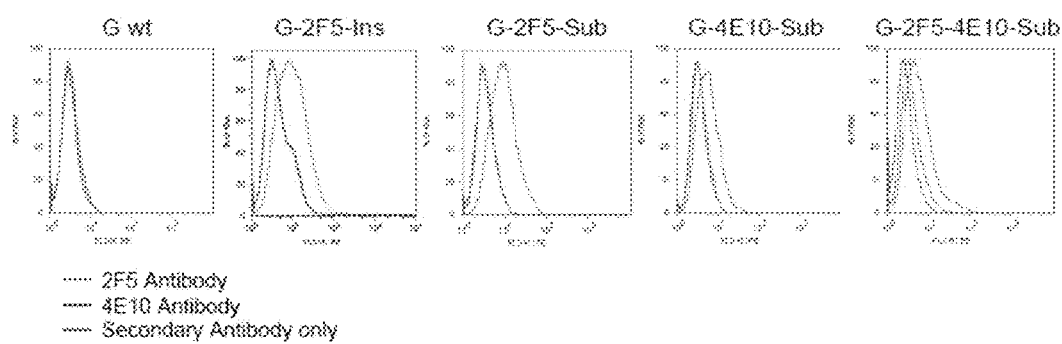
FIG. 10 depicts cell surface expression of VSV G constructs. 293T cells transfected with VSV G constructs were stained with an antibody specific for the ectodomain of VSV G, or with 2F5 or 4E10 antibodies, followed by analysis of the samples by flow cytometry.

Cell surface expression of VSV G constructs is presented in FIG. 10. The VSV G constructs were transiently expressed in 293T cells, and flow cytometry was performed 24 hours post-transfection. The modified VSV G constructs were expressed on the cell surface and detected by the 2F5 and 4E10 antibodies.

Figure 11:
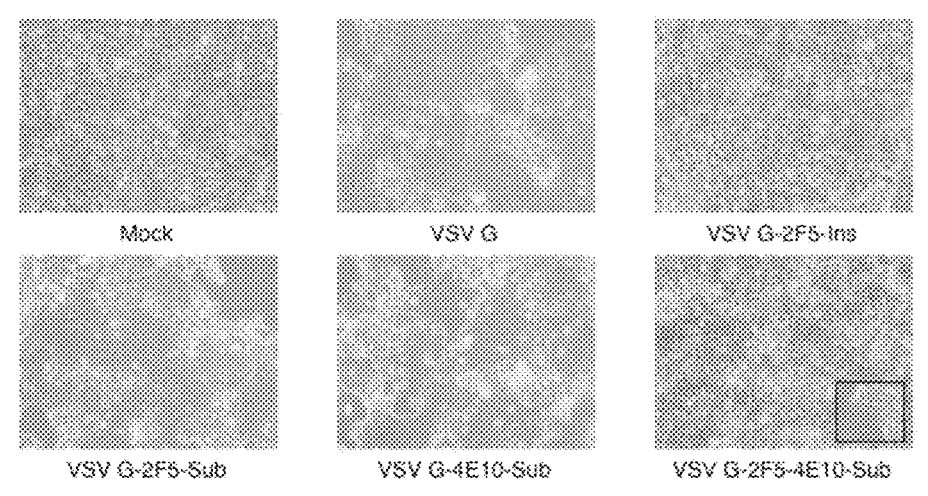

VSV G mediated cell-cell fusion is presented in FIG. 11. 293T cells were transfected with plasmid encoding VSV G, briefly exposed to pH 5.2 after 24 hours, and syncitia formation was observed. As shown in FIG. 11, VSV G-2F5-Sub and VSV G-4E10-Sub both induced cell-cell fusion. In addition, VSV G-2F5-4E10-Sub showed small areas of cell-cell fusion in rare cases. It was postulated that the modified G proteins may confer virus entry. To answer this question, a lentivirus reporter system was developed.

Figure 12:
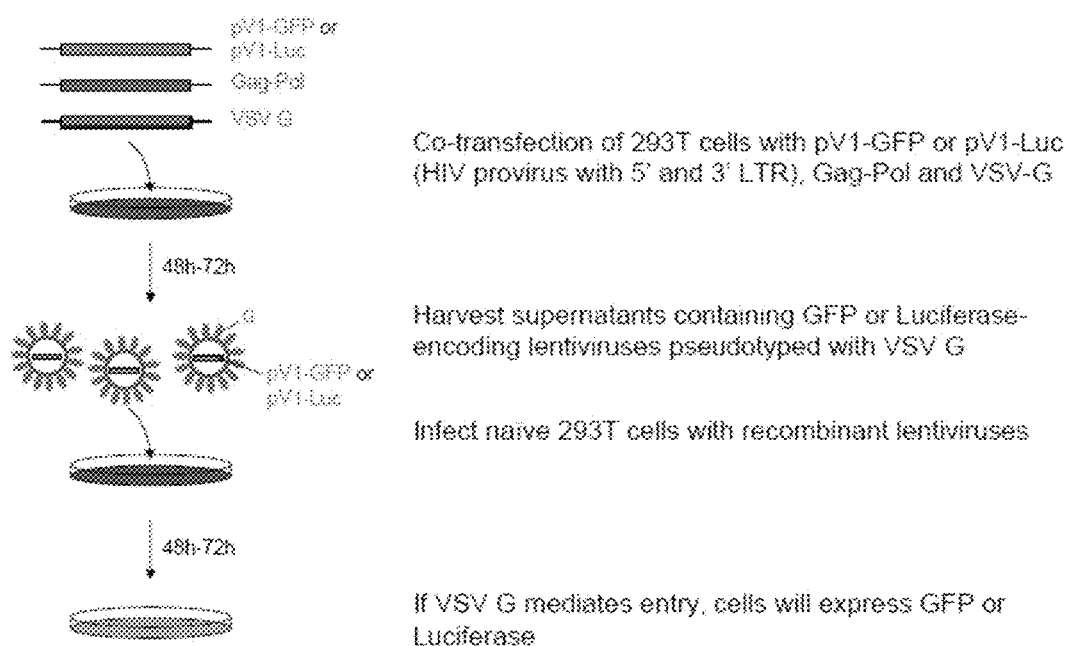
FIG. 12 depicts a reporter assay for functional analysis of modified VSV G proteins. A reporter lentivirus coding for green fluorescent protein (GFP) or luciferase (Luc) was packaged with Gag-Pol and pseudotyped with the VSV G variants and subsequently used to infect naïve 293T cells. GFP or luciferase expression was analyzed 72 hours post-infection.

A lentivirus reporter system is presented in FIG. 12. 293T cells were co-transfected with reporter plasmids pV1-GFP or pV1-Luc (HIV provirus with 5' and 3' LTR), and plasmids coding for Gag-Pol and VSV-G. Supernatants containing GFP or luciferase-encoding lentiviruses pseudotyped with VSV G were harvested, followed by infection of nalve 293T cells. If VSV G mediates entry, cells will express GFP or luciferase.

Figure 13:
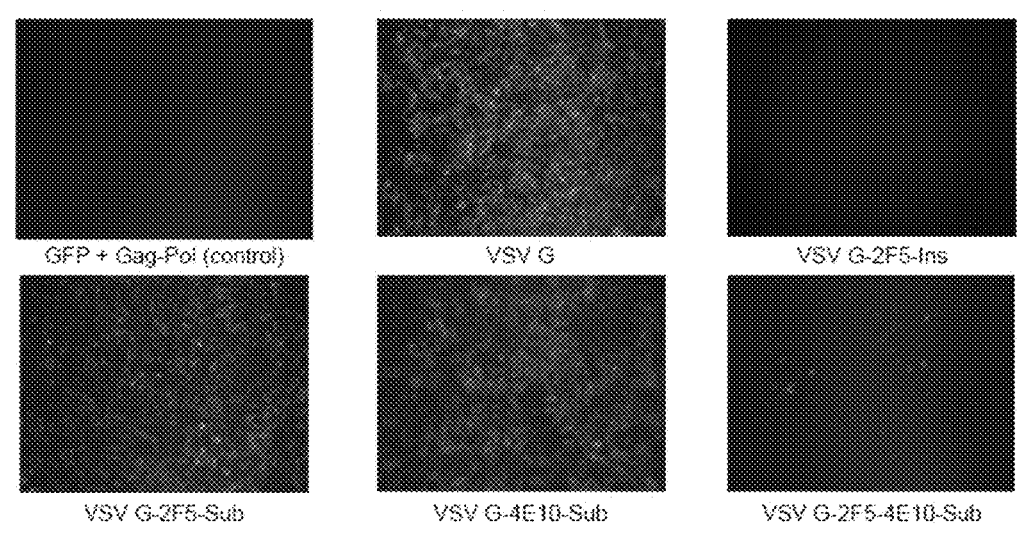

Infectivity of lenviruses pseudotyped with VSV G is presented in FIG. 13. 293T cells were infected with recombinant GFP-lentiviruses pseudotyped with VSV G variants. As shown in FIG. 13, the infectivity of VSV G-2F5-Sub and VSV G-4E10-Sub was similar to wild-type G.

Figure 14:
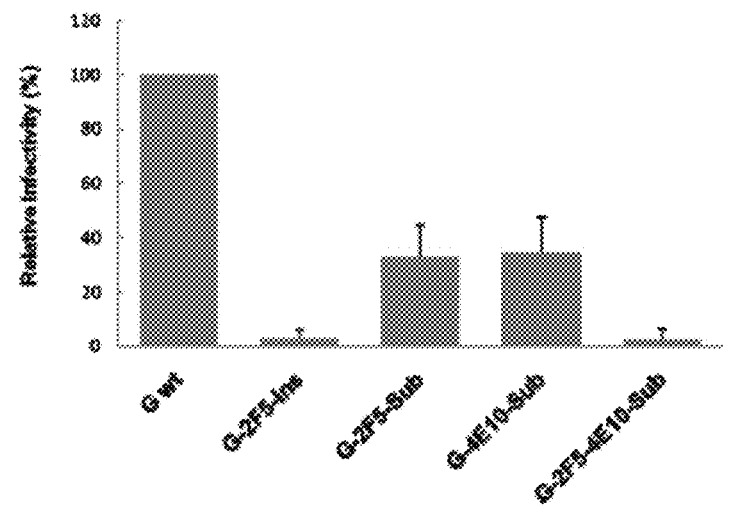

Infectivity of reporter lentiviruses pseudotyped with VSV G is presented in FIG. 14. 293T cells were infected with recombinant Luc-lentiviruses pseudotyped with VSV G variants. Lentiviruses pseudotyped with VSV G-2F5-Sub and VSV G-4E10-Sub retained 33% and 35% of infectivity compared to wild-type VSV G. It was postulated that these viruses be neutralized with the 2F5 and 4E10 antibodies.

Figure 15:
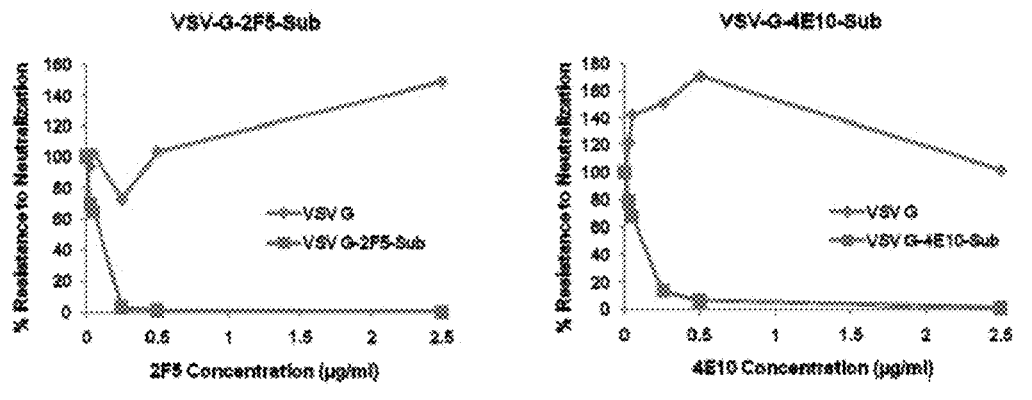

Neutralization of lentiviruses pseudotyped with VSV G is depicted in FIG. 15. Luc-lentiviruses pseudotyped with VSV G-2F5-Sub or VSV G-4E10-Sub were incubated with 2F5 or 4E10 antibody at various concentrations. Subsequently, 293T cells were infected with the Luc-lentiviruses, followed by assaying luciferase activity at 3 days post-infection. Luc-lentiviruses pseudotyped with VSV G-2F5-Sub and VSV G-4E10-Sub were efficiently neutralized with the 2F5 and 4E10 antibody, respectively. It was then postulated that modified G proteins could be incorporated into recombinant VSV.

Figure 16:
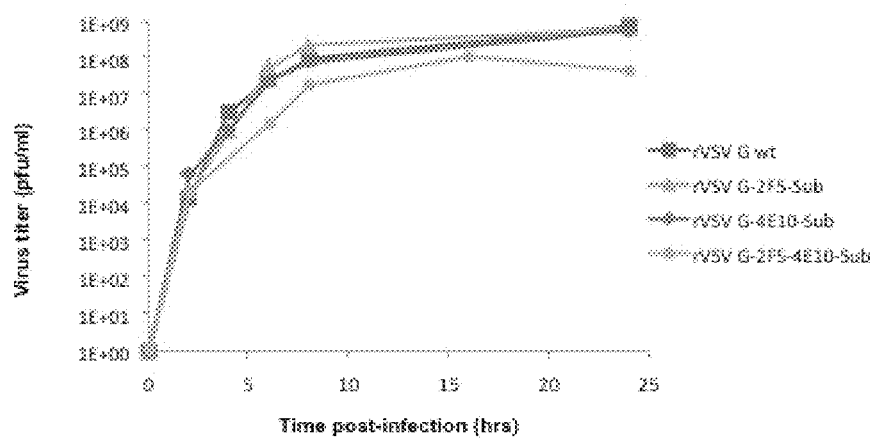
FIG. 16 depicts growth curves of recombinant VSV in Vero cells. Recombinant VSV (rVSV) containing the gene for wild-type G, G-2F5-Sub, G-4E10-Sub or G-2F5-4E10-Sub rescued in 293T cells was used to infect Vero cells at a multiplicity of infection (m.o.i.) of 5. Aliquots of the supernatant were taken at various times post-infection. Subsequently, naïve Vero cells were infected with the samples, followed by a standard plaque assay to determine the viral titer for each time point.

Recombinant VSV containing the gene coding for G-2F5-Sub, G-4E10-Sub and G-2F5-4E10-Sub were rescued. A growth curve analysis by plaque assay on Vero cells (m.o.i of 5) is shown in FIG. 16. The growth kinetics of rVSV containing G-2F5-Sub, G-4E10-Sub or G-2F5-4E10-Sub were similar to wild-type. It was then postulated that rVSV G-2F5-Sub, rVSV G-4E10-Sub and rVSV G-2F5-4E10-Sub could be neutralized with the 2F5 and 4E10 antibodies.

Figure 17:
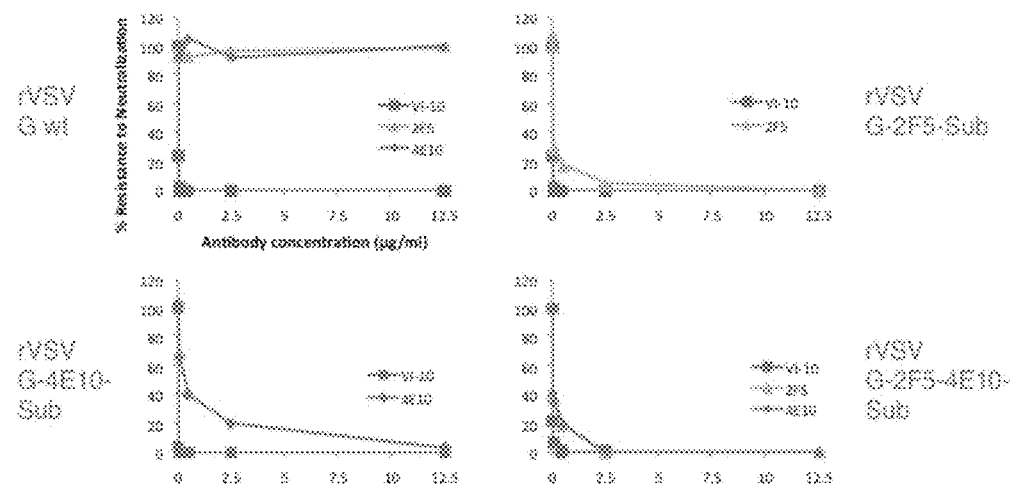

Neutralization of recombinant VSV with various antibodies is shown in FIG. 17. 5000 pfu rVSV G-2F5-Sub, rVSV G-4E10-Sub or rVSV G-2F5-4E10-Sub were incubated with VI-10 (control antibody against the ectodomain of VSV G, i.e. it should neutralize all viruses with G), 2F5 or 4E10 at various concentrations, followed by a plaque assay on Vero cells. As shown in FIG. 17, rVSV containing G-2F5-Sub, G-4E10-Sub or G-2F5-4E10-Sub was efficiently neutralized by the 2F5 and/or 4E10 antibodies.

To summarize this Example: (1) the 'stem' region of the Vesicular Stomatitis Virus (VSV) glycoprotein tolerated the insertion of the HIV-1 gp41 2F5 and 4E10 epitope sequences, (2) the modified VSV G proteins were expressed on the cell surface and detected by the respective HIV broadly neutralizing antibodies, (3) lentiviruses pseudotyped with VSV G-2F5-Sub or VSV G-4E10-Sub were infectious and could be neutralized with the 2F5 and 4E10 antibody, respectively and (4) recombinant VSVs with G-2F5-Sub, G-4E10-Sub or G-2F5-4E10-Sub were infectious, had similar growth kinetics like wild-type rVSV, and could be efficiently neutralized with the 2F5 and 4E10 antibodies. Applicants conclude that the HIV-1 gp41 2F5 and 4E10 epitope sequences were presented in a native-like conformation in the 'stem' region of the VSV glycoprotein.

Example 5: Optimization Strategy Adopted for Optimization of VSV G Protein Coding Sequence The gene was optimized for expression in eukaryotic cells using the following steps:
1. Started with amino acid sequence for VSV G serotype Indiana, strain Orsay (Genbank M11048.1)
2. The amino acid sequence was reverse-translated using the OPTIMIZER webtool (available on the OPTIMIZER website associated with Universitat Rovira i Virgili (URV)) and a human codon frequency table [Puigbò P et al. Nucleic Acids Res. 2007 July; 35 (Web Server issue):W126-31]
3. The DNA sequence obtained from reverse-translation was scanned for potential mRNA splice donor and acceptor sequences using the Splice Site Prediction webtool available on the fruitfly.org website [Reese M G et al. J Comput Biol. 1997 Fall; 4(3):311-23]. Potential splicing signals were disrupted subsequently by introducing one or two synonymous codons, which altered key elements in the donor or acceptor site. Synonymous codons were selected based on frequencies found in the Codon Table published by Zhang et al [Hum Mol. Genet. 1998 May; 7 (5):919-32] for GC-rich transcripts.
4. The reverse-translated sequence also was scanned for homopolymeric sequences≥5 nucleotides. Those that were ≥5 were interrupted by substitution of sequence with a synonymous codon as described in the step above.
5. The sequence was scanned for the presence of mRNA instability elements [Zubiaga A M et al. 1995, Mol. Cell. Biol. 15: 2219-2230]. None were found.
6. Optimal translation initiation (Kozak element [Kozak M. J Biol. Chem. 1991 25; 266 (30):19867-70]) and termination signals [Kochetov A V et al. FEBS Lett. 1998 4; 440(3):351-5] were introduced.
7. Unique XhoI and NotI sites were added to the 5' and 3' termini, respectively, as presented in FIGS. 28 A and 28B.

Example 6: Replication-Competent Vesicular Stomatitis Virus Vaccine Vectors for Delivery of Membrane-Anchored HIV Env Immunogens Vesicular stomatitis virus (VSV) is an enveloped RNA virus that naturally infects livestock (15). Methods to generate recombinant virus were developed in the mid 1990's (13, 26, 28) making it possible to produce VSV vectors that expresses foreign proteins. This technology, along many inherent properties of the virus, has made it practical to develop vaccine delivery vectors using VSV (4, 5).

Applicants' objective is to make VSV vaccine vectors that will co-express membrane-anchored Env immunogen and the natural VSV attachment protein (G), and incorporate both glycoproteins into infected cell membranes and progeny vector particles. The purpose of this vector design is to produce a replication competent vaccine that can use G for entry and propagation while also displaying Env immunogens to the immune system as transmembrane glycoproteins that closely mimic the authentic polypeptides found on the surface of HIV particles. Moreover, designing a VSV vaccine vector that will incorporate Env immunogens in the viral envelop will take advantage of the known immunogenic properties of antigens arrayed on virus particles (8).

Designing and Env immunogen delivery vector that also expresses G has important practical benefits. Vector particles containing functional quantities of G will efficiently infect many cell types in vivo providing an efficient mechanism of vaccine delivery (1, 6). Moreover, G naturally directs infection at mucosal surfaces (14) making it possible to deliver a vaccine mucosally. The broad cell tropism of G also is useful for vaccine manufacture because all continuous cell lines used for vaccine production are susceptible to infection mediated by this attachment protein.

Development of enveloped viral vectors that are genetically stable and efficiently incorporate foreign glycoproteins in the lipid bilayer of infected cells and virus particles is challenging. Earlier studies have shown that VSV can incorporate foreign transmembrane glycoproteins in the virus particle, but the abundance varies significantly depending on the protein (9, 10, 12, 17, 25). Furthermore, introduction of a gene encoding foreign glycoproteins can induce varying amounts of genetic instability (18). This is particularly relevant to Env, which is known to cause viral vector instability (29) and contain elements that interfere with its incorporation into heterologous viruses (9, 16).

Figure 29A:
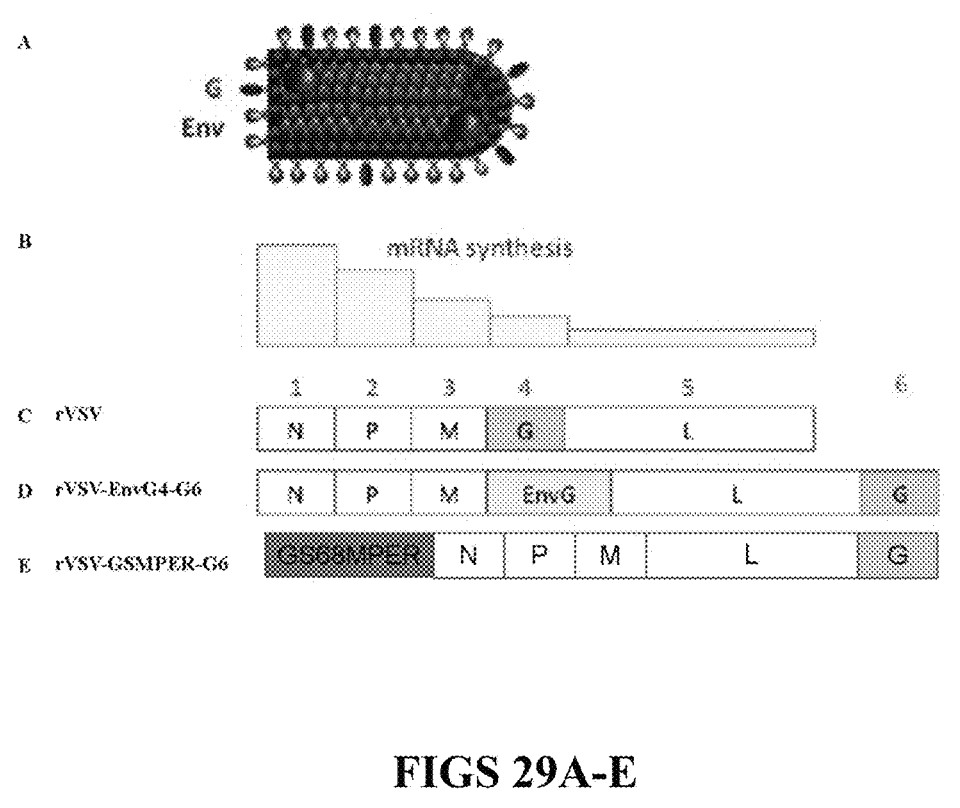

The G gene was transferred to the 5'-terminal position in the negative-sense RNA genome of the recombinant VSV vector, which is gene position 6 in the schematics below (accordingly, vector nomenclature used below refers to the VSV-Env-G6). For VSV as well as other negative-strand RNA viruses, there is a gradient of mRNA synthesis (3) with the highest transcriptional activity occurring at the 3' end of the genome (position 1 in FIG. 1B). There is a gradual decline in mRNA synthesis that is proportional to the distance from the 3', which results in genes at the 5' end being transcribed least like the L gene in the unmodified VSV genome (FIG. 29B). Thus, moving the VSV G coding sequence from the original position 4 (FIG. 29C) to the 5' terminus (FIGS. 29D and E) downregulates G protein expression.

Genes encoding the Env trimer immunogens were inserted into position 4 (FIG. 29D). This position provided the best balance of expression and vector genetic stability by reducing toxicity associated with expression of Env.

Genes encoding the G-stem-MPER immunogen were inserted in position 1 to increase mRNA synthesis and protein expression (FIG. 29E). Stable vectors expressing the small G-stem-MPER glycoprotein from this gene position were isolated.

Applicants have developed vectors that express G as well as membrane-anchored Env immunogens. In the examples provided below, the Env immunogens include HIV Env trimers (Subtype A, B or C) or epitopes derived from the membrane-proximal external region (MPER) of the gp41 Env subunit. To increase the abundance of Env immunogen relative to G incorporated into the infected cell membrane and progeny virus particles, and produce vectors with genetic stability needed for vaccine candidate development, Applicants made multiple modifications to the VSV genome and the Env immunogen insert including:
1. The VSV G gene was translocated to the 5' terminus of the VSV genome where its transcription is reduced (2, 3).
2. In some vectors, to further downregulate G incorporation into vector particles, the cytoplasmic tail of the glycoprotein was truncated (19).
3. To improve Env immunogen membrane insertion and incorporation into virus particles, the Env immunogens were constructed to contain the VSV G transmembrane and cytoplasmic tail in place of the analogous regions of Env (9, 25)
4. The signal peptide used to direct entry into the secretory pathway and determine post-translational processing was from either the VSV G or cellular CD5 (7).
5. The gene encoding the immunogen was designed specifically for improved stability in VSV vectors; the nucleotide sequence was designed with codons preferred by VSV, the guanine plus cytosine content was similar to the VSV genome, sequence motifs prone to mutation during VSV replication were modified using synonymous codons, and similarly, sequences that might direct unwanted RNA processing by cellular enzymes also were altered.

The G gene was transferred to the 5'-terminal position in the negative-sense RNA genome of the recombinant VSV vector, which is gene position 6 in the schematics below (accordingly, vector nomenclature used below refers to the VSV-Env-G6). For VSV as well as other negative-strand RNA viruses, there is a gradient of mRNA synthesis (3) with the highest transcriptional activity occurring at the 3' end of the genome (position 1 in FIG. 29B). There is a gradual decline in mRNA synthesis that is proportional to the distance from the 3', which results in genes at the 5' end being transcribed least like the L gene in the unmodified VSV genome (FIG. 29B). Thus, moving the VSV G coding sequence from the original position 4 (FIG. 29C) to the 5' terminus (FIGS. 29D-E) downregulates G protein expression.

Genes encoding the Env trimer immunogens were inserted into position 4 (FIG. 29D). This position provided the best balance of expression and vector genetic stability by reducing toxicity associated with expression of Env.

Genes encoding the G-stem-MPER immunogen were inserted in position 1 to increase mRNA synthesis and protein expression (FIG. 29E). Stable vectors expressing the small G-stem-MPER glycoprotein from this gene position were isolated.

A strategy to minimize the effect of anti-VSV immunity elicited by priming immunization has been described before (21). In brief, this approach makes use of the fact that there are two distinct VSV serotypes, Indiana and New Jersey. Antibodies generated after immunization with one G serotype do not neutralize the other in a prime boost regime. Using both vectors in combination can be useful to overcome anti-vector immunity.

The VSV vector genetic background is based on an Indiana serotype. To construct vectors for conducting boost immunizations, the G gene in the Indiana serotype vector ($G_{IN}$) was replaced with sequence from the New Jersey serotype ($G_{NJ}$). FIG. 30 shows that Env JRFL is expressed efficiently from both vectors expressing either the $G_{IN}$ or $G_{NJ}$ attachment protein.

To develop vectors with increased abundance of Env immunongen relative to G, the VSV G cytoplasmic tail was truncated leaving only a single amino acid. This mutation is known to decrease the efficiency of G incorporation into vector particles (24). Stable vectors encoding Clade A or Clade C EnvG and a truncated G ($G_{CT1}$) have been isolated.

EnvG immunogens were designed to increase expression and membrane incorporation of Env trimers that faithfully represent the trimeric spike found on the surface of HIV particles.

The nucleotide sequence has been designed with a codon bias consistent with the VSV genome; Nucleotide sequence motifs that might cause instability during VSV replication or might be target of cellular RNA processing enzymes were altered by replacement with synonymous codons.

The Env signal peptide was replaced with either the VSV G or cellular CD5 sequence to direct translation and processing in the secretory pathway.

The Env cytoplasmic and transmembrane domains were replaced with the transmembrane and C-tail domains from VSV $G_{IN}$.

For the G-Stem MPER immunogen, 68 amino acids of G ectodomain were also included.

FIGS. 29A-E depict VSV genome and viral particles structure. A. scheme of the new viral vector design. Both glycoproteins VSV G (in red) and Env (blue) get incorporated into the VSV particle. B. Gradient of mRNA synthesis from the VSV genome. Genes located at the 3' terminus (position 1) are transcribed more efficiently than the downstream genes. B. Position of the VSV genes in the genome. D. and E. New vectors designed to downregulate expression of G by moving to position 6, and expressing Env inserts from positions 4 (D) and 1 (E).

FIGS. 30A-B depict expression of Env (Clade B) JR-FL protein on infected cells and incorporation of G and Env proteins into viral particles. Western blot analysis of Env JR-FL protein expression in total cell lysates. Total cell lysates were prepared from infected Vero cells with two different clones of VSV-Env JRFL-$G6_{IN}$ (lanes 1 and 2) and two other clones of VSV-Env JRFL $G6_{NJ}$ (lanes 3 and 4). Clones were originated after two rounds of virus plaque purification. A. EnvG protein detected using monoclonal antibody 2F5. B. Detection of Env JRFL and $G_{IN}$ using an anti-VSV $G_{IN}$ (C-tail) antibody and anti-VSV N polyclonal rabbit antiserum antibody. Note that the $G_{IN}$ C-tail antibody does not recognize G protein for the NJ serotype (lanes 3 and 4)

FIG. 31 depicts expression of VSV $G_{CT1}$ and Env (Clade A) BG505 or Env (Clade C) 16055 on the surface of infected cells. Flow cytometry analysis of Vero cells infected with VSV Env (clades A and C)-$G_{CT1}$ using a panel of broadly neutralizing antibodies against Env and an anti-VSV $G_{IN}$ antibody (VI10). The vector VSV-MGP-$G_{CT1}$ expresses an Env trimer that has been modified by introduction of Cys residues intended to form disulphide linkages between gp41 and gp120 subunits.

FIG. 32 depicts a design of the Env immunogens for display in the VSV particle. The inserts include the VSV (purple) or CD5 (red) secretion signals, Env ectodomain (clades A, B or C), or Env MPER region (green) plus Transmembrane (light blue) and C tail domains (yellow) of VSV G.

FIG. 33 depicts Env (clade C) 16055 and VSV G proteins are expressed on the cell surface of VSV-Env-G6 infected cells. This VSV-EnvG-G6 construct carries a fusion of the CD5 leader peptide to the Env Clade C protein ectodomain and VSV G transmembrane and C-tail domains. Vero cells infected with VSV-Env (clade C)-G6 vector were stained with human anti-HIV Env monoclonal antibodies VRC01, PG9, PG16, b12, 2F5, and an antibody against VSV $G_{IN}$ (VI10). Fluorescence was acquired on a modified BD LSR II flow cytometer.

FIG. 34 depicts rVSV-EnvG (cladeC) 16055-G6 expresses both functional EnvG and VSV G proteins. This vector could use either EnvG or G to infect susceptible cell substrate. Functional VSV G was confirmed by successful viral propagation in Vero cells. For virus infection through EnvG protein, a GHOST cell line that expresses CCR5 and CD4 receptors was used as substrate. GHOST cells can be infected with these vectors via VSV G and/or EnvG proteins. To corroborate the EnvG was functional, the virus was incubated prior to infection with anti-VSV G serum, for 30 minutes at 37° C., to block VSV G binding to cell receptor. Vector plus antibody was then used for infection of CD4/CCR5+ GHOST cells. Syncytia formation, characteristic of Env mediated fusion, showed up 24 hours after infection. The figure shows a monolayer of GHOST cells 24 hours after infection with VSV EnvG 16055-G6 blocked with anti-VSV G serum. Red arrows point to syncitia.

FIG. 35 depicts EnvG (clade A) BG505 and VSV G proteins are expressed on the cell surface of VSV-EnvG-G6 infected cells. This VSV-EnvG-G6 construct carries a fusion of the VSV leader peptide, Env Clade A protein ectodomain and VSV G transmembrane and C-tail domains. Vero cells infected with VSV-EnvG (clade A)-G6 vector were stained with human anti-HIV Env monoclonal antibodies PGT121, PGT125, PGT130, PGT136, B6 and 2G5, and an antibody against VSV $G_{IN}$ (VI10). Fluorescence was acquired on a modified BD LSR II flow cytometer.

FIG. 36 depicts flow cytometry study of cell surface expression of MPER and VSV-G. Vero cells were infected with rVSV-GS68MPER-G6 vector and stained with monoclonal antibodies. MPER epitope is recognized by human monoclonal antibodies 2F5 and 4E10. VSV G is recognized by mouse monoclonal antibody Vi10.

FIG. 37 depicts an Env (clade B) JRF-L protein is expressed on the surface of infected cells. Flow cytometry analysis of Vero cells infected with JRFL-G$_{IN}$ and JRFL-G$_{NJ}$ using a panel of broadly neutralizing antibodies. Vero cells were infected with either VSV-EnvG-G$_{NJ}$ or G$_{IN}$ at different multiplicity of infection (0.1 and 0.05). After 16 hrs, cells were collected, stained with a panel of broadly neutralizing antibodies specific for HIV Env. G2, VSV control virus. NJ, VSV-EnvG-G$_{NJ}$. IN, VSV-EnvG_G$_{IN}$.

FIG. 38 depicts co-expression of G and EnvG on the surface of infected cells. Flow cytometry analysis of Vero cells infected with VSV EnvG (clade B) JRFL-G$_{IN}$ using a panel of broadly neutralizing antibodies against Env and an anti-VSV G$_{IN}$ antibody (VI10). The data shows that 60% of the infected cells can be recognized by the VSV-G antibody, and at least 40% can be also recognized by the anti-Env monoclonal antibodies.

FIG. 39 depicts immune responses elicited in mice by plasmid DNA prime and VSV-EnvG JRFL-G$_6$ vector boost. VSV-EnvG JRFL-G6 vector boosts antibody responses in serum of mice immunized with pDNA-EnvG-JRFL+plasmid IL12 by electroporation (EP). Balb/c mice received the JRFL pDNA+pIL-12 by EP at weeks 0 and 3, and a boost with VSV-EnvG G6 vectors at week 6. Anti-Env serum antibody titers were determined one week after boost. A statistically significant increase in antibodies was observed after VSV boost by intramuscular (1M, p=0.03) and intranasal (IN, p=0.004) routes.

FIGS. 40A-D depict Env specific CD4+ T cell responses in spleens and lungs in mice after VSV-EnvG JRFL-G6 vector boost. Balb/c mice received the pDNA JRFL+ IL-12 EP at weeks 0 and 3, and a boost with VSV-EnvG JRFL G6 vector at week 6. Anti-Env cellular responses were analyzed two weeks after DNA prime and 2 weeks after VSV boost. Cells were stained with LIVE/DEAD Fixable Violet Dead Cell Stain (Molecular Probes), CD3, CD4, IFN-g, IL-2, TNF (BD Biosciences), and CD8 (BioLegend). Stained cells were resuspended in 0.5% paraformaldehyde before being acquired on a modified BD LSR II flow cytometer. A marked increase in immune responses can be observed two weeks after immunization by intramuscular and intranasal routes. A. and B. cells isolated from spleens. C. and D. cells isolated from lungs.

Examples of genes designed for VSV vectors encoding Env immunogens.

```
SEQ 1: EnvG (Clade A) BG505
VSVG signal peptide (SEQ ID NO: 2) VSVG tm (SEQ ID NO: 3) VSVG ct (SEQ ID NO: 4)
Protein
                                                                                    (SEQ ID NO: 1)
mkcllylaflfigvnckasaenlwvtvyygvpvwkdaettlfcasdakayetekhnvwathacvptdpnpqeihlenvteefnmwk nnmveqmhtdiislwdqslkpcvkltplcvtlqctnytnnitddmrgelkncsfnmttelrdkkqkvyslfyrldvvqinenqgnrsn nsnkeyrlincntsaitqacpkvsfepipihycapagfailkckdkkfngtgpcpsvstvqcthgikpvvstqlllngslaeeevmirsen itnnaknilvqfntpvqinctrpnnntrksirigpgqafyatgdiigdirqahctvskatwnetlgkvvkqlrkhfgnntiirfanssggdle vtthsfncggeffycntsglfnstwisntsvqgsnstgsndsitlpcrikqiinmwqrigqamyappiqgvircvsnitgliltrdggstnst tetfrpgggdmrdnwrselykykvvkieplgvaptrakrrvvgrekravgigavflgflgaagstmgaasmtltvqarnllsgivqqqs nllraieaqqhllkltvwgikqlqarvlaverylrdqqllgiwgcsgklicttnvpwnsswsnrnlseiwdnmtwlqwdkeisnytqiiy glleesqnqqekneqdllaldkwaslwnwfdisnwlwyikssiasfffiigliiglflvlrvgiylciklkhtkkrqiytdiemnrlgk*

VSVG signal sequence (SEQ ID NO: 6) VSVG tm (SEQ ID NO: 7) VSVG ct (SEQ ID NO: 8)
Nucleotide
                                                                                    (SEQ ID NO: 5)
atgaagtgccttttgtacttagttttttattcatcggggtgaattgcaaggctagcgcagagaatttgtgggtaacagtctactatggagtccct gtatggaaggatgcagagacaacattgttctgtgctagtgacgcaaaggcttacgagacggagaagcacaatgtgtgggcaactcacgcat gtgtcccaaccgatccaaatcctcaagagattcatctagagaatgtgactgaagaattcaatatgtggaagaataatatggtagagcaaatgc atacagatatcattagtttatggaccagtcacttaaaccctgcgttaaattgacgcctctatgtgtgacacttcaatgtactaatgttacaaacaa cataacagatgatatgagaggagaactgaagaactgtagtttcaacatgacgacagagttgcgtgacaagaaacagaaagtgtattcactat tctatcggttggatgtagtacagataaatgagaatcaaggaaacaggtccaacaactctaacaaagagtacagacttattaattgcaatacca gtgctatcacgcaagcctgcccaaaggtttcatttgaaccaatacctattcattattgtgcacctgctggattcgccatcctcaaatgtaaagac aagaagttcaatggaacaggaccctgcccatcagtttcaaccgttcagtgcacccacggaatcaagcctgtagttagtactcaattattgttaa atgggagatagctgaagaagaagttatgattagatcagagaatattaccaataatgcgaagaacatcttggttcaattcaatactccagtcca gatcaattgcacaaggcctaataataataccagaaagagtataagaattgggccaggacaggcattctatgcaacaggagatataatcgga gacattcgacaagcgcactgcactgtttctaaggccacttggaatgaaacattgggtaaagttgtaaagcaacttcggaagcatttcggaaat aacacaattattagatttgcgaactcatctggagggggatctggaagtgacaacacactctttcaattgcggtggcgagttcttctattgtaataca agtggattatttaactctacttggatttcaaatacctcagtccaaggatctaattcaacagggtctaacgattctataacattaccttgccgtataaa gcaaattattaatatgtggcaaagaatcgggcaagcgatgtatgaccacctattcaaggcgtgattcgttgcgtttcaaacataacagggttg
```

-continued

```
atcctgaccagggatggaggctctaccaattccaccaccgagaccttccgtcccggtggcggagatatgcgggataactggagatcagag ctctataagtataaggttgtgaagattgaacctcttggagttgcccctacaagagcaaagagaagggtggttggccgagagaagagagcag ttggcatcggtgctgtctttctcggatttcttggagcagctggatccactatgggagcagcatcaatgacactaacagtgcaggctagaaattt gcttagcggaatcgttcagcagcagagcaattctactaagagcaattgaagcacagcaacatctcttaaagttgacggtgtggggcattaaac aactacaagcgagagtgcttgccgtcgaaagatatttgcgagaccaacagctattgggtatttggggttgttctgggaaattaatttgcacaac aaatgttccatggaactcctcctggagtaataggaatttaagtgagatatgggacaacatgacatggttgcagtgggacaaggaaatctcaaa ttatacacagataatctatggattattagaagagtctcagaatcagcaagagaagaatgaacaggatttgcttgcattggataagtgggcttctc tatgGaactggttcgatattagtaattggctctggtatattaagagctctattgcctctttttcttatcatagggttaatcattggactattcttggttc tccgagttggtatttatctttgcattaaattaaagcacaccaagaaaagacagatttatacagacatagagatgaaccgacttggaaagtaa
```

SEQ 2: G-Stem-MPER (GS68MPER)
VSVG signal peptide (SEQ ID NO: 10) MPER epitope (SEQ ID NO: 11) GStem68 VSVG
tm (SEQ ID NO: 3) VSVG ct (SEQ ID NO: 4)
Protein (SEQ ID NO: 9)

```
mkcllylaflfigvncksgellleldkwaslwnwfditkwlwyiksggykfplymighgmldsdlhlsskaqvfehphiqdaasqlpd detlffgdtglsknpiefvegwfsswkssiasffffiigliiglflvlrvgiylciklkhtkkrqiytdiemnrlgk*
```

VSVG signal sequence (SEQ ID NO: 13) MPER epitope (SEQ ID NO: 14) GStem68
VSVG tm (SEQ ID NO: 15) VSVG ct (SEQ ID NO: 16)
Nucleotide (SEQ ID NO: 12)

```
atgaagtgcctactttaccttgcatttctattatcggagttaattgcaaatccggagagctcctcgaattggataaatgggcaagcctatggaac tggtttgacattacgaaatggttgtggtacattaagtccggaggttataaattcccttatatatgattggacacggcatgctggattcagaccttc acctctcatcaaaggcccaggtgtttgagcatcctcacattcaggatgctgcttcacagctaccggatgacgaaactctcttcttcggagacac cggtttatctaagaatcctatagagttcgtggaagggtggttctcctcttggaagtcgtccatcgcaagcttcttcttcataataggtctcattattg gactattcttgtcctgagagtcggaatatatctatgtatcaagctcaaacataccaagaagaggcagatctatacagatattgaaatgaatcga ttagggaaataa
```

SEQ 3: EnvG (Clade C) 16055 insert
CD5 signal peptide (SEQ ID NO: 18) VSVG tm (SEQ ID NO: 3) VSVG ct (SEQ ID NO: 4)
Protein (SEQ ID NO: 17)

```
mpmgslqplatlyllgmlvasvlaagnlwvtvyygvpvwkeakttlfcasdakayekevhnvwathacvptdpnpqemvlenvte nfnmwkndmveqmhedvislwdqslkpcvkltplcvtlecrqvnttnatssvnvtngeeikncsfnatteirdkkqkvyalfyrldiv pleeerkgnsskyrlincntsaitqacpkvtfdpipihycapagyailkcnnktfngtgpcnnvstvqcthgikpvvstqlllngslaegei iirsenltnnvktiivhlnesveivetrpnnntrksirigpgqtfyatgdiignirqaycnikkddwirtlqrvgkklaehfprriinftspagg dleitthsfncrgeffycntsslfnstynpndtnsnsssnsssldittpcrikqiinmwqevgramyappiegnitcksnitglllvrdggve sneteifrpgggdmrnnwrselykykvveikplgiaptaakrrvverekravglgavifgflgaagstmgaasitltvqarqllsgivqqq snllkaieaqqhllqltvwgikqlqtrvlaieryylkdqqllgiwcsgklicttavpwnsswsnkshdeiwgnmtwmqwdreisnytn tiyrlledsqnqqeqnekdllaldswenlwnwfsitkwlwyiksssiasffffligliiglflvlrvgiylciklkhtkkrqiytdiemnrlgk*
```

CD5 signal sequence (SEQ ID NO: 20) VSVG tm (SEQ ID NO: 15) VSVG ct (SEQ ID NO: 21)
Nucleotide (SEQ ID NO: 19)

```
atgccaatgggatcattgcaaccattggcaacattgtatttgttgggaatgttggttgcatcagttttggcagcagggaatttatggttactgtat attacggagttcctgtttggaaagaagccaagaccacattattctgtgctagtgacgctaaggcttacgagaaagaagtgcataacgtttggg caacacatgcgtgtgtacctaccgaccccaatcctcaagaaatggtacttgaaaatgtaaccgaaaattttaacatgtggaagaatgatatggt tgaacagatgcatgaagatgtcattagcctatgggatcaatctctaaagccatgtgtaaagctcacgcctttgtgtgttactctcgaatgcagac aggtcaacacgacaaatgcaacatcttcagttaatgtaaccaacggagaggaaattaagaattgtagattaatgctaccactgaaattcgtga taagaagcaaaaggtgtatgcattatttttaccgattggatattgtgcctttggaagaagagcgaaagggcaactcttccaaatacagattaatc aactgcaacacaagcgcgattacgcaagcttgtccaaaagtcaccttcgaccccatcccaatccattactgtgcacctgccggatacgcaatt cttaaatgtaataataagacttttaatggaacaggcccatgtaataatgtgtctacagtacagtgtacccacggcatcaaaccggttgtttctaca
```

-continued cagttgctcttaaatgggtcattggctgaaggagagattattattcggtctgaaaacctcaccaataatgtaaagactatcatcgttcacttgaac gaatctgtggagattgtctgtactagaccaaataataataccagaaagtcaattagaataggacctggacaaactttctacgccacgggcgat attattgggaatattagacaagcatattgcaacattaagaaagatgattggataagaacattgcagcgggttgggaagaaattggccgaacat ttccccagaagaataatcaactttacatcacctgcaggaggagatttagaaattacaacgcattcatttaactgtagaggggagttcttctattgt aatacatcttccttgttcaattctacctacaatcctaatgataccaatagtaattcatcctcgtcgaattcttccctggatattacaattccatgtagg atcaaacaaatcattaatatgtggcaagaagtcggtagagcgatgtacgcacctcccattgaaggaaatattacatgcaagagcaatattacg ggcctgttgctcgttcgagatggtggagtcgaatccaatgaaacagagatcttccgtcctggaggaggggatatgagaaataattggagatc tgaactctataaatacaaagtagtggaaattaaaccattagggatagcaccgacggcagctaaaagacgagtggtggagcgggagaagcg tgctgaggattgggagccgtcatatttgggtttctcggagctgcaggatctacaatgggtgcggcatcgattacacttacagtgcaagcaag gcaattacttagtggaatagttcaacaacaatcaaatctgctgaaagccattgaggcacaacagcatctgctacaattgacagtgtggggaat caaacaattacagactagagttcttgcaatcgaaagatatttaaaggaccaacaactcttgggcatttggggatgttcgggaaagcttatatgt acaacagcagtaccatggaactcttcttggtccaacaaatcacacgacgagatttggggtaatatgacctggatgcaatgggatagagagat ttctaattacacaaataccatctatagattgcttgaagattctcaaaatcagcaagagcagaacgagaaagatttattagcactcgatagttggg agaatttgtggaattggttttcaattaccaagtggctctggtacataaagtcgtccatcgcaagcttcttcttcataataggtctcattattggactc tttcttgtcctgagagtcggaatatatctatgtatcaagctcaaacatacaaagaagaggcagatctatacagatattgaaatgaatcgattagg gaagtaa SEQ 4: EnvG (Clade B) JR-FL insert (with CDS leader, JRFL Env ectodomain, TM and CT from $G_{IN}$)
Sequence key
BstB1 restriction site
Kozak
CD5 signal peptide (SEQ ID NO: 23)
VSV G Transmembrane domain (SEQ ID NO: 3)
VSV G Ctail (SEQ ID NO: 4)
Pac 1 restriction site
Protein (SEQ ID NO: 22)

MPMGSLQPLATLYLLGMLVASVLAVEKLWVTVYYGVPVWKEATTTLFCASDAKAYDT

EVHNVWATHACVPTDPNPQEVVLENVTEHFNMWKNNMVEQMQEDIISLWDQSLKPCV

KLTPLCVTLNCKDVNATNTTNDSEGTMERGEIKNCSFNITTSIRDEVQKEYALFYKLDV

VPIDNNNTSYRLISCDTSVITQACPKISFEPIPIHYCAPAGFAILKCNDKTFNGKGPCKNVS

TVQCTHGIRPVVSTQLLLNGSLAEEEVVIRSDNFTNNAKTIIVQLKESVEINCTRPNNNTR

KSIHIGPGRAFYTTGEIIGDIRQAHCNISRAKWNDTLKQIVIKLREQFENKTIVFNHSSGGD

PEIVMHSFNCGGEFFYCNSTQLFNSTWNNNTEGSNNTEGNTITLPCRIKQIINMWQEVGK

AMYAPPIRGQIRCSSNITGLLLTRDGGINENGTEIFRPGGGDMRDNWRSELYKYKVVKIE

PLGVAPTKAKRRVVQREKRAVGIGAVFLGFLGAAGSTMGAASMTLTVQARLLLSGIVQ

QQNNLLRAIEAQQRMLQLTVWGIKQLQARVLAVERYLGDQQLLGIWGCSGKLICTTAV

PWNASWSNKSLDRIWNNMTWMEWEREIDNYTSEIYTLIEESQNQQEKNEQELLELDKW

ASLWNWFDITKWLWYIKSSIASFFFIIGLIIGLFLVLRVGIYLCIKLKHTKKRQIYTDIEMN

RLGK*

BstB1 restriction site (SEQ ID NO: 33)
Kozak (SEQ ID NO: 25)
CD5 signal sequence (SEQ ID NO: 26)
VSV G Transmembrane domain (SEQ ID NO: 27)
VSV G Ctail (SEQ ID NO: 28)
Pac 1 restriction site (SEQ ID NO: 29)
Nucleotide
CD5 secretion signal JRFL-VSV Tm Ctail Optimized (SEQ ID NO: 24)

ttcgaacaactaatatcctgtatctctatccctatgaaaaaaactaacagagatcgatctgtttccttgaggagccaccatgccaatgggatcat tgcaaccattggcaacattgtatttgttgggaatgttggttgcatcagtgttggcagttgagaaattgtgggttacagtttattatggagttccagtt -continued

```
tggaaagaagcaacaacaacattgttctgtgcatctgatgcaaaggcatatgatacagaagttcataatgtttgggcaacacatgcatgttc caactgatccaaatccacaagaagttgtgttggagaatgttacagaacatttcaatatgtggaagaataatatggttgaacaaatgcaagaag atattatttcattgtgggatcaatcattgaaaccatgtgttaaattgacaccattgtgtgttacattgaattgtaaagatgttaatgcaacaaataca acaaatgattcagaaggaacaatggaaagaggagaaattaagaattgttcatttaatattacaacatcaattagagatgaagttcagaaagaat atgcattgttctataaattggatgttgttccaattgataataataatacatcatatagattgatttcatgtgatacatcagttattacacaagcatgtcc aaagatttcatttgaaccaattccaattcattattgtgcaccagcaggatttgcaatcttgaaatgtaatgataagacatttaatgaaagggacc atgcaagaatgtttcaacagttcaatgtacacatggaattagaccagttgtttcaacacaattgttgttgaatggatcattggcagaagaagaag ttgttattagatcagataatttcacaaataatgcaaagacaattattgttcaattgaaagaatcagttgaaattaattgtacaagaccaaataataat acaagaaagtcaattcatattggaccaggaagagcattctatacaacaggagaaattattggagatattagacaagcacattgtaatatttcaa gagctaaatggaatgatacattgaaacaaattgttattaaattgagagaacaatttgagaataagacaattgtgtttaatcattcatctggaggag atccagaaattgttatgcattcatttaattgtggaggagaattcttctattgtaattcaacacaattgtttaattcaacatggaataataatacagaag gatcaaataatacagaaggaaatacaattacattgccatgtagaattaaacaaattattaatatgtggcaagaagttggaaaggctatgtatgc accaccaattagaggacaaattagatgttcatcaaatattactggattgttgttgacaagagatggaggaattaatgagaatggaacagaaatc tttagaccaggaggaggagatatgagagataattggagatcagaattgtataaatataaagttgttaagattgaaccattgggagttgcaccaa ctaaagcaaagagaagagttgttcaaagagagaagagagcagttggaattggagcagtgttcttgggattcttgggagcagcaggatcaac aatgggagcagcatcaatgacattgacagttcaagcaagattgttgttgtcaggaattgttcaacaacagaataatttgttgagagcaattgaa gcacaacaaagaatgttgcaattgacagtttgggaattaaacaattgcaagcaagagtgttggcagttgaaagatatttgggagatcaacaa ttgttgggaatttggggatgttcaggaaagttgatttgtacaacagcagttccatggaatgcatcatggtcaaataaatcattggatagaatttgg aataatatgacatggatggaatgggaaagagaaattgataattatacatcagaaatttatcattgattgaagaatcacagaatcaacaagaga agaatgaacaagaattgttggaattggataaatgggcatcattgtggaattggtttgatattactaaatggttgtggtatattaaatcatcaattgc atcattcttctttattattggattgattattggattgttcttggtgttgagagttggaatttatttgtgtattaaattgaaacatacaaagaagagacaaa tttatacagatattgaaatgaatagattgggaaagtgagctcaaatcctgcacaacagattcttcatgtttgaaccaaatcaacttgtgatatcat gctcaaagaggccttaattaa
```

SEQ 5: EnvG (Clade B) JR-FL insert (with VSV secretion signal-JRFL-VSV TmCtail)
Sequence key
BstB1 restriction site
Kozak
VSV Signal Peptide (SEQ ID NO: 31)
VSV G Transmembrane domain (SEQ ID NO: 3)
VSV G Ctail (SEQ ID NO: 4)
Pac 1 restriction site
Protein (SEQ ID NO: 30)

MKCLLYLAFLFIGVNCAVEKLWVTVYYGVPVWKEATTTLFCASDAKAYDTEVHNVW

ATHACVPTDPNPQEVVLENVTEHFNMWKNNMVEQMQEDIISLWDQSLKPCVKLTPLCV

TLNCKDVNATNTTNDSEGTMERGEIKNCSFNITTSIRDEVQKEYALFYKLDVVPIDNNNT

SYRLISCDTSVITQACPKISFEPIPIHYCAPAGFAILKCNDKTFNGKGPCKNVSTVQCTHGI

RPVVSTQLLLNGSLAEEEVVIRSDNFTNNAKTIIVQLKESVEINCTRPNNNTRKSIHIGPGR

AFYTTGEIIGDIRQAHCNISRAKWNDTLKQIVIKLREQFENKTIVFNHSSGGDPEIVMHSF

NCGGEFFYCNSTQLFNSTWNNNTEGSNNTEGNTITLPCRIKQIINMWQEVGKAMYAPPI

RGQIRCSSNITGLLLTRDGGINENGTEIFRPGGGDMRDNWRSELYKYKVVKIEPLGVAPT

KAKRRVVQREKRAVGIGAVFLGFLGAAGSTMGAASMTLTVQARLLLSGIVQQQNNLLR

AIEAQQRMLQLTVWGIKQLQARVLAVERYLGDQQLLGIWGCSGKLICTTAVPWNASWS

NKSLDRIWNNMTWMEWEREIDNYTSEIYTLIEESQNQQEKNEQELLELDKWASLWNWF

DITKWLWYIKSSIASFFFIIGLIIGLFLVLRVGIYLCIKLKHTKKRQIYTDIEMNRLGK*

BstB1 restriction site (SEQ ID NO: 33)
Kozak (SEQ ID NO: 25)
VSV Signal sequence (SEQ ID NO: 34)
VSV G Transmembrane domain (SEQ ID NO: 35)
VSV G Ctail (SEQ ID NO: 36)
Pac 1 restriction site (SEQ ID NO: 29)
Nucleotide (SEQ ID NO: 32)

ttcgaacaactaatatcctgtatctctatccctatgaaaaaaactaacagagatcgatctgtttccttgaggagccaccatgaagtgccttttgta cttagcttattattcatcggggtgaattgcgctgttgagaaattgtgggttacagtttattatggagttccagtttggaaagaagcaacaacaaca ttgttctgtgcatctgatgcaaaggcatatgatacagaagttcataatgtttgggcaacacatgcatgtgttccaactgatccaaatccacaaga agttgtgttggagaatgttacagaacatttcaatatgtggaagaataatatggttgaacaaatgcaagaagatattatttcattgtgggatcaatc attgaaaccatgtgttaaattgacaccattgtgtgttacattgaattgtaaagatgttaatgcaacaaatacaacaaatgattcagaaggaacaat ggaaagaggagaaattaagaattgttcatttaatattacaacatcaattagagatgaagttcagaaagaatatgcattgttctataaattggatgtt gttccaattgataataataatacatcatatagattgatttcatgtgatacatcagttattacacaagcatgtccaaagatttcatttgaaccaattcca attcattattgtgcaccagcaggatttgcaatcttgaaatgtaatgataagacatttaatggaaagggaccatgcaagaatgtttcaacagttca atgtacacatggaattagaccagttgtttcaacacaattgttgttgaatggatcattggcagaagaagaagttgttattagatcagataatttcac aaataatgcaaagacaattattgttcaattgaaagaatcagttgaaattaattgtacaagaccaaataataatacaagaaagtcaattcatattgg accaggaagagcattctatacaacaggagaaattattggagatattagacaagcacattgtaatatttcaagagctaaatggaatgatacattg aaacaaattgttattaaattgagagaacaatttgagaataagacaattgtgtttaatcattcatctggaggagatccagaaattgttatgcattcatt taattgtggaggagaattcttctattgtaattcaacacaattgtttaattcaacatggaataataatacagaaggatcaaataatacagaaggaaa tacaattacattgccatgtagaattaaacaaattattaatatgtggcaagaagttggaaaggctatgtatgcaccaccaattagaggacaaatta gatgttcatcaaatattactggattgttgttgacaagagatggaggaattaatgagaatggaacagaaatctttagaccaggaggaggagata tgagagataattggagatcagaattgtataaatataaagttgttaagattgaaccattgggagttgcaccaactaaagcaaagagaagagttgt tcaaagagagaagagagcagttggaattggagcagtgttcttgggattcttgggagcagcaggatcaacaatgggagcagcatcaatgac attgacagttcaagcaagattgttgttgtcaggaattgttcaacaacagaataatttgttgagagcaattgaagcacaacaaagaatgttgcaat tgacagtttggggaattaaacaattgcaagcaagagtgttggcagttgaaagatatttgggagatcaacaattgttgggaatttggggatgttc aggaaagttgatttgtacaacagcagttccatggaatgcatcatggtcaaataaatcattggatagaatttggaataatatgacatggatggaat gggaaagagaaattgataattatacatcagaaatttatacattgattgaagaatcacagaatcaacaagagaagaatgaacaagaattgttgg aattggataaatgggcatcattgtggaattggtttgatattactaaatggttgtggtatattaaatcatcaattgcatcattcttattattattggattg attattggattgttcttggtgttgagagttggaatttatttgtgtattaaattgaaacatacaaagaagagacaaatttatacagatattgaaatgaat agattgggaaagtgagctcaaatcctgcacaacagattcttcatgtttgaaccaaatcaacttgtgatatcatgctcaaagaggccttaattaa SEQ 6: VSV $G_{IN}$CT1 sequences
Sequence key
Transmembrane domain (SEQ ID NO: 3)
Single amino acid C-tail (SEQ ID NO: 38)
Protein (SEQ ID NO: 37)

mkcllylaflfigvnckftivfphnqkgnwknvpsnyhycpsssdlnwhndligtalqvkmpkshkaiqadgwmchaskwvttcd frwygpkyithsirsftpsveqckesieqtkqgtwlnpgfppqscgyatvtdaeaaivqvtphhvlvdeytgewvdsqfingkcsndi cptvhnsttwhsdykvkglcdsnlismditffsedgelsslgkegtgfrsnyfayetgdkackmqyckhwgvrlpsgvwfemadkd lfaaarfpecpegssisapsqtsvdvsliqdverildyslcqetwskiraglpispvdlsylapknpgtgpvftiingtlkyfetryirvdiaa pilsrmvgmisgttterelwddwapyedveigpngvlrtssgykfplymighgmldsdlhlsskaqvfehphiqdaasqlpddetlff gdtglsknpiefvegwfsswkssiasfffiigliiglflvlr*

Transmembrane domain (SEQ ID NO: 7)
Nucleotide coding single amino acid C-tail (SEQ ID NO: 40)
Nucleotide (SEQ ID NO: 39)

atgaagtgccttttgtacttagctttttttattcatcggggtgaattgcaagttcaccatagtttttccacacaaccaaaaaggaaactggaaaaatg ttccttccaattaccattattgcccgtcaagctcagatttaaattggcataatgacttaataggcacagccttacaagtcaaaatgcccaagagtc -continued

```
acaaggctattcaagcagacggttggatgtgtcatgcttccaaatgggtcactacttgtgatttccgctggtacggaccgaagtatataacaca ttccatccgatccttcactccatctgtagaacaatgcaaggaaagcattgaacaaacgaaacaaggaacttggctgaatccaggcttccctcc tcaaagttgtggatatgcaactgtgacggatgctgaagcagcgattgtccaggtgactcctcaccatgtgcttgttgatgaatacacaggaga atggttgattcacagttcatcaacggaaaatgcagcaatgacatatgccccactgtccataactccacaacctggcattccgactataaggt caaagggctatgtgattctaacctcatttccatggacatcaccttcttacagaggacggagagctatcatccctaggaaaggagggcacag ggttcagaagtaactactttgcttatgaaactggagacaaggcctgcaaaatgcagtactgcaagcattggggagtcagactcccatcaggt gtaggttcgagatggctgataaggatctctttgctgcagccagattccctgaatgcccagaagggtcaagtatctctgctccatctcagacct cagtggatgtaagtctcattcaggacgttgagaggatcttggattattccctctgccaagaaacctggagcaaaatcagagcgggtcttccca tctctccagtggatctcagctatcttgctcctaaaaacccaggaaccggtcctgtctttaccataatcaatggtaccctaaaatactttgagacca gatacatcagagtcgatattgctgaccaatcctacaagaatggtcggaatgatcagtggaactaccacagaaagggaactgtgggatgac tgggctccatatgaagacgtggaaattggacccaatggagttctgaggaccagttcaggatataagtttcctttatatatgattggacatggtat gttggactccgatcttcatcttagctcaaaggctcaggtgtttgaacatcctcacattcaagacgctgcttcgcagcttcctgatgatgagacttt attttttggtgatactgggctatccaaaaatccaatcgagtttgtagaaggttggttcagtagttggaagagctctattgcctcttttttctttatcata gggttaatcattggactattcttggttctccgataa
```

CITATIONS

1. Albertini, A. A., E. Baquero, A. Ferlin, and Y. Gaudin. 2012. Molecular and cellular aspects of rhabdovirus entry. Viruses 4:117-139.
2. Ball, L. A., C. R. Pringle, B. Flanagan, V. P. Perepelitsa, and G. W. Wertz. 1999. Phenotypic consequences of rearranging the P, M, and G genes of vesicular stomatitis virus. J Virol 73:4705-4712.
3. Barr, J. N., S. P. Whelan, and G. W. Wertz. 2002. Transcriptional control of the RNA-dependent RNA polymerase of vesicular stomatitis virus. Biochim Biophys Acta 1577:337-353.
4. Clarke, D. K., D. Cooper, M. A. Egan, R. M. Hendry, C. L. Parks, and S. A. Udem. 2006. Recombinant vesicular stomatitis virus as an HIV-1 vaccine vector. Springer seminars in immunopathology 28:239-253.
5. Conzelmann, K. K. 2004. Reverse genetics of mononegavirales. Curr Top Microbiol Immunol 283:1-41.
6. Cronin, J., X. Y. Zhang, and J. Reiser. 2005. Altering the tropism of lentiviral vectors through pseudotyping. Current gene therapy 5:387-398.
7. Forsell, M. N., G. M. McInerney, P. Dosenovic, A. S. Hidmark, C. Eriksson, P. Liljestrom, C. Grundner, and G. B. Karlsson Hedestam. 2007. Increased human immunodeficiency virus type 1 Env expression and antibody induction using an enhanced alphavirus vector. J Gen Virol 88:2774-2779.
8. Hangartner, L., R. M. Zinkernagel, and H. Hengartner. 2006. Antiviral antibody responses: the two extremes of a wide spectrum. Nature reviews. Immunology 6:231-243.
9. Johnson, J. E., W. Rodgers, and J. K. Rose. 1998. A plasma membrane localization signal in the HIV-1 envelope cytoplasmic domain prevents localization at sites of vesicular stomatitis virus budding and incorporation into VSV virions. Virology 251:244-252.
10. Kahn, J. S., M. J. Schnell, L. Buonocore, and J. K. Rose. 1999. Recombinant vesicular stomatitis virus expressing respiratory syncytial virus (RSV) glycoproteins: RSV fusion protein can mediate infection and cell fusion. Virology 254:81-91.
11. Keenan, R. J., D. M. Freymann, R. M. Stroud, and P. Walter. 2001. The signal recognition particle. Annual review of biochemistry 70:755-775.
12. Kretzschmar, E., L. Buonocore, M. J. Schnell, and J. K. Rose. 1997. High-efficiency incorporation of functional influenza virus glycoproteins into recombinant vesicular stomatitis viruses. J Virol 71:5982-5989.
13. Lawson, N. D., E. A. Stillman, M. A. Whitt, and J. K. Rose. 1995. Recombinant vesicular stomatitis viruses from DNA. Proceedings of the National Academy of Sciences of the United States of America 92:4477-4481.
14. Letchworth, G. J., L. L. Rodriguez, and J. Del cbarrera. 1999. Vesicular stomatitis. Vet J 157:239-260.
15. Lyles, D., and C. Rupprecht. 2007. Rhabdoviridae, p. 1363-1408. In D. M. Knipe, D. E. Griffin, R. A. Lamb, S. E. Straus, P. M. Howley, M. A. Martin, B. Roizman, and S. E. Straus (ed.), Fields virology, vol. 1. Wolters Kluwer, Philadelphia.
16. Mebatsion, T., and K. K. Conzelmann. 1996. Specific infection of CD4+ target cells by recombinant rabies virus pseudotypes carrying the HIV-1 envelope spike protein. Proceedings of the National Academy of Sciences of the United States of America 93:11366-11370.
17. Owens, R. J., and J. K. Rose. 1993. Cytoplasmic domain requirement for incorporation of a foreign envelope protein into vesicular stomatitis virus. J Virol 67:360-365.
18. Quinones-Kochs, M. I., M. J. Schnell, L. Buonocore, and J. K. Rose. 2001. Mechanisms of loss of foreign gene expression in recombinant vesicular stomatitis viruses. Virology 287:427-435.
19. Roberts, A., L. Buonocore, R. Price, J. Forman, and J. K. Rose. 1999. Attenuated vesicular stomatitis viruses as vaccine vectors. J Virol 73:3723-3732.
20. Rose, N. F., P. A. Marx, A. Luckay, D. F. Nixon, W. J. Moretto, S. M. Donahoe, D. Montefiori, A. Roberts, L. Buonocore, and J. K. Rose. 2001. An effective AIDS vaccine based on live attenuated vesicular stomatitis virus recombinants. Cell 106:539-549.
21. Rose, N. F., A. Roberts, L. Buonocore, and J. K. Rose. 2000. Glycoprotein exchange vectors based on vesicular stomatitis virus allow effective boosting and generation of neutralizing antibodies to a primary isolate of human immunodeficiency virus type 1. J Virol 74:10903-10910.
22. Sanders, R. W., M. M. Dankers, E. Busser, M. Caffrey, J. P. Moore, and B. Berkhout. 2004. Evolution of the HIV-1 envelope glycoproteins with a disulfide bond between gp120 and gp41. Retrovirology 1:3.
23. Sanders, R. W., L. Schiffner, A. Master, F. Kajumo, Y. Guo, T. Dragic, J. P. Moore, and J. M. Binley. 2000. Variable-loop-deleted variants of the human immunodeficiency virus type 1 envelope glycoprotein can be stabilized by an intermolecular disulfide bond between the gp120 and gp41 subunits. J Virol 74:5091-5100.
24. Schnell, M. J., L. Buonocore, E. Boritz, H. P. Ghosh, R. Chemish, and J. K. Rose. 1998. Requirement for a non-specific glycoprotein cytoplasmic domain sequence to drive efficient budding of vesicular stomatitis virus. Embo J 17:1289-1296.
25. Schnell, M. J., L. Buonocore, E. Kretzschmar, E. Johnson, and J. K. Rose. 1996. Foreign glycoproteins expressed from recombinant vesicular stomatitis viruses are incorporated efficiently into virus particles. Proceedings of the National Academy of Sciences of the United States of America 93:11359-11365.
26. Schnell, M. J., T. Mebatsion, and K. K. Conzelmann. 1994. Infectious rabies viruses from cloned cDNA. Embo J 13:4195-4203.
27. Vlad, A. M., and O. J. Finn. 2004. Glycoprotein tumor antigens for immunotherapy of breast cancer. Breast Dis 20:73-79.
28. Whelan, S. P., L. A. Ball, J. N. Barr, and G. T. Wertz. 1995. Efficient recovery of infectious vesicular stomatitis virus entirely from cDNA clones. Proceedings of the National Academy of Sciences of the United States of America 92:8388-8392.
29. Wyatt, L. S., I. M. Belyakov, P. L. Earl, J. A. Berzofsky, and B. Moss. 2008. Enhanced cell surface expression, immunogenicity and genetic stability resulting from a spontaneous truncation of HIV Env expressed by a recombinant MVA. Virology 372:260-272.

The invention is further described by the following numbered paragraphs:

1. A recombinant vesicular stomatitis virus (VSV) vector wherein the gene encoding the VSV surface glycoprotein G (VSV G) is functionally replaced by HIV Env.
2. The vector of paragraph 1 wherein the HIV Env is recognized by antibodies PG9, PG16, 2G12, b12, 2F5, 4E10 or Z13, or other Env-specific antibodies, including broad potent neutralizing trimer-specific antibodies.
3. A recombinant vesicular stomatitis virus (VSV) vector encoding a modified form of VSV G, wherein the modified form of VSV G harbors epitopes from the HIV Env membrane proximal external region (MPER).
4. The vector of paragraph 3 wherein the MPER sequence is inserted into the membrane proximal region of VSV G.
5. The vector of paragraph 3 or 4 wherein a G-MPER protein binds with high avidity to 2F5 and 4E10 monoclonal antibodies.
6. A recombinant vesicular stomatitis virus (VSV) vector encoding a N-terminally truncated form of VSV G (G/Stem), wherein the G/Stem presents Env epitope sequences on the surface of VSV particles.
7. The vector of paragraph 6 wherein G/Stem contains a cytoplasmic tail (CT) and trans-membrane (TM) spanning domains of G, a membrane proximal extracellular polypeptide (the Stem) that can be 0 to 16 to 68 amino acids in, wherein HIV Env epitopes are appended to the Stem.
8. The vector of paragraph 7 wherein the HIV Env epitopes are MPER epitopes.
9. The vector of paragraph 8 wherein the G/Stem-MPER molecules bind to 2F5 10 and 4E10 monoclonal antibodies with high affinity.
10. The vector of any one of paragraphs 1-9 wherein the HIV Env is a mutant HIV Env.
11. A method of generating novel chimeric EnvG molecules expressed and incorporated into VSV comprising:
    (a) serially passaging replication-competent chimeric VSV-HIV viruses that lack the capacity to encode wild-type G and are dependent on EnvG for infection and propagation on cells to promote emergence of viruses with greater replicative fitness and
    (b) identifying novel mutations that enhance Env or EnvG function.
12. The method of paragraph 11, wherein the cells are CD4/CCR5+ cells.
13. The method of paragraph 11 or 12 wherein the novel mutations escalate trimer abundance on the virus particle and/or increase the stability of the functional trimeric form of Env or a chimeric EnvG.
14. The method of paragraph 11, 12 or 13 further comprising determining whether the Env or EnvG immunogens elicit broadly neutralizing anti-Env antibodies.
15. The method of paragraph 11, 12, 13 or 14 further comprising applying selective pressure to generate novel Env or EnvG molecules expressed and incorporated into VSV, wherein the selective pressure is binding to an antibody of interest.
16. The method of paragraph 15 wherein the antibody is PG9, PG16, b12, 2G12, 2F5 or 4E10 or any other broad potent neutralizing Env trimer specific antibody.
17. A method of producing an immune response comprising administering to a mammal the vector of any one of paragraphs 1-10.
18. A method of eliciting an immune response comprising administering to a mammal the vector of any one of paragraphs 1-10.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A recombinant vesicular stomatitis virus (VSV) vector encoding and expressing a membrane-anchored HIV Env immunogen and a natural VSV attachment protein (G) (EnvG) chimera, wherein the genes in the VSV vector are arranged sequentially in the order 3'-N-P-M-EnvG-L-G-5'.

2. The vector of claim 1, wherein the G gene is transferred to a 5'-terminal position in the negative-sense RNA genome of the recombinant VSV vector.

3. The vector of claim 1, wherein the vector comprises a sequence selected from the group consisting of SEQ ID NO: 5 and SEQ ID NO: 6.

4. The vector of claim 1, wherein the vector expresses a sequence selected from the group consisting of SEQ ID NO: 1, SEQ ID NO: 3 and SEQ ID NO: 4.

5. The vector of claim 1, wherein the EnvG chimera comprises a truncated cytoplasmic tail.

6. The vector of claim 2, wherein the EnvG chimera comprises a truncated cytoplasmic tail.

7. A method of producing an immune response or eliciting an immune response comprising administering to a mammal the vector of claim 1.

* * * * *

SEQUENCE LISTING

<160> NUMBER OF SEQ ID NOS: 55

<210> SEQ ID NO 1
<211> LENGTH: 719
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 1

Met Lys Cys Leu Leu Tyr Leu Ala Phe Leu Phe Ile Gly Val Asn Cys
1               5                   10                  15

Lys Ala Ser Ala Glu Asn Leu Trp Val Thr Val Tyr Tyr Gly Val Pro
            20                  25                  30

Val Trp Lys Asp Ala Glu Thr Thr Leu Phe Cys Ala Ser Asp Ala Lys
        35                  40                  45

Ala Tyr Glu Thr Glu Lys His Asn Val Trp Ala Thr His Ala Cys Val
    50                  55                  60

Pro Thr Asp Pro Asn Pro Gln Glu Ile His Leu Glu Asn Val Thr Glu
65                  70                  75                  80

Glu Phe Asn Met Trp Lys Asn Asn Met Val Glu Gln Met His Thr Asp
                85                  90                  95

Ile Ile Ser Leu Trp Asp Gln Ser Leu Lys Pro Cys Val Lys Leu Thr
            100                 105                 110

Pro Leu Cys Val Thr Leu Gln Cys Thr Asn Val Thr Asn Asn Ile Thr
        115                 120                 125

Asp Asp Met Arg Gly Glu Leu Lys Asn Cys Ser Phe Asn Met Thr Thr
    130                 135                 140

Glu Leu Arg Asp Lys Lys Gln Lys Val Tyr Ser Leu Phe Tyr Arg Leu
145                 150                 155                 160

Asp Val Val Gln Ile Asn Glu Asn Gln Gly Asn Arg Ser Asn Asn Ser
                165                 170                 175

Asn Lys Glu Tyr Arg Leu Ile Asn Cys Asn Thr Ser Ala Ile Thr Gln
            180                 185                 190

Ala Cys Pro Lys Val Ser Phe Glu Pro Ile Pro Ile His Tyr Cys Ala
        195                 200                 205

Pro Ala Gly Phe Ala Ile Leu Lys Cys Lys Asp Lys Lys Phe Asn Gly
    210                 215                 220

Thr Gly Pro Cys Pro Ser Val Ser Thr Val Gln Cys Thr His Gly Ile
225                 230                 235                 240

Lys Pro Val Val Ser Thr Gln Leu Leu Leu Asn Gly Ser Leu Ala Glu
                245                 250                 255

Glu Glu Val Met Ile Arg Ser Glu Asn Ile Thr Asn Asn Ala Lys Asn
            260                 265                 270

Ile Leu Val Gln Phe Asn Thr Pro Val Gln Ile Asn Cys Thr Arg Pro
        275                 280                 285

Asn Asn Asn Thr Arg Lys Ser Ile Arg Ile Gly Pro Gly Gln Ala Phe
    290                 295                 300

Tyr Ala Thr Gly Asp Ile Ile Gly Asp Ile Arg Gln Ala His Cys Thr
305                 310                 315                 320

Val Ser Lys Ala Thr Trp Asn Glu Thr Leu Gly Lys Val Val Lys Gln
                325                 330                 335

Leu Arg Lys His Phe Gly Asn Asn Thr Ile Ile Arg Phe Ala Asn Ser
            340                 345                 350

Ser Gly Gly Asp Leu Glu Val Thr Thr His Ser Phe Asn Cys Gly Gly
        355                 360                 365

Glu Phe Phe Tyr Cys Asn Thr Ser Gly Leu Phe Asn Ser Thr Trp Ile
    370                 375                 380
```

```
Ser Asn Thr Ser Val Gln Gly Ser Asn Ser Thr Gly Ser Asn Asp Ser
385                 390                 395                 400

Ile Thr Leu Pro Cys Arg Ile Lys Gln Ile Ile Asn Met Trp Gln Arg
            405                 410                 415

Ile Gly Gln Ala Met Tyr Ala Pro Pro Ile Gln Gly Val Ile Arg Cys
            420                 425                 430

Val Ser Asn Ile Thr Gly Leu Ile Leu Thr Arg Asp Gly Gly Ser Thr
            435                 440                 445

Asn Ser Thr Thr Glu Thr Phe Arg Pro Gly Gly Gly Asp Met Arg Asp
    450                 455                 460

Asn Trp Arg Ser Glu Leu Tyr Lys Tyr Lys Val Val Lys Ile Glu Pro
465                 470                 475                 480

Leu Gly Val Ala Pro Thr Arg Ala Lys Arg Arg Val Val Gly Arg Glu
            485                 490                 495

Lys Arg Ala Val Gly Ile Gly Ala Val Phe Leu Gly Phe Leu Gly Ala
            500                 505                 510

Ala Gly Ser Thr Met Gly Ala Ala Ser Met Thr Leu Thr Val Gln Ala
            515                 520                 525

Arg Asn Leu Leu Ser Gly Ile Val Gln Gln Gln Ser Asn Leu Leu Arg
530                 535                 540

Ala Ile Glu Ala Gln Gln His Leu Leu Lys Leu Thr Val Trp Gly Ile
545                 550                 555                 560

Lys Gln Leu Gln Ala Arg Val Leu Ala Val Glu Arg Tyr Leu Arg Asp
            565                 570                 575

Gln Gln Leu Leu Gly Ile Trp Gly Cys Ser Gly Lys Leu Ile Cys Thr
            580                 585                 590

Thr Asn Val Pro Trp Asn Ser Ser Trp Ser Asn Arg Asn Leu Ser Glu
            595                 600                 605

Ile Trp Asp Asn Met Thr Trp Leu Gln Trp Asp Lys Glu Ile Ser Asn
            610                 615                 620

Tyr Thr Gln Ile Ile Tyr Gly Leu Leu Glu Ser Gln Asn Gln Gln
625                 630                 635                 640

Glu Lys Asn Glu Gln Asp Leu Leu Ala Leu Asp Lys Trp Ala Ser Leu
            645                 650                 655

Trp Asn Trp Phe Asp Ile Ser Asn Trp Leu Trp Tyr Ile Lys Ser Ser
            660                 665                 670

Ile Ala Ser Phe Phe Phe Ile Ile Gly Leu Ile Gly Leu Phe Leu
            675                 680                 685

Val Leu Arg Val Gly Ile Tyr Leu Cys Ile Lys Leu Lys His Thr Lys
            690                 695                 700

Lys Arg Gln Ile Tyr Thr Asp Ile Glu Met Asn Arg Leu Gly Lys
705                 710                 715
```

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

```
Met Lys Cys Leu Leu Tyr Leu Ala Phe Leu Phe Ile Gly Val Asn Cys
1               5                   10                  15

Lys Ala Ser
```

```
<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Ser Ile Ala Ser Phe Phe Phe Ile Ile Gly Leu Ile Ile Gly Leu
1               5                   10                  15

Phe Leu Val Leu
            20

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Val Gly Ile Tyr Leu Cys Ile Lys Leu Lys His Thr Lys Lys Arg
1               5                   10                  15

Gln Ile Tyr Thr Asp Ile Glu Met Asn Arg Leu Gly Lys
            20                  25

<210> SEQ ID NO 5
<211> LENGTH: 2160
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgaagtgcc ttttgtactt agcttttttta ttcatcgggg tgaattgcaa ggctagcgca      60
gagaatttgt gggtaacagt ctactatgga gtccctgtat ggaaggatgc agagacaaca     120
ttgttctgtg ctagtgacgc aaaggcttac gagacggaga agcacaatgt gtgggcaact     180
cacgcatgtg tcccaaccga tccaaatcct caagagattc atctagagaa tgtgactgaa     240
gaattcaata tgtggaagaa taatatggta gagcaaatgc atacagatat cattagttta     300
tgggaccagt cacttaaacc ctgcgttaaa ttgacgcctc tatgtgtgac acttcaatgt     360
actaatgtta caaacaacat aacagatgat atgagaggag aactgaagaa ctgtagtttc     420
aacatgacga cagagttgcg tgacaagaaa cagaaagtgt attcactatt ctatcggttg     480
gatgtagtac agataaatga gaatcaagga acaggtccaa caactctaa caaagagtac     540 agacttatta attgcaatac cagtgctatc acgcaagcct gcccaaaggt ttcatttgaa     600
ccaataccta ttcattattg tgcacctgct ggattcgcca tcctcaaatg taaagacaag     660
aagttcaatg gaacaggacc ctgcccatca gtttcaaccg ttcagtgcac ccacggaatc     720
aagcctgtag ttagtactca attattgtta atgggagct agctgaaga agaagttatg     780 attagatcag agaatattac caataatgcg aagaacatct ggttcaatt caatactcca     840 gtccagatca attgcacaag gcctaataat aataccagaa agagtataag aattgggcca     900
ggacaggcat ctatgcaac aggagatata atcggagaca ttcgacaagc gcactgcact     960
gtttctaagg ccacttggaa tgaaacattg ggtaaagttg taagcaact tcggaagcat    1020 ttcggaaata acacaattat tagatttgcg aactcatctg gaggggatct ggaagtgaca    1080
```

```
acacactctt tcaattgcgg tggcgagttc ttctattgta atacaagtgg attatttaac    1140
tctacttgga tttcaaatac ctcagtccaa ggatctaatt caacagggtc taacgattct    1200
ataacattac cttgccgtat aaagcaaatt attaatatgt ggcaaagaat cgggcaagcg    1260
atgtatgctc cacctattca aggcgtgatt cgttgcgttt caaacataac agggttgatc    1320
ctgaccaggg atggaggctc taccaattcc accaccgaga ccttccgtcc cggtggcgga    1380
gatatgcggg ataactggag atcagagctc tataagtata aggttgtgaa gattgaacct    1440
cttggagttg cccctacaag agcaaagaga agggtggttg gccgagagaa gagagcagtt    1500
ggcatcggtg ctgtctttct cggatttctt ggagcagctg gatccactat gggagcagca    1560
tcaatgacac taacagtgca ggctagaaat ttgcttagcg gaatcgttca gcagcagagc    1620
aatttactaa gagcaattga agcacagcaa catctcttaa agttgacggt gtggggcatt    1680
aaacaactac aagcgagagt gcttgccgtc gaaagatatt tgcgagacca acagctattg    1740
ggtatttggg gttgttctgg gaaattaatt tgcacaacaa atgttccatg gaactcctcc    1800
tggagtaata ggaatttaag tgagatatgg gacaacatga catggttgca gtgggacaag    1860
gaaatctcaa attatacaca gataatctat ggattattag aagagtctca gaatcagcaa    1920
gagaagaatg aacaggattt gcttgcattg gataagtggg cttctctatg gaactggttc    1980
gatattagta attggctctg gtatattaag agctctattg cctcttttt ctttatcata    2040 gggttaatca ttggactatt cttggttctc cgagttggta tttatctttg cattaaatta    2100
aagcacacca gaaaagaca gatttataca gacatagaga tgaaccgact tggaaagtaa    2160
```

<210> SEQ ID NO 6
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
atgaagtgcc ttttgtactt agcttttta ttcatcgggg tgaattgcaa g               51

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agctctattg cctcttttt ctttatcata gggttaatca ttggactatt cttggttctc      60

<210> SEQ ID NO 8
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cgagttggta tttatctttg cattaaatta aagcacacca gaaaagaca gatttataca      60 gacatagaga tgaaccgact tggaaag                                        87

```
<210> SEQ ID NO 9
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Cys Leu Leu Tyr Leu Ala Phe Leu Phe Ile Gly Val Asn Cys
1               5                   10                  15

Lys Ser Gly Glu Leu Leu Glu Leu Asp Lys Trp Ala Ser Leu Trp Asn
            20                  25                  30

Trp Phe Asp Ile Thr Lys Trp Leu Trp Tyr Ile Lys Ser Gly Gly Tyr
        35                  40                  45

Lys Phe Pro Leu Tyr Met Ile Gly His Gly Met Leu Asp Ser Asp Leu
    50                  55                  60

His Leu Ser Ser Lys Ala Gln Val Phe Glu His Pro His Ile Gln Asp
65                  70                  75                  80

Ala Ala Ser Gln Leu Pro Asp Asp Glu Thr Leu Phe Phe Gly Asp Thr
                85                  90                  95

Gly Leu Ser Lys Asn Pro Ile Glu Phe Val Glu Gly Trp Phe Ser Ser
            100                 105                 110

Trp Lys Ser Ser Ile Ala Ser Phe Phe Ile Ile Gly Leu Ile Ile
        115                 120                 125

Gly Leu Phe Leu Val Leu Arg Val Gly Ile Tyr Leu Cys Ile Lys Leu
    130                 135                 140

Lys His Thr Lys Lys Arg Gln Ile Tyr Thr Asp Ile Glu Met Asn Arg
145                 150                 155                 160

Leu Gly Lys

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Lys Cys Leu Leu Tyr Leu Ala Phe Leu Phe Ile Gly Val Asn Cys
1               5                   10                  15

Lys

<210> SEQ ID NO 11
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Leu Leu Glu Leu Asp Lys Trp Ala Ser Leu Trp Asn Trp Phe Asp
1               5                   10                  15

Ile Thr Lys Trp Leu Trp Tyr Ile Lys
            20                  25
```

<210> SEQ ID NO 12
<211> LENGTH: 492
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
atgaagtgcc tactttacct tgcatttctc tttatcggag ttaattgcaa atccggagag      60
ctcctcgaat tggataaatg ggcaagccta tggaactggt ttgacattac gaaatggttg     120
tggtacatta agtccggagg ttataaattc cctttatata tgattggaca cggcatgctg     180
gattcagacc ttcacctctc atcaaaggcc caggtgtttg agcatcctca cattcaggat     240
gctgcttcac agctaccgga tgacgaaact ctcttcttcg gagacaccgg tttatctaag     300
aatcctatag agttcgtgga agggtggttc tcctcttgga agtcgtccat cgcaagcttc     360
ttcttcataa taggtctcat tattggactc tttcttgtcc tgagagtcgg aatatatcta     420
tgtatcaagc tcaaacatac aaagaagagg cagatctata cagatattga aatgaatcga     480
ttagggaaat aa                                                         492
```

<210> SEQ ID NO 13
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

```
atgaagtgcc tactttacct tgcatttctc tttatcggag ttaattgcaa a              51
```

<210> SEQ ID NO 14
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

```
gagctcctcg aattggataa atgggcaagc ctatggaact ggtttgacat tacgaaatgg     60
ttgtggtaca ttaag                                                      75
```

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

```
tcgtccatcg caagcttctt cttcataata ggtctcatta ttggactctt tcttgtcctg     60
```

<210> SEQ ID NO 16
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 16
agagtcggaa tatatctatg tatcaagctc aaacatacaa agaagaggca gatctataca    60
gatattgaaa tgaatcgatt agggaaa                                        87

<210> SEQ ID NO 17
<211> LENGTH: 724
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17
```

Met Pro Met Gly Ser Leu Gln Pro Leu Ala Thr Leu Tyr Leu Leu Gly
1               5                   10                  15

Met Leu Val Ala Ser Val Leu Ala Ala Gly Asn Leu Trp Val Thr Val
            20                  25                  30

Tyr Tyr Gly Val Pro Val Trp Lys Glu Ala Lys Thr Thr Leu Phe Cys
        35                  40                  45

Ala Ser Asp Ala Lys Ala Tyr Glu Lys Glu Val His Asn Val Trp Ala
    50                  55                  60

Thr His Ala Cys Val Pro Thr Asp Pro Asn Pro Gln Glu Met Val Leu
65                  70                  75                  80

Glu Asn Val Thr Glu Asn Phe Asn Met Trp Lys Asn Asp Met Val Glu
                85                  90                  95

Gln Met His Glu Asp Val Ile Ser Leu Trp Asp Gln Ser Leu Lys Pro
            100                 105                 110

Cys Val Lys Leu Thr Pro Leu Cys Val Thr Leu Glu Cys Arg Gln Val
        115                 120                 125

Asn Thr Thr Asn Ala Thr Ser Ser Val Asn Val Thr Asn Gly Glu Glu
    130                 135                 140

Ile Lys Asn Cys Ser Phe Asn Ala Thr Thr Glu Ile Arg Asp Lys Lys
145                 150                 155                 160

Gln Lys Val Tyr Ala Leu Phe Tyr Arg Leu Asp Ile Val Pro Leu Glu
                165                 170                 175

Glu Glu Arg Lys Gly Asn Ser Ser Lys Tyr Arg Leu Ile Asn Cys Asn
            180                 185                 190

Thr Ser Ala Ile Thr Gln Ala Cys Pro Lys Val Thr Phe Asp Pro Ile
        195                 200                 205

Pro Ile His Tyr Cys Ala Pro Ala Gly Tyr Ala Ile Leu Lys Cys Asn
    210                 215                 220

Asn Lys Thr Phe Asn Gly Thr Gly Pro Cys Asn Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Gly Glu Ile Ile Ile Arg Ser Glu Asn Leu
            260                 265                 270

Thr Asn Asn Val Lys Thr Ile Ile Val His Leu Asn Glu Ser Val Glu
        275                 280                 285

Ile Val Cys Thr Arg Pro Asn Asn Asn Thr Arg Lys Ser Ile Arg Ile
    290                 295                 300

Gly Pro Gly Gln Thr Phe Tyr Ala Thr Gly Asp Ile Ile Gly Asn Ile
305                 310                 315                 320

Arg Gln Ala Tyr Cys Asn Ile Lys Lys Asp Asp Trp Ile Arg Thr Leu
                325                 330                 335

```
Gln Arg Val Gly Lys Lys Leu Ala Glu His Phe Pro Arg Arg Ile Ile
                340                 345                 350

Asn Phe Thr Ser Pro Ala Gly Gly Asp Leu Glu Ile Thr Thr His Ser
            355                 360                 365

Phe Asn Cys Arg Gly Glu Phe Phe Tyr Cys Asn Thr Ser Ser Leu Phe
370                 375                 380

Asn Ser Thr Tyr Asn Pro Asn Asp Thr Asn Ser Asn Ser Ser Ser Ser
385                 390                 395                 400

Asn Ser Ser Leu Asp Ile Thr Ile Pro Cys Arg Ile Lys Gln Ile Ile
                405                 410                 415

Asn Met Trp Gln Glu Val Gly Arg Ala Met Tyr Ala Pro Pro Ile Glu
            420                 425                 430

Gly Asn Ile Thr Cys Lys Ser Asn Ile Thr Gly Leu Leu Leu Val Arg
435                 440                 445

Asp Gly Gly Val Glu Ser Asn Glu Thr Glu Ile Phe Arg Pro Gly Gly
            450                 455                 460

Gly Asp Met Arg Asn Asn Trp Arg Ser Glu Leu Tyr Lys Tyr Lys Val
465                 470                 475                 480

Val Glu Ile Lys Pro Leu Gly Ile Ala Pro Thr Ala Ala Lys Arg Arg
                485                 490                 495

Val Val Glu Arg Glu Lys Arg Ala Val Gly Leu Gly Ala Val Ile Phe
            500                 505                 510

Gly Phe Leu Gly Ala Ala Gly Ser Thr Met Gly Ala Ala Ser Ile Thr
            515                 520                 525

Leu Thr Val Gln Ala Arg Gln Leu Leu Ser Gly Ile Val Gln Gln Gln
530                 535                 540

Ser Asn Leu Leu Lys Ala Ile Glu Ala Gln Gln His Leu Leu Gln Leu
545                 550                 555                 560

Thr Val Trp Gly Ile Lys Gln Leu Gln Thr Arg Val Leu Ala Ile Glu
                565                 570                 575

Arg Tyr Leu Lys Asp Gln Gln Leu Leu Gly Ile Trp Gly Cys Ser Gly
            580                 585                 590

Lys Leu Ile Cys Thr Thr Ala Val Pro Trp Asn Ser Ser Trp Ser Asn
            595                 600                 605

Lys Ser His Asp Glu Ile Trp Gly Asn Met Thr Trp Met Gln Trp Asp
610                 615                 620

Arg Glu Ile Ser Asn Tyr Thr Asn Thr Ile Tyr Arg Leu Leu Glu Asp
625                 630                 635                 640

Ser Gln Asn Gln Gln Glu Gln Asn Glu Lys Asp Leu Leu Ala Leu Asp
                645                 650                 655

Ser Trp Glu Asn Leu Trp Asn Trp Phe Ser Ile Thr Lys Trp Leu Trp
            660                 665                 670

Tyr Ile Lys Ser Ser Ile Ala Ser Phe Phe Phe Ile Ile Gly Leu Ile
            675                 680                 685

Ile Gly Leu Phe Leu Val Leu Arg Val Gly Ile Tyr Leu Cys Ile Lys
            690                 695                 700

Leu Lys His Thr Lys Lys Arg Gln Ile Tyr Thr Asp Ile Glu Met Asn
705                 710                 715                 720

Arg Leu Gly Lys

<210> SEQ ID NO 18
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 18

Met Pro Met Gly Ser Leu Gln Pro Leu Ala Thr Leu Tyr Leu Leu Gly
1               5                   10                  15

Met Leu Val Ala Ser Val Leu Ala Ala
            20                  25

<210> SEQ ID NO 19
<211> LENGTH: 2175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
```

| | | | | |
|---|---|---|---|---|
| atgccaatgg | gatcattgca | accattggca | acattgtatt | tgttgggaat | gttggttgca |    60 |
| tcagttttgg | cagcagggaa | tttatgggtt | actgtatatt | acggagttcc | tgtttggaaa |   120 |
| gaagccaaga | ccacattatt | ctgtgctagt | gacgctaagg | cttacgagaa | agaagtgcat |   180 |
| aacgtttggg | caacacatgc | gtgtgtacct | accgacccaa | atcctcaaga | aatggtactt |   240 |
| gaaaatgtaa | ccgaaaattt | taacatgtgg | aagaatgata | tggttgaaca | gatgcatgaa |   300 |
| gatgtcatta | gcctatggga | tcaatctcta | aagccatgtg | taaagctcac | gcctttgtgt |   360 |
| gttactctcg | aatgcagaca | ggtcaacacg | acaaatgcaa | catcttcagt | taatgtaacc |   420 |
| aacggagagg | aaattaagaa | ttgtagcttt | aatgctacca | ctgaaattcg | tgataagaag |   480 |
| caaaaggtgt | atgcattatt | ttaccgattg | gatattgtgc | ctttggaaga | gagcgaaag |   540 |
| ggcaactctt | ccaaatacag | attaatcaac | tgcaacacaa | gcgcgattac | gcaagcttgt |   600 |
| ccaaaagtca | ccttcgaccc | catcccaatc | cattactgtg | cacctgccgg | atacgcaatt |   660 |
| cttaaatgta | ataataagac | ttttaatgga | acaggcccat | gtaataatgt | gtctacagta |   720 |
| cagtgtaccc | acggcatcaa | accggttgtt | tctacacagt | tgctcttaaa | tgggtcattg |   780 |
| gctgaaggag | agattattat | tcggtctgaa | aacctcacca | ataatgtaaa | gactatcatc |   840 |
| gttcacttga | acgaatctgt | ggagattgtc | tgtactagac | caaataataa | taccagaaag |   900 |
| tcaattagaa | taggacctgg | acaaactttc | tacgccacgg | gcgatattat | tgggaatatt |   960 |
| agacaagcat | attgcaacat | taagaaagat | gattggataa | gaacattgca | gcgggttggg |  1020 |
| aagaaattgg | ccgaacattt | ccccagaaga | ataatcaact | ttacatcacc | tgcaggagga |  1080 |
| gatttagaaa | ttacaacgca | ttcatttaac | tgtagagggg | agttcttcta | ttgtaataca |  1140 |
| tcttccttgt | tcaattctac | ctacaatcct | aatgatacca | atagtaattc | atcctcgtcg |  1200 |
| aattcttccc | tggatattac | aattccatgt | aggatcaaac | aaatcattaa | tatgtggcaa |  1260 |
| gaagtcggta | gagcgatgta | cgcacctccc | attgaaggaa | atattacatg | caagagcaat |  1320 |
| attacgggcc | tgttgctcgt | tcgagatggt | ggagtcgaat | ccaatgaaac | agagatcttc |  1380 |
| cgtcctggag | gagggatat | gagaaataat | tggagatctg | aactctataa | atacaaagta |  1440 |
| gtggaaatta | accattagg | gatagcaccg | acggcagcta | aagacgagt | ggtggagcgg |  1500 |
| gagaagcgtg | ctgttggatt | gggagccgtc | atatttgggt | ttctcggagc | tgcaggatct |  1560 |
| acaatgggtg | cggcatcgat | tacacttaca | gtgcaagcaa | ggcaattact | tagtggaata |  1620 |
| gttcaacaac | aatcaaatct | gctgaaagcc | attgaggcac | aacagcatct | gctacaattg |  1680 |

-continued

```
acagtgtggg gaatcaaaca attacagact agagttcttg caatcgaaag atatttaaag   1740
gaccaacaac tcttgggcat ttggggatgt tcgggaaagc ttatatgtac aacagcagta   1800
ccatggaact cttcttggtc aacaaatca cacgacgaga tttggggtaa tatgacctgg    1860
atgcaatggg atagagagat ttctaattac acaaatacca tctatagatt gcttgaagat   1920
tctcaaaatc agcaagagca gaacgagaaa gatttattag cactcgatag ttgggagaat   1980
ttgtggaatt ggttttcaat taccaagtgg ctctggtaca taaagtcgtc catcgcaagc   2040
ttcttcttca taataggtct cattattgga ctctttcttg tcctgagagt cggaatatat   2100
ctatgtatca agctcaaaca tacaaagaag aggcagatct atacagatat tgaaatgaat   2160
cgattaggga agtaa                                                    2175
```

<210> SEQ ID NO 20
<211> LENGTH: 75
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20

```
atgccaatgg gatcattgca accattggca acattgtatt tgttgggaat gttggttgca   60
tcagttttgg cagca                                                    75
```

<210> SEQ ID NO 21
<211> LENGTH: 89
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21

```
agagtcggaa tatatctatg tatcaagctc aaacatacaa gaagaggca gatctataca    60 gatattgaaa tgaatcgatt agggaagta                                     89
```

<210> SEQ ID NO 22
<211> LENGTH: 718
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

```
Met Pro Met Gly Ser Leu Gln Pro Leu Ala Thr Leu Tyr Leu Leu Gly
1               5                   10                  15

Met Leu Val Ala Ser Val Leu Ala Glu Lys Leu Trp Val Thr Val
            20                  25                  30

Tyr Tyr Gly Val Pro Val Trp Lys Glu Ala Thr Thr Thr Leu Phe Cys
        35                  40                  45

Ala Ser Asp Ala Lys Ala Tyr Asp Thr Glu Val His Asn Val Trp Ala
    50                  55                  60

Thr His Ala Cys Val Pro Thr Asp Pro Asn Pro Gln Glu Val Val Leu
65                  70                  75                  80

Glu Asn Val Thr Glu His Phe Asn Met Trp Lys Asn Asn Met Val Glu
                85                  90                  95

Gln Met Gln Glu Asp Ile Ile Ser Leu Trp Asp Gln Ser Leu Lys Pro
            100                 105                 110
```

```
Cys Val Lys Leu Thr Pro Leu Cys Val Thr Leu Asn Cys Lys Asp Val
            115                 120                 125

Asn Ala Thr Asn Thr Thr Asn Asp Ser Glu Gly Thr Met Glu Arg Gly
130                 135                 140

Glu Ile Lys Asn Cys Ser Phe Asn Ile Thr Thr Ser Ile Arg Asp Glu
145                 150                 155                 160

Val Gln Lys Glu Tyr Ala Leu Phe Tyr Lys Leu Asp Val Val Pro Ile
                165                 170                 175

Asp Asn Asn Asn Thr Ser Tyr Arg Leu Ile Ser Cys Asp Thr Ser Val
            180                 185                 190

Ile Thr Gln Ala Cys Pro Lys Ile Ser Phe Glu Pro Ile Pro Ile His
        195                 200                 205

Tyr Cys Ala Pro Ala Gly Phe Ala Ile Leu Lys Cys Asn Asp Lys Thr
    210                 215                 220

Phe Asn Gly Lys Gly Pro Cys Lys Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Glu Val Val Ile Arg Ser Asp Asn Phe Thr Asn Asn
            260                 265                 270

Ala Lys Thr Ile Ile Val Gln Leu Lys Glu Ser Val Glu Ile Asn Cys
        275                 280                 285

Thr Arg Pro Asn Asn Asn Thr Arg Lys Ser Ile His Ile Gly Pro Gly
    290                 295                 300

Arg Ala Phe Tyr Thr Thr Gly Glu Ile Ile Gly Asp Ile Arg Gln Ala
305                 310                 315                 320

His Cys Asn Ile Ser Arg Ala Lys Trp Asn Asp Thr Leu Lys Gln Ile
                325                 330                 335

Val Ile Lys Leu Arg Glu Gln Phe Glu Asn Lys Thr Ile Val Phe Asn
            340                 345                 350

His Ser Ser Gly Gly Asp Pro Glu Ile Val Met His Ser Phe Asn Cys
        355                 360                 365

Gly Gly Glu Phe Phe Tyr Cys Asn Ser Thr Gln Leu Phe Asn Ser Thr
    370                 375                 380

Trp Asn Asn Asn Thr Glu Gly Ser Asn Asn Thr Glu Gly Asn Thr Ile
385                 390                 395                 400

Thr Leu Pro Cys Arg Ile Lys Gln Ile Ile Asn Met Trp Gln Glu Val
                405                 410                 415

Gly Lys Ala Met Tyr Ala Pro Pro Ile Arg Gly Gln Ile Arg Cys Ser
            420                 425                 430

Ser Asn Ile Thr Gly Leu Leu Leu Thr Arg Asp Gly Gly Ile Asn Glu
        435                 440                 445

Asn Gly Thr Glu Ile Phe Arg Pro Gly Gly Gly Asp Met Arg Asp Asn
    450                 455                 460

Trp Arg Ser Glu Leu Tyr Lys Tyr Lys Val Val Lys Ile Glu Pro Leu
465                 470                 475                 480

Gly Val Ala Pro Thr Lys Ala Lys Arg Arg Val Val Gln Arg Glu Lys
                485                 490                 495

Arg Ala Val Gly Ile Gly Ala Val Phe Leu Gly Phe Leu Gly Ala Ala
            500                 505                 510

Gly Ser Thr Met Gly Ala Ala Ser Met Thr Leu Thr Val Gln Ala Arg
        515                 520                 525
```

```
Leu Leu Leu Ser Gly Ile Val Gln Gln Gln Asn Asn Leu Leu Arg Ala
        530                 535                 540

Ile Glu Ala Gln Gln Arg Met Leu Gln Leu Thr Val Trp Gly Ile Lys
545                 550                 555                 560

Gln Leu Gln Ala Arg Val Leu Ala Val Glu Arg Tyr Leu Gly Asp Gln
                565                 570                 575

Gln Leu Leu Gly Ile Trp Gly Cys Ser Gly Lys Leu Ile Cys Thr Thr
            580                 585                 590

Ala Val Pro Trp Asn Ala Ser Trp Ser Asn Lys Ser Leu Asp Arg Ile
        595                 600                 605

Trp Asn Asn Met Thr Trp Met Glu Trp Glu Arg Glu Ile Asp Asn Tyr
610                 615                 620

Thr Ser Glu Ile Tyr Thr Leu Ile Glu Glu Ser Gln Asn Gln Gln Glu
625                 630                 635                 640

Lys Asn Glu Gln Glu Leu Leu Glu Leu Asp Lys Trp Ala Ser Leu Trp
                645                 650                 655

Asn Trp Phe Asp Ile Thr Lys Trp Leu Trp Tyr Ile Lys Ser Ser Ile
            660                 665                 670

Ala Ser Phe Phe Phe Ile Ile Gly Leu Ile Ile Gly Leu Phe Leu Val
        675                 680                 685

Leu Arg Val Gly Ile Tyr Leu Cys Ile Lys Leu Lys His Thr Lys Lys
690                 695                 700

Arg Gln Ile Tyr Thr Asp Ile Glu Met Asn Arg Leu Gly Lys
705                 710                 715

<210> SEQ ID NO 23
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Pro Met Gly Ser Leu Gln Pro Leu Ala Thr Leu Tyr Leu Leu Gly
1               5                   10                  15

Met Leu Val Ala Ser Val Leu Ala
            20

<210> SEQ ID NO 24
<211> LENGTH: 2316
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
ttcgaacaac taatatcctg tcttctctat ccctatgaaa aaaactaaca gagatcgatc      60
tgtttccttg aggagccacc atgccaatgg gatcattgca accattggca acattgtatt     120
tgttgggaat gttggttgca tcagtgttgg cagttgagaa attgtgggtt acagtttatt     180
atggagttcc agtttggaaa gaagcaacaa caacattgtt ctgtgcatct gatgcaaagg     240
catatgatac agaagttcat aatgtttggg caacacatgc atgtgttcca actgatccaa     300
atccacaaga agttgtgttg agaaatgtta cagaacattt caatatgtgg aagaataata     360
tggttgaaca aatgcaagaa gatattattt cattgtggga tcaatcattg aaaccatgtg     420
```

```
ttaaattgac accattgtgt gttacattga attgtaaaga tgttaatgca acaaatacaa    480
caaatgattc agaaggaaca atggaaagag gagaaattaa gaattgttca tttaatatta    540
caacatcaat tagagatgaa gttcagaaag aatatgcatt gttctataaa ttggatgttg    600
ttccaattga taataataat acatcatata gattgatttc atgtgataca tcagttatta    660
cacaagcatg tccaaagatt tcatttgaac caattccaat tcattattgt gcaccagcag    720
gatttgcaat cttgaaatgt aatgataaga catttaatgg aaagggacca tgcaagaatg    780
tttcaacagt tcaatgtaca catggaatta gaccagttgt ttcaacacaa ttgttgttga    840
atggatcatt ggcagaagaa gaagttgtta ttagatcaga taatttcaca aataatgcaa    900
agacaattat tgttcaattg aaagaatcag ttgaaattaa ttgtacaaga ccaaataata    960
atacaagaaa gtcaattcat attggaccag gaagagcatt ctatacaaca ggagaaatta   1020
ttggagatat tagacaagca cattgtaata tttcaagagc taaatggaat gatacattga   1080
aacaaattgt tattaaattg agagaacaat ttgagaataa gacaattgtg tttaatcatt   1140
catctggagg agatccagaa attgttatgc attcatttaa ttgtggagga gaattcttct   1200
attgtaattc aacacaattg tttaattcaa catggaataa taatacagaa ggatcaaata   1260
atacagaagg aaatacaatt acattgccat gtagaattaa acaaattatt aatatgtggc   1320
aagaagttgg aaaggctatg tatgccaccac caattagagg acaaattaga tgttcatcaa   1380
atattactgg attgttgttg acaagagatg gaggaattaa tgagaatgga acagaaatct   1440
ttagaccagg aggaggagat atgagagata attggagatc agaattgtat aaatataaag   1500
ttgttaagat tgaaccattg ggagttgcac caactaaagc aaagagaaga gttgttcaaa   1560
gagagaagag agcagttgga attggagcag tgttcttggg attcttggga gcagcaggat   1620
caacaatggg agcagcatca atgacattga cagttcaagc aagattgttg ttgtcaggaa   1680
ttgttcaaca acagaataat ttgttgagag caattgaagc acaacaaaga atgttgcaat   1740
tgacagtttg gggaattaaa caattgcaag caagagtgtt ggcagttgaa agatatttgg   1800
gagatcaaca attgttggga atttggggat gttcaggaaa gttgatttgt acaacagcag   1860
ttccatggaa tgcatcatgg tcaaataaat cattggatag aatttggaat aatatgacat   1920
ggatggaatg ggaaagagaa attgataatt atacatcaga aatttataca ttgattgaag   1980
aatcacagaa tcaacaagag aagatgaac aagaattgtt ggaattggat aaatgggcat   2040
cattgtggaa ttggtttgat attactaaat ggttgtggta tattaaatca tcaattgcat   2100
cattcttctt tattattgga ttgattattg gattgttctt ggtgttgaga gttggaattt   2160
atttgtgtat taaattgaaa catacaaaga agagacaaat ttatacagat attgaaatga   2220
atagattggg aaagtgagct caaatcctgc acaacagatt cttcatgttt gaaccaaatc   2280
aacttgtgat atcatgctca aagaggcctt aattaa                              2316
```

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide <400> SEQUENCE: 25
aggagccacc                                                             10

-continued

<210> SEQ ID NO 26
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atgccaatgg gatcattgca accattggca acattgtatt tgttgggaat gttggttgca    60
tcagtgttgg ca    72

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tcatcaattg catcattctt ctttattatt ggattgatta ttggattgtt cttggtgttg    60

<210> SEQ ID NO 28
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
agagttggaa tttatttgtg tattaaattg aaacatacaa agaagagaca aatttataca    60
gatattgaaa tgaatagatt gggaaag    87

<210> SEQ ID NO 29
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 ttaattaa    8

<210> SEQ ID NO 30
<211> LENGTH: 711
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Lys Cys Leu Leu Tyr Leu Ala Phe Leu Phe Ile Gly Val Asn Cys
1               5                   10                  15

Ala Val Glu Lys Leu Trp Val Thr Val Tyr Tyr Gly Val Pro Val Trp
            20                  25                  30

Lys Glu Ala Thr Thr Thr Leu Phe Cys Ala Ser Asp Ala Lys Ala Tyr
        35                  40                  45

Asp Thr Glu Val His Asn Val Trp Ala Thr His Ala Cys Val Pro Thr
    50                  55                  60

-continued

```
Asp Pro Asn Pro Gln Glu Val Val Leu Glu Asn Val Thr Glu His Phe
 65                  70                  75                  80

Asn Met Trp Lys Asn Asn Met Val Glu Gln Met Gln Glu Asp Ile Ile
                 85                  90                  95

Ser Leu Trp Asp Gln Ser Leu Lys Pro Cys Val Lys Leu Thr Pro Leu
            100                 105                 110

Cys Val Thr Leu Asn Cys Lys Asp Val Asn Ala Thr Asn Thr Thr Asn
        115                 120                 125

Asp Ser Glu Gly Thr Met Glu Arg Gly Glu Ile Lys Asn Cys Ser Phe
130                 135                 140

Asn Ile Thr Thr Ser Ile Arg Asp Glu Val Gln Lys Glu Tyr Ala Leu
145                 150                 155                 160

Phe Tyr Lys Leu Asp Val Val Pro Ile Asp Asn Asn Asn Thr Ser Tyr
                165                 170                 175

Arg Leu Ile Ser Cys Asp Thr Ser Val Ile Thr Gln Ala Cys Pro Lys
            180                 185                 190

Ile Ser Phe Glu Pro Ile Pro Ile His Tyr Cys Ala Pro Ala Gly Phe
        195                 200                 205

Ala Ile Leu Lys Cys Asn Asp Lys Thr Phe Asn Gly Lys Gly Pro Cys
210                 215                 220

Lys Asn Val Ser Thr Val Gln Cys Thr His Gly Ile Arg Pro Val Val
225                 230                 235                 240

Ser Thr Gln Leu Leu Leu Asn Gly Ser Leu Ala Glu Glu Val Val
                245                 250                 255

Ile Arg Ser Asp Asn Phe Thr Asn Asn Ala Lys Thr Ile Ile Val Gln
            260                 265                 270

Leu Lys Glu Ser Val Glu Ile Asn Cys Thr Arg Pro Asn Asn Asn Thr
        275                 280                 285

Arg Lys Ser Ile His Ile Gly Pro Gly Arg Ala Phe Tyr Thr Thr Gly
290                 295                 300

Glu Ile Ile Gly Asp Ile Arg Gln Ala His Cys Asn Ile Ser Arg Ala
305                 310                 315                 320

Lys Trp Asn Asp Thr Leu Lys Gln Ile Val Ile Lys Leu Arg Glu Gln
                325                 330                 335

Phe Glu Asn Lys Thr Ile Val Phe Asn His Ser Ser Gly Gly Asp Pro
            340                 345                 350

Glu Ile Val Met His Ser Phe Asn Cys Gly Gly Glu Phe Phe Tyr Cys
        355                 360                 365

Asn Ser Thr Gln Leu Phe Asn Ser Thr Trp Asn Asn Asn Thr Glu Gly
370                 375                 380

Ser Asn Asn Thr Glu Gly Asn Thr Ile Thr Leu Pro Cys Arg Ile Lys
385                 390                 395                 400

Gln Ile Ile Asn Met Trp Gln Glu Val Gly Lys Ala Met Tyr Ala Pro
                405                 410                 415

Pro Ile Arg Gly Gln Ile Arg Cys Ser Ser Asn Ile Thr Gly Leu Leu
            420                 425                 430

Leu Thr Arg Asp Gly Gly Ile Asn Glu Asn Gly Thr Glu Ile Phe Arg
        435                 440                 445

Pro Gly Gly Gly Asp Met Arg Asp Asn Trp Arg Ser Glu Leu Tyr Lys
450                 455                 460

Tyr Lys Val Val Lys Ile Glu Pro Leu Gly Val Ala Pro Thr Lys Ala
465                 470                 475                 480
```

```
Lys Arg Arg Val Val Gln Arg Glu Lys Arg Ala Val Gly Ile Gly Ala
                485                 490                 495
Val Phe Leu Gly Phe Leu Gly Ala Ala Gly Ser Thr Met Gly Ala Ala
            500                 505                 510
Ser Met Thr Leu Thr Val Gln Ala Arg Leu Leu Leu Ser Gly Ile Val
        515                 520                 525
Gln Gln Gln Asn Asn Leu Leu Arg Ala Ile Glu Ala Gln Gln Arg Met
    530                 535                 540
Leu Gln Leu Thr Val Trp Gly Ile Lys Gln Leu Gln Ala Arg Val Leu
545                 550                 555                 560
Ala Val Glu Arg Tyr Leu Gly Asp Gln Gln Leu Leu Gly Ile Trp Gly
                565                 570                 575
Cys Ser Gly Lys Leu Ile Cys Thr Thr Ala Val Pro Trp Asn Ala Ser
            580                 585                 590
Trp Ser Asn Lys Ser Leu Asp Arg Ile Trp Asn Asn Met Thr Trp Met
        595                 600                 605
Glu Trp Glu Arg Glu Ile Asp Asn Tyr Thr Ser Glu Ile Tyr Thr Leu
    610                 615                 620
Ile Glu Glu Ser Gln Asn Gln Gln Glu Lys Asn Glu Gln Glu Leu Leu
625                 630                 635                 640
Glu Leu Asp Lys Trp Ala Ser Leu Trp Asn Trp Phe Asp Ile Thr Lys
                645                 650                 655
Trp Leu Trp Tyr Ile Lys Ser Ser Ile Ala Ser Phe Phe Ile Ile
            660                 665                 670
Gly Leu Ile Ile Gly Leu Phe Leu Val Leu Arg Val Gly Ile Tyr Leu
        675                 680                 685
Cys Ile Lys Leu Lys His Thr Lys Lys Arg Gln Ile Tyr Thr Asp Ile
    690                 695                 700
Glu Met Asn Arg Leu Gly Lys
705                 710

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Met Lys Cys Leu Leu Tyr Leu Ala Phe Leu Phe Ile Gly Val Asn Cys
1               5                   10                  15
Ala

<210> SEQ ID NO 32
<211> LENGTH: 2295
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
ttcgaacaac taatatcctg tcttctctat ccctatgaaa aaaactaaca gagatcgatc      60
tgtttccttg aggagccacc atgaagtgcc ttttgtactt agcttttta ttcatcgggg      120 tgaattgcgc tgttgagaaa ttgtgggtta cagtttatta tggagttcca gtttggaaag    180
aagcaacaac aacattgttc tgtgcatctg atgcaaaggc atatgataca gaagttcata    240
```

```
atgtttgggc aacacatgca tgtgttccaa ctgatccaaa tccacaagaa gttgtgttgg    300
agaatgttac agaacatttc aatatgtgga agaataatat ggttgaacaa atgcaagaag    360
atattatttc attgtgggat caatcattga aaccatgtgt taaattgaca ccattgtgtg    420
ttacattgaa ttgtaaagat gttaatgcaa caaatacaac aaatgattca gaaggaacaa    480
tggaaagagg agaaattaag aattgttcat ttaatattac aacatcaatt agagatgaag    540
ttcagaaaga atatgcattg ttctataaat tggatgttgt tccaattgat aataataata    600
catcatatag attgatttca tgtgatacat cagttattac acaagcatgt ccaaagattt    660
catttgaacc aattccaatt cattattgtg caccagcagg atttgcaatc ttgaaatgta    720
atgataagac atttaatgga aagggaccat gcaagaatgt ttcaacagtt caatgtacac    780
atggaattag accagttgtt tcaacacaat tgttgttgaa tggatcattg gcagaagaag    840
aagttgttat tagatcagat aatttcacaa ataatgcaaa gacaattatt gttcaattga    900
aagaatcagt tgaaattaat tgtacaagac caaataataa tacaagaaag tcaattcata    960
ttggaccagg aagagcattc tatacaacag agaaattat tggagatatt agacaagcac    1020
attgtaatat ttcaagagct aaatggaatg atacattgaa acaaattgtt attaaattga    1080
gagaacaatt tgagaataag acaattgtgt ttaatcattc atctggagga gatccagaaa    1140
ttgttatgca ttcatttaat tgtggaggag aattcttcta ttgtaattca acacaattgt    1200
ttaattcaac atggaataat aatacagaag gatcaaataa tacagaagga aatacaatta    1260
cattgccatg tagaattaaa caaattatta atatgtggca agaagttgga aaggctatgt    1320
atgcaccacc aattagagga caaattagat gttcatcaaa tattactgga ttgttgttga    1380
caagagatgg aggaattaat gagaatggaa cagaaatctt tagaccagga ggaggagata    1440
tgagagataa ttggagatca gaattgtata aatataaagt tgttaagatt gaaccattgg    1500
gagttgcacc aactaaagca aagagaagag ttgttcaaag agagaagaga gcagttggaa    1560
ttggagcagt gttcttggga ttcttgggag cagcaggatc aacaatggga gcagcatcaa    1620
tgacattgac agttcaagca agattgttgt tgtcaggaat tgttcaacaa cagaataatt    1680
tgttgagagc aattgaagca caacaaaagaa tgttgcaatt gacagtttgg ggaattaaac    1740
aattgcaagc aagagtgttg gcagttgaaa gatatttggg agatcaacaa ttgttgggaa    1800
tttggggatg ttcaggaaag ttgatttgta acagcagt tccatggaat gcatcatggt    1860
caaataaatc attggataga atttggaata atatgacatg gatggaatgg gaaagagaaa    1920
ttgataatta tacatcagaa atttatacat tgattgaaga atcacagaat caacaagaga    1980
agaatgaaca agaattgttg gaattggata aatgggcatc attgtggaat tggtttgata    2040
ttactaaatg gttgtggtat attaaatcat caattgcatc attcttcttt attattggat    2100
tgattattgg attgttcttg gtgttgagag ttggaattta tttgtgtatt aaattgaaac    2160
atacaaagaa gagacaaatt tatacagata ttgaaatgaa tagattggga aagtgagctc    2220
aaatcctgca aacagattc ttcatgtttg aaccaaatca acttgtgata tcatgctcaa    2280
agaggcctta attaa                                                      2295
```

<210> SEQ ID NO 33
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<210> SEQ ID NO 33
<400> SEQUENCE: 33 ttcgaa                                                                  6

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atgaagtgcc ttttgtactt agctttttta ttcatcgggg tgaattgcgc t              51

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tcatcaattg catcattctt ctttattatt ggattgatta ttggattgtt cttggtgttg      60

<210> SEQ ID NO 36
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
agagttggaa tttatttgtg tattaaattg aaacatacaa agaagagaca aatttataca      60
gatattgaaa tgaatagatt gggaaag                                          87

<210> SEQ ID NO 37
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Ala Ile Val Gln
130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Asp Ile Cys Pro Thr
                165                 170                 175

Val His Asn Ser Thr Thr Trp His Ser Asp Tyr Lys Val Lys Gly Leu
                180                 185                 190

Cys Asp Ser Asn Leu Ile Ser Met Asp Ile Thr Phe Phe Ser Glu Asp
                195                 200                 205

Gly Glu Leu Ser Ser Leu Gly Lys Glu Gly Thr Gly Phe Arg Ser Asn
210                 215                 220

Tyr Phe Ala Tyr Glu Thr Gly Asp Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
                260                 265                 270

Ser Ser Ile Ser Ala Pro Ser Gln Thr Ser Val Asp Val Ser Leu Ile
                275                 280                 285

Gln Asp Val Glu Arg Ile Leu Asp Tyr Ser Leu Cys Gln Glu Thr Trp
290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Val Phe Thr Ile Ile Asn
                325                 330                 335

Gly Thr Leu Lys Tyr Phe Glu Thr Arg Tyr Ile Arg Val Asp Ile Ala
                340                 345                 350

Ala Pro Ile Leu Ser Arg Met Val Gly Met Ile Ser Gly Thr Thr Thr
                355                 360                 365

Glu Arg Glu Leu Trp Asp Asp Trp Ala Pro Tyr Glu Asp Val Glu Ile
370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
                420                 425                 430

Leu Pro Asp Asp Glu Thr Leu Phe Phe Gly Asp Thr Gly Leu Ser Lys
                435                 440                 445

Asn Pro Ile Glu Phe Val Glu Gly Trp Phe Ser Ser Trp Lys Ser Ser
450                 455                 460

Ile Ala Ser Phe Phe Phe Ile Ile Gly Leu Ile Ile Gly Leu Phe Leu
465                 470                 475                 480

Val Leu Arg

<210> SEQ ID NO 38
<211> LENGTH: 1
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg
1

<210> SEQ ID NO 39
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

| atgaagtgcc | ttttgtactt | agctttttta | ttcatcgggg | tgaattgcaa | gttcaccata | 60 |
| gtttttccac | acaaccaaaa | aggaaactgg | aaaaatgttc | cttccaatta | ccattattgc | 120 |
| ccgtcaagct | cagatttaaa | ttggcataat | gacttaatag | gcacagcctt | acaagtcaaa | 180 |
| atgcccaaga | gtcacaaggc | tattcaagca | gacggttgga | tgtgtcatgc | ttccaaatgg | 240 |
| gtcactactt | gtgatttccg | ctggtacgga | ccgaagtata | taacacattc | catccgatcc | 300 |
| ttcactccat | ctgtagaaca | atgcaaggaa | agcattgaac | aaacgaaaca | aggaacttgg | 360 |
| ctgaatccag | gcttccctcc | tcaaagttgt | ggatatgcaa | ctgtgacgga | tgctgaagca | 420 |
| gcgattgtcc | aggtgactcc | tcaccatgtg | cttgttgatg | aatacacagg | agaatgggtt | 480 |
| gattcacagt | tcatcaacgg | aaaatgcagc | aatgacatat | gccccactgt | ccataactcc | 540 |
| acaacctggc | attccgacta | taaggtcaaa | gggctatgtg | attctaacct | catttccatg | 600 |
| gacatcacct | tcttctcaga | ggacggagag | ctatcatccc | taggaaagga | gggcacaggg | 660 |
| ttcagaagta | actactttgc | ttatgaaact | ggagacaagg | cctgcaaaat | gcagtactgc | 720 |
| aagcattggg | gagtcagact | cccatcaggt | gtctggttcg | agatggctga | taaggatctc | 780 |
| tttgctgcag | ccagattccc | tgaatgccca | gaagggtcaa | gtatctctgc | tccatctcag | 840 |
| acctcagtgg | atgtaagtct | cattcaggac | gttgagagga | tcttggatta | ttccctctgc | 900 |
| caagaaacct | ggagcaaaat | cagagcgggt | cttcccatct | ctccagtgga | tctcagctat | 960 |
| cttgctccta | aaaacccagg | aaccggtcct | gtctttacca | taatcaatgg | taccctaaaa | 1020 |
| tactttgaga | ccagatacat | cagagtcgat | attgctgctc | caatcctctc | aagaatggtc | 1080 |
| ggaatgatca | gtggaactac | cacagaaagg | gaactgtggg | atgactgggc | tccatatgaa | 1140 |
| gacgtggaaa | ttgacccaa | tggagttctg | aggaccagtt | caggatataa | gtttcccttta | 1200 |
| tatatgattg | acatggtat | gttggactcc | gatcttcatc | ttagctcaaa | ggctcaggtg | 1260 |
| tttgaacatc | ctcacattca | agacgctgct | tcgcagcttc | ctgatgatga | gactttattt | 1320 |
| tttggtgata | ctgggctatc | caaaaatcca | atcgagtttg | tagaaggttg | gttcagtagt | 1380 |
| tggaagagct | ctattgcctc | tttttttcttt | atcatagggt | taatcattgg | actattcttg | 1440 |
| gttctccgat | aa | | | | | 1452 |

<210> SEQ ID NO 40
<211> LENGTH: 3
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40 cga                                                                        3

```
<210> SEQ ID NO 41
<211> LENGTH: 30
<212> TYPE: PRT
<213> ORGANISM: Human immunodeficiency virus 1

<400> SEQUENCE: 41

Gln Glu Leu Leu Glu Leu Asp Lys Trp Ala Ser Leu Trp Asn Trp Phe
1               5                   10                  15

Asp Ile Thr Asn Trp Leu Trp Tyr Ile Lys Ile Phe Ile Met
            20                  25                  30

<210> SEQ ID NO 42
<211> LENGTH: 30
<212> TYPE: PRT
<213> ORGANISM: Vesicular stomatitis virus

<400> SEQUENCE: 42

Glu Ser Leu Phe Phe Gly Asp Thr Gly Leu Ser Lys Asn Pro Ile Glu
1               5                   10                  15

Leu Val Glu Gly Trp Phe Ser Ser Trp Lys Ser Ser Ile Ala
            20                  25                  30

<210> SEQ ID NO 43
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Gly Glu Leu Leu Glu Leu Asp Lys Trp Ala Ser Leu Gly
1               5                   10

<210> SEQ ID NO 44
<211> LENGTH: 19
<212> TYPE: PRT
<213> ORGANISM: Vesicular stomatitis virus

<400> SEQUENCE: 44

Glu Ser Leu Phe Phe Gly Asp Thr Gly Leu Ser Lys Asn Pro Ile Glu
1               5                   10                  15

Leu Val Glu

<210> SEQ ID NO 45
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Ser Leu Phe Phe Gly Asp Thr Gly Ser Gly Glu Leu Leu Glu Leu
1               5                   10                  15

Asp Lys Trp Ala Ser Leu Gly Leu Ser Lys Asn Pro Ile Glu Leu Val
            20                  25                  30

Glu

<210> SEQ ID NO 46
<211> LENGTH: 19
<212> TYPE: PRT
<213> ORGANISM: Human immunodeficiency virus 1
```

```
<400> SEQUENCE: 46

Glu Leu Leu Glu Leu Asp Lys Trp Ala Ser Leu Trp Asn Trp Phe Asp
1               5                   10                  15

Ile Thr Asn

<210> SEQ ID NO 47
<211> LENGTH: 16
<212> TYPE: PRT
<213> ORGANISM: Vesicular stomatitis virus

<400> SEQUENCE: 47

Ser Lys Asn Pro Ile Glu Leu Val Glu Gly Trp Phe Ser Ser Trp Lys
1               5                   10                  15

<210> SEQ ID NO 48
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Lys Asn Pro Ile Glu Leu Leu Glu Leu Asp Lys Trp Ala Ser Leu
1               5                   10                  15

Trp Asn Trp Phe Ser Ser Trp Lys
            20

<210> SEQ ID NO 49
<211> LENGTH: 12
<212> TYPE: PRT
<213> ORGANISM: Human immunodeficiency virus 1

<400> SEQUENCE: 49

Trp Phe Asp Ile Thr Asn Trp Leu Trp Tyr Ile Lys
1               5                   10

<210> SEQ ID NO 50
<211> LENGTH: 15
<212> TYPE: PRT
<213> ORGANISM: Vesicular stomatitis virus

<400> SEQUENCE: 50

Glu Leu Val Glu Gly Trp Phe Ser Ser Trp Lys Ser Ser Ile Ala
1               5                   10                  15

<210> SEQ ID NO 51
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Glu Gly Trp Phe Asp Ile Thr Asn Trp Leu Trp Tyr Ile Lys Ser
1               5                   10                  15

Ser Ile Ala

<210> SEQ ID NO 52
<211> LENGTH: 34
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 52

```
Ser Lys Asn Pro Ile Glu Leu Leu Glu Leu Asp Lys Trp Ala Ser Leu
1               5                   10                  15

Trp Asn Trp Phe Asp Ile Thr Asn Trp Leu Trp Tyr Ile Lys Ser Ser
                20                  25                  30

Ile Ala
```

<210> SEQ ID NO 53
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Met Lys Cys Leu Leu Tyr Leu Ala Phe Leu Phe Ile Gly Val Asn Cys
1               5                   10                  15

Lys Ala Ser Gly Tyr Lys Phe Pro Leu Tyr Met Ile Gly His Gly Met
                20                  25                  30

Leu Asp Ser Asp Leu His Leu Ser Ser Lys Ala Gln Val Phe Glu His
            35                  40                  45

Pro His Ile Gln Asp Ala Ala Ser Gln Leu Pro Asp Asp Glu Ser Leu
        50                  55                  60

Phe Phe Gly Asp Thr Gly Leu Ser Lys Asn Pro Ile Glu Leu Val Glu
65                  70                  75                  80

Gly Trp Phe Ser Ser Trp Lys Ser Ser Ile Ala Ser Phe Phe Phe Ile
                85                  90                  95

Ile Gly Leu Ile Ile Gly Leu Phe Leu Val Leu Arg Val Gly Ile His
                100                 105                 110

Leu Cys Ile Lys Leu Lys His Thr Lys Lys Arg Gln Ile Tyr Thr Asp
            115                 120                 125

Ile Glu Met Asn Arg Leu Gly Lys
        130                 135
```

<210> SEQ ID NO 54
<211> LENGTH: 6973
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg acccccgccc attgacgtca taatgacgt atgttcccat      300 agtaacgcca atagggactt tccattgacg tcaatgggtg gagtatttac ggtaaactgc     360
ccacttggca gtacatcaag tgtatcatat gccaagtccg ccccctattg acgtcaatga     420
cggtaaatgg cccgcctggc attatgccca gtacatgacc ttacgggact tcctacttg     480
```

```
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaacaactg    660
cgatcgcccg ccccgttgac gcaaatgggc ggtaggcgtg tacggtggga ggtctatata    720
agcagagctc gtttagtgaa ccgtcagatc actagaagct ttattgcggt agtttatcac    780
agttaaattg ctaacgcagt cagtgcttct gacacaacag tctcgaactt aagctgcagt    840
gactctctta aggtagcctt gcagaagttg gtcgtgaggc actgggcagg taagtatcaa    900
ggttacaaga caggtttaag gagaccaata gaaactgggc ttgtcgagac agagaagact    960
cttgcgtttc tgataggcac ctattggtct tactgacatc cactttgcct ttctctccac   1020
aggtgtccac tcccagttca attacagctc ttaaggcgag agtactcgta cgctagcctc   1080
gagaggagcc accatgaagt gcctgctgta cctggccttc ctgttcatcg gcgtgaactg   1140
caagttcacc atcgtgttcc cccacaacca aagggcaac tggaagaacg tgcccagcaa   1200
ctaccactac tgccccagca gcagcgacct gaactggcac aacgacctga tcggcaccgc   1260
cctgcaagtc aagatgccca agagccacaa ggccatccag gccgacggct ggatgtgcca   1320
cgccagcaag tgggtgacca cctgcgactt ccggtggtac ggccccaagt acatcaccca   1380
cagcatccgc agcttcaccc caagcgtgga gcagtgcaag gagagcatcg agcagaccaa   1440
gcagggcacc tggctgaacc ccggcttccc tccacaaagc tgcggctacg ccaccgtgac   1500
cgacgccgag gccgccatcg tgcaggtgac ccctcaccac gtgctggtgg acgagtacac   1560
cggcgagtgg gtggacagcc agttcatcaa cggcaagtgc agcaacgaca tctgccccac   1620
cgtgcacaac agcaccacct ggcacagcga ctacaaagtg aagggcctgt gcgacagcaa   1680
cctgatcagc accgacatca ccttcttctc cgaggacggc gagctgagca gcctgggcaa   1740
ggagggcacc ggcttccgca gcaactactt cgcctacgag accggcgaca aggcctgcaa   1800
gatgcagtac tgcaagcact ggggcgtgcg cctgcccagc ggcgtgtggt tcgagatggc   1860
cgacaaggac ctgttcgccg ccgccgcett ccccgagtgc cccgagggca gcagcatcag   1920
cgccccaagc cagaccagcg tggacgtgag cctgatccag gacgtggagc gcatcctgga   1980
ctacagcctg tgccaggaga cctggagcaa gatccgcgcc ggcctgccca tcagcccgt    2040 ggacctgagc tacctggccc ctaagaaccc cggcaccggc cccgtgttca ccatcatcaa   2100 cggcacccctg aagtacttcg agaccgcta catccgcgtg gacatcgccg cccaatcct   2160 gagccgcatg gtgggcatga tcagcggcac caccaccgag cgcgagctgt gggacgactg   2220 ggcccctac gaggacgtgg agatcggccc taacggcgtg ctgcgcacca gcctgggcta   2280
caagtttccc ctgtacatga tcggccacg catgctggac agcgaccgc acctgagcag   2340 caaggcccag gtgttcgagc atccccacat ccaggacgcc gccagccagc tgcccgacga   2400
cgagaccctg ttcttcggcg acaccggcct gagcaagaac cccatcgagt tcgtggaggg   2460
ctggttcagc agctggaaga gcagcatcgc cagcttcttc ttcatcatcg gcctgatcat   2520
cggcctgttc ctggtgctgc gcgtgggcat ctacctgtgc atcaagctga agcacaccaa   2580
gaagcgccag atctacaccg acatcgagat gaaccgcctg ggcaagtaaa gcggccgctt   2640
ccctttagtg agggttaatg cttcgagcag acatgataag atacattgat gagtttggac   2700
aaaccacaac tagaatgcag tgaaaaaaat gctttatttg tgaaatttgt gatgctattg   2760
ctttatttgt aaccattata agctgcaata acaagttaa caacaacaat tgcattcatt   2820
ttatgtttca ggttcagggg gagatgtggg aggttttta aagcaagtaa aacctctaca   2880
```

```
aatgtggtaa aatccgataa ggatcgatcc gggctggcgt aatagcgaag aggcccgcac    2940
cgatcgccct tcccaacagt tgcgcagcct gaatggcgaa tggacgcgcc ctgtagcggc    3000
gcattaagcg cggcgggtgt ggtggttacg cgcagcgtga ccgctacact tgccagcgcc    3060
ctagcgcccg ctcctttcgc tttcttccct tcctttctcg ccacgttcgc cggctttccc    3120
cgtcaagctc taaatcgggg gctcccttta gggttccgat ttagtgcttt acggcacctc    3180
gaccccaaaa aacttgatta gggtgatggt tcacgtagtg ggccatcgcc ctgatagacg    3240 gttttttcgcc ctttgacgtt ggagtccacg ttctttaata gtggactctt gttccaaact    3300
ggaacaacac tcaaccctat ctcggtctat tcttttgatt tataagggat tttgccgatt    3360
tcggcctatt ggttaaaaaa tgagctgatt taacaaaaat ttaacgcgaa ttttaacaaa    3420
atattaacgc ttacaatttc ctgatgcggt attttctcct tacgcatctg tgcggtattt    3480
cacaccgcat acgcggatct cgcagcacc atggcctgaa ataacctctg aaagaggaac    3540
ttggttaggt accttctgag gcggaaagaa ccagctgtgg aatgtgtgtc agttagggtg    3600
tggaaagtcc ccaggctccc cagcaggcag aagtatgcaa agcatgcatc tcaattagtc    3660
agcaaccagg tgtggaaagt ccccaggctc cccagcaggc agaagtatgc aaagcatgca    3720
tctcaattag tcagcaacca tagtcccgcc cctaactccg cccatcccgc ccctaactcc    3780
gcccagttcc gcccattctc cgccccatgg ctgactaatt ttttttattt atgcagaggc    3840
cgaggccgcc tcggcctctg agctattcca gaagtagtga ggaggctttt ttggaggcct    3900
aggcttttgc aaaaagcttg attcttctga cacaacagtc tcgaacttaa ggctagagcc    3960
accatgattg aacaagatgg attgcacgca ggttctccgg ccgcttgggt ggagaggcta    4020
ttcggctatg actgggcaca acagacaatc ggctgctctg atgccgccgt gttccggctg    4080
tcagcgcagg ggcgcccggt tctttttgtc aagaccgacc tgtccggtgc cctgaatgaa    4140
ctgcaggacg aggcagcgcg gctatcgtgg ctggccacga cgggcgttcc ttgcgcagct    4200
gtgctcgacg ttgtcactga agcgggaagg gactggctgc tattgggcga agtgccgggg    4260
caggatctcc tgtcatctca ccttgctcct gccgagaaag tatccatcat ggctgatgca    4320
atgcggcggt gcatacgct tgatccggct acctgcccat tcgaccacca agcgaaacat    4380
cgcatcgagc gagcacgtac tcggatggaa gccggtcttg tcgatcagga tgatctggac    4440
gaagagcatc aggggctcgc gccagccgaa ctgttcgcca ggctcaaggc gcgcatgccc    4500
gacggcgagg atctcgtcgt gacccatggc gatgcctgct tgccgaatat catggtggaa    4560
aatggccgct tttctggatt catcgactgt ggccggctgg gtgtggcgga ccgctatcag    4620
gacatagcgt tggctacccg tgatattgct gaagagcttg gcggcgaatg gctgaccgc    4680 ttcctcgtgc tttacggtat cgccgctccc gattcgcagc gcatcgcctt ctatcgcctt    4740
cttgacgagt tcttctgagc gggactctgg ggttcgaaat gaccgaccaa gcgacgccca    4800
acctgccatc acgatggccg caataaaata tctttatttt cattacatct gtgtgttggt    4860
tttttgtgtg aatcgatagc gataaggatc cgcgtatggt gcactctcag tacaatctgc    4920
tctgatgccg catagttaag ccagccccga cacccgccaa cacccgctga cgcgccctga    4980
cgggcttgtc tgctcccggc atccgcttac agacaagctg tgaccgtctc cgggagctgc    5040
atgtgtcaga ggttttcacc gtcatcaccg aaacgcgcga cgaaaggg cctcgtgata    5100 cgcctatttt tataggttaa tgtcatgata ataatggttt cttagacgtc aggtggcact    5160
tttcggggaa atgtgcgcgg aaccctatt tgtttatttt tctaaataca ttcaaatatg    5220
tatccgctca tgagacaata accctgataa atgcttcaat aatattgaaa aaggaagagt    5280
```

| atgagtattc aacatttccg tgtcgccctt attcccttttt ttgcggcatt ttgccttcct | 5340 |
| gtttttgctc acccagaaac gctggtgaaa gtaaaagatg ctgaagatca gttgggtgca | 5400 |
| cgagtgggtt acatcgaact ggatctcaac agcggtaaga tccttgagag ttttcgcccc | 5460 |
| gaagaacgtt ttccaatgat gagcactttt aaagttctgc tatgtggcgc ggtattatcc | 5520 |
| cgtattgacg ccgggcaaga gcaactcggt cgccgcatac actattctca gaatgacttg | 5580 |
| gttgagtact caccagtcac agaaaagcat cttacggatg gcatgacagt aagagaatta | 5640 |
| tgcagtgctg ccataaccat gagtgataac actgcggcca acttacttct gacaacgatc | 5700 |
| ggaggaccga aggagctaac cgcttttttg cacaacatgg gggatcatgt aactcgcctt | 5760 |
| gatcgttggg aaccggagct gaatgaagcc ataccaaacg acgagcgtga caccacgatg | 5820 |
| cctgtagcaa tggcaacaac gttgcgcaaa ctattaactg gcgaactact tactctagct | 5880 |
| tcccggcaac aattaataga ctggatggag gcggataaag ttgcaggacc acttctgcgc | 5940 |
| tcggcccttc cggctggctg gtttattgct gataaatctg gagccggtga gcgtgggtct | 6000 |
| cgcggtatca ttgcagcact ggggccagat ggtaagccct cccgtatcgt agttatctac | 6060 |
| acgacgggga gtcaggcaac tatggatgaa cgaaatagac agatcgctga gataggtgcc | 6120 |
| tcactgatta agcattggta actgtcagac caagtttact catatatact ttagattgat | 6180 |
| ttaaaacttc atttttaatt taaaaggatc taggtgaaga tccttttttga taatctcatg | 6240 |
| accaaaatcc cttaacgtga gttttcgttc cactgagcgt cagacccgt agaaaagatc | 6300 |
| aaaggatctt cttgagatcc tttttttctg cgcgtaatct gctgcttgca acaaaaaaa | 6360 |
| ccaccgctac cagcggtggt ttgtttgccg gatcaagagc taccaactct ttttccgaag | 6420 |
| gtaactggct tcagcagagc gcagatacca atactgttc ttctagtgta gccgtagtta | 6480 |
| ggccaccact tcaagaactc tgtagcaccg cctacatacc tcgctctgct aatcctgtta | 6540 |
| ccagtggctg ctgccagtgg cgataagtcg tgtcttaccg ggttggactc aagacgatag | 6600 |
| ttaccggata aggcgcagcg gtcgggctga acgggggggtt cgtgcacaca gcccagcttg | 6660 |
| gagcgaacga cctacaccga actgagatac ctacagcgtg agctatgaga aagcgccacg | 6720 |
| cttcccgaag ggagaaaggc ggacaggtat ccggtaagcg gcagggtcgg aacaggagag | 6780 |
| cgcacgaggg agcttccagg gggaaacgcc tggtatcttt atagtcctgt cgggtttcgc | 6840 |
| cacctctgac ttgagcgtcg attttttgtga tgctcgtcag gggggcggag cctatggaaa | 6900 |
| aacgccagca acgcggcctt tttacggttc ctggcctttt gctggccttt tgctcacatg | 6960 |
| gctcgacaga tct | 6973 |

<210> SEQ ID NO 55
<211> LENGTH: 1561
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

| ctcgagagga gccaccatga agtgcctgct gtacctggcc ttcctgttca tcggcgtgaa | 60 |
| ctgcaagttc accatcgtgt tcccccacaa ccagaagggc aactggaaga acgtgcccag | 120 |
| caactaccac tactgcccca gcagcagcga cctgaactgg cacaacgacc tgatcggcac | 180 |
| cgccctgcaa gtcaagatgc ccaagagcca caaggccatc caggccgacg gctggatgtg | 240 |
| ccacgccagc aagtgggtga ccacctgcga cttccgtgg tacggcccca gtacatcac | 300 |

```
ccacagcatc cgcagcttca cccccaagcgt ggagcagtgc aaggagagca tcgagcagac    360
caagcagggc acctggctga accccggctt ccctccacaa agctgcggct acgccaccgt    420
gaccgacgcc gaggccgcca tcgtgcaggt gacccctcac cacgtgctgg tggacgagta    480
caccggcgag tgggtggaca gccagttcat caacggcaag tgcagcaacg acatctgccc    540
caccgtgcac aacagcacca cctggcacag cgactacaaa gtgaagggcc tgtgcgacag    600
caacctgatc agcaccgaca tcaccttctt ctccgaggac ggcgagctga gcagcctggg    660
caaggagggc accggcttcc gcagcaacta cttcgcctac gagaccggcg acaaggcctg    720
caagatgcag tactgcaagc actggggcgt gcgcctgccc agcggcgtgt ggttcgagat    780
ggccgacaag gacctgttcg ccgccgcccg cttccccgag tgccccgagg gcagcagcat    840
cagcgcccca agccagacca gcgtggacgt gagcctgatc caggacgtgg agcgcatcct    900
ggactacagc ctgtgccagg agacctggag caagatccgc gccggcctgc ccatcagccc    960
cgtggacctg agctacctgg cccctaagaa ccccggcacc ggccccgtgt tcaccatcat    1020
caacggcacc ctgaagtact tcgagacccg ctacatccgc gtggacatcg ccgccccaat    1080
cctgagccgc atggtgggca tgatcagcgg caccaccacc gagcgcgagc tgtgggacga    1140
ctgggcccct tacgaggacg tggagatcgg ccctaacggc gtgctgcgca ccagcctggg    1200
ctacaagttt cccctgtaca tgatcggcca cggcatgctg gacagcgacc tgcacctgag    1260
cagcaaggcc caggtgttcg agcatcccca catccaggac gccgccagcc agctgcccga    1320
cgacgagacc ctgttcttcg gcgacaccgg cctgagcaag aaccccatcg agttcgtgga    1380
gggctggttc agcagctgga agagcagcat cgccagcttc ttcttcatca tcggcctgat    1440
catcggcctg ttcctggtgc tgcgcgtggg catctacctg tgcatcaagc tgaagcacac    1500
caagaagcgc cagatctaca ccgacatcga gatgaaccgc ctgggcaagt aaagcggccg    1560
c                                                                    1561
```